(12) United States Patent
Yu et al.

(10) Patent No.: US 10,302,807 B2
(45) Date of Patent: May 28, 2019

(54) SYSTEMS AND METHODS FOR DETECTING THREATS AND CONTRABAND IN CARGO

(71) Applicant: Rapiscan Systems, Inc., Torrance, CA (US)

(72) Inventors: Songyang Yu, Milpitas, CA (US); Rupa Chittineni, Santa Clara, CA (US); Mark J. McCarthy, Danville, CA (US)

(73) Assignee: Rapiscan Systems, Inc., Torrance, CA (US)

(*) Notice: Subject to any disclaimer, the term of this patent is extended or adjusted under 35 U.S.C. 154(b) by 135 days.

(21) Appl. No.: 15/431,011

(22) Filed: Feb. 13, 2017

(65) Prior Publication Data

US 2017/0242148 A1 Aug. 24, 2017

Related U.S. Application Data

(60) Provisional application No. 62/298,383, filed on Feb. 22, 2016.

(51) Int. Cl.
*G06K 9/00* (2006.01)
*G01V 5/00* (2006.01)
(Continued)

(52) U.S. Cl.
CPC .......... *G01V 5/0083* (2013.01); *G01F 17/00* (2013.01); *G01F 22/00* (2013.01); *G01N 23/04* (2013.01);
(Continued)

(58) Field of Classification Search
CPC .......... G01V 5/0016; G01V 5/0008; G01V 5/0025; G01V 5/0066; G01N 23/04
(Continued)

(56) References Cited

U.S. PATENT DOCUMENTS

| 2,006 A | 3/1841 | Read |
|---|---|---|
| 2,636,619 A | 4/1953 | Alexander |

(Continued)

FOREIGN PATENT DOCUMENTS

| CA | 2574402 A1 | 1/2006 |
|---|---|---|
| CA | 2319958 C | 3/2007 |

(Continued)

OTHER PUBLICATIONS

International Search Report for PCT/US2017/017642, dated Jun. 29, 2017.
(Continued)

*Primary Examiner* — Charlotte M Baker
(74) *Attorney, Agent, or Firm* — Novel IP

(57) ABSTRACT

The present specification discloses systems and methods for identifying and reporting contents of a tanker, container or vehicle. Programmatic tools are provided to assist an operator in analyzing contents of a tanker, container or vehicle. Manifest data is automatically imported into the system for each shipment, thereby helping security personnel to quickly determine container contents. In case of a mismatch between container contents shown by manifest data and the contents as ascertained from the scanning system, the container or vehicle may be withheld for further inspection.

14 Claims, 55 Drawing Sheets

(51) Int. Cl.
*G01F 17/00* (2006.01)
*G01N 23/04* (2018.01)
*G06K 9/62* (2006.01)
*G06T 7/60* (2017.01)
*G01F 22/00* (2006.01)
*G06Q 10/08* (2012.01)
*G06Q 50/28* (2012.01)
*G06T 7/62* (2017.01)
*G06K 9/46* (2006.01)

(52) U.S. Cl.
CPC ....... *G01V 5/0016* (2013.01); *G06K 9/00771* (2013.01); *G06K 9/6267* (2013.01); *G06Q 10/083* (2013.01); *G06Q 50/28* (2013.01); *G06T 7/60* (2013.01); *G06T 7/62* (2017.01); *G01N 2223/401* (2013.01); *G01N 2223/639* (2013.01); *G06K 9/4604* (2013.01); *G06T 2207/10116* (2013.01)

(58) Field of Classification Search
USPC .......................................................... 382/103
See application file for complete search history.

(56) References Cited

U.S. PATENT DOCUMENTS

| | | |
|---|---|---|
| 3,124,679 A | 3/1964 | Tittman et al. |
| 3,240,971 A | 3/1966 | Morgan |
| 3,275,831 A | 9/1966 | Martin |
| 3,374,355 A | 3/1968 | Parratt |
| 3,439,166 A | 4/1969 | Chope |
| 3,670,164 A | 6/1972 | Hardy et al. |
| 3,780,291 A | 12/1973 | Stein |
| 3,784,827 A | 1/1974 | Calhoun |
| 3,790,785 A | 2/1974 | Paolini et al. |
| 3,808,444 A | 4/1974 | Schneeberger et al. |
| 3,832,545 A | 8/1974 | Bartko |
| 3,835,324 A | 9/1974 | Weigle |
| 3,837,502 A | 9/1974 | Hornagold |
| 3,872,287 A | 3/1975 | Koeman |
| 3,904,923 A | 9/1975 | Schwartz |
| 3,980,889 A | 9/1976 | Haas |
| 3,997,787 A | 12/1976 | Fearon et al. |
| 4,020,346 A | 4/1977 | Dennis |
| 4,047,036 A | 9/1977 | Smith |
| 4,064,440 A | 12/1977 | Roder |
| 4,158,773 A | 6/1979 | Novak |
| 4,164,138 A | 8/1979 | Burkhart |
| 4,173,010 A | 10/1979 | Hoffmann |
| 4,217,641 A | 8/1980 | Naparstek |
| 4,229,654 A | 10/1980 | Arya |
| 4,239,969 A | 12/1980 | Galetta |
| 4,247,774 A | 1/1981 | Brooks |
| 4,251,726 A | 2/1981 | Alvarez |
| 4,255,659 A | 3/1981 | Kaufman |
| 4,338,626 A | 7/1982 | Lemelson |
| 4,366,382 A | 12/1982 | Kotowski |
| 4,379,348 A | 4/1983 | Haas |
| 4,379,481 A | 4/1983 | Juner |
| 4,383,327 A | 5/1983 | Kruger |
| 4,418,575 A | 12/1983 | Hundt |
| 4,430,568 A | 2/1984 | Yoshida |
| 4,470,303 A | 9/1984 | ODonnell |
| 4,480,899 A | 11/1984 | Sprague |
| 4,482,958 A | 11/1984 | Nakayama |
| 4,509,075 A | 4/1985 | Simms |
| 4,535,246 A | 8/1985 | Shani |
| 4,539,648 A | 9/1985 | Schatzki |
| 4,558,220 A | 12/1985 | Evans |
| 4,566,113 A | 1/1986 | Doenges |
| 4,573,198 A | 2/1986 | Anderson |
| 4,580,219 A | 4/1986 | Pelc |
| 4,590,558 A | 5/1986 | Glover |
| 4,598,202 A | 7/1986 | Koechner |
| 4,599,740 A | 7/1986 | Cable |
| 4,612,666 A | 9/1986 | King |
| 4,637,056 A | 1/1987 | Sherman |
| 4,651,297 A | 3/1987 | Schlunt |
| 4,653,109 A | 3/1987 | Lemelson |
| 4,658,408 A | 4/1987 | Amor |
| 4,697,594 A | 10/1987 | Mayo, Jr. |
| 4,709,333 A | 11/1987 | Crawford |
| 4,722,096 A | 1/1988 | Dietrich |
| 4,724,543 A | 2/1988 | Klevecz |
| 4,725,733 A | 2/1988 | Horman et al. |
| 4,736,399 A | 4/1988 | Okazaki |
| 4,736,401 A | 4/1988 | Donges |
| 4,737,650 A | 4/1988 | West |
| 4,755,680 A | 7/1988 | Logan |
| 4,756,015 A | 7/1988 | Doenges |
| 4,759,047 A | 7/1988 | Donges |
| 4,775,895 A | 10/1988 | Traupe |
| 4,783,794 A | 11/1988 | Dietrich |
| 4,788,704 A | 11/1988 | Donges |
| 4,793,261 A | 12/1988 | Schwaemmle |
| 4,795,253 A | 1/1989 | Sandridge |
| 4,817,123 A | 3/1989 | Sones |
| 4,819,188 A | 4/1989 | Matsubara |
| 4,832,447 A | 5/1989 | Javidi |
| 4,837,733 A | 6/1989 | Shiraishi |
| 4,838,644 A | 6/1989 | Ochoa |
| 4,841,554 A | 6/1989 | Doenges |
| 4,849,912 A | 7/1989 | Leberl |
| 4,862,358 A | 8/1989 | Kimura |
| 4,869,574 A | 9/1989 | Hartman |
| 4,870,670 A | 9/1989 | Geus |
| 4,873,708 A | 10/1989 | Cusano |
| 4,884,289 A | 11/1989 | Glockmann |
| 4,887,899 A | 12/1989 | Hung |
| 4,893,015 A | 1/1990 | Kubierschky |
| 4,916,722 A | 4/1990 | Ema |
| 4,933,961 A | 6/1990 | Rushbrooke |
| 4,941,162 A | 7/1990 | Vartsky |
| 4,955,060 A | 9/1990 | Katsuki et al. |
| 4,957,250 A | 9/1990 | Hararat-Tehrani |
| 4,973,846 A | 11/1990 | Lanza |
| 4,989,229 A | 1/1991 | Negrelli |
| 5,003,616 A | 3/1991 | Orita |
| 5,012,917 A | 5/1991 | Gilbert |
| 5,014,293 A | 5/1991 | Boyd |
| 5,018,178 A | 5/1991 | Katsumata |
| 5,020,111 A | 5/1991 | Weber |
| 5,022,062 A | 6/1991 | Annis |
| 5,034,812 A | 7/1991 | Rawlings |
| 5,041,728 A | 8/1991 | Spacher |
| 5,041,993 A | 8/1991 | Rawlings |
| 5,056,130 A | 10/1991 | Engel |
| 5,060,249 A | 10/1991 | Eisen |
| 5,063,602 A | 11/1991 | Peppers |
| 5,065,418 A | 11/1991 | Bermbach |
| 5,070,519 A | 12/1991 | Stein |
| 5,073,782 A | 12/1991 | Huguenin |
| 5,079,698 A | 1/1992 | Grenier |
| 5,091,924 A | 2/1992 | Bermbach |
| 5,098,640 A | 3/1992 | Gozani |
| 5,107,351 A | 4/1992 | Leib |
| 5,109,276 A | 4/1992 | Nudelman |
| 5,109,691 A | 5/1992 | Corrigan |
| 5,125,015 A | 6/1992 | Shimoni |
| 5,132,811 A | 7/1992 | Iwaki |
| 5,132,842 A | 7/1992 | Yeh |
| 5,132,998 A | 7/1992 | Tsutsui |
| 5,138,167 A | 8/1992 | Barnes |
| 5,150,229 A | 9/1992 | Takesue |
| 5,151,588 A | 9/1992 | Kiri |
| 5,162,652 A | 11/1992 | Cohen |
| 5,175,756 A | 12/1992 | Pongratz |
| 5,179,581 A | 1/1993 | Annis |
| 5,181,234 A | 1/1993 | Smith |
| 5,182,764 A | 1/1993 | Peschmann |
| 5,185,778 A | 2/1993 | Magram |
| 5,195,629 A | 3/1993 | Gottstein |
| 5,197,088 A | 3/1993 | Vincent |

(56) References Cited

U.S. PATENT DOCUMENTS

| | | |
|---|---|---|
| 5,198,669 A | 3/1993 | Namiki |
| 5,200,626 A | 4/1993 | Schultz |
| 5,202,932 A | 4/1993 | Cambier |
| 5,216,541 A | 6/1993 | Takesue |
| 5,237,598 A | 8/1993 | Albert |
| 5,239,595 A | 8/1993 | Takemura |
| 5,243,664 A | 9/1993 | Tuy |
| 5,247,561 A | 9/1993 | Kotowski |
| 5,257,085 A | 10/1993 | Ulich |
| 5,257,322 A | 10/1993 | Matsuoka |
| 5,259,012 A | 11/1993 | Baker |
| 5,268,967 A | 12/1993 | Jang |
| 5,283,641 A | 2/1994 | Lemelson |
| 5,297,222 A | 3/1994 | Mori |
| 5,298,756 A | 3/1994 | McCollum |
| 5,299,116 A | 3/1994 | Owens |
| 5,308,986 A | 5/1994 | Walker |
| 5,309,244 A | 5/1994 | Katagiri et al. |
| 5,309,523 A | 5/1994 | Iwaki |
| 5,311,359 A | 5/1994 | Lucas |
| 5,319,544 A | 6/1994 | Schmerer |
| 5,319,547 A | 6/1994 | Krug |
| 5,323,004 A | 6/1994 | Ettinger |
| 5,323,472 A | 6/1994 | Falk |
| 5,327,286 A | 7/1994 | Sampsell |
| 5,339,350 A | 8/1994 | Thelosen |
| 5,345,081 A | 9/1994 | Rogers |
| 5,345,173 A | 9/1994 | Bito |
| 5,363,940 A | 11/1994 | Fahrion |
| 5,365,560 A | 11/1994 | Tam |
| 5,365,564 A | 11/1994 | Yashida |
| 5,367,552 A | 11/1994 | Peschmann |
| 5,371,542 A | 12/1994 | Pauli |
| 5,375,156 A | 12/1994 | Kuo-Petravic |
| 5,376,796 A | 12/1994 | Chan |
| 5,379,334 A | 1/1995 | Zimmer |
| 5,379,336 A | 1/1995 | Kramer |
| 5,388,684 A | 2/1995 | Peck |
| 5,418,380 A | 5/1995 | Simon |
| 5,420,788 A | 5/1995 | Vissers |
| 5,425,113 A | 6/1995 | Ito |
| 5,428,657 A | 6/1995 | Papanicolopoulos |
| 5,430,787 A | 7/1995 | Norton |
| 5,434,415 A | 7/1995 | Terada |
| 5,464,013 A | 11/1995 | Lemelson |
| 5,465,284 A | 11/1995 | Karellas |
| 5,481,584 A | 1/1996 | Tang |
| 5,481,622 A | 1/1996 | Gerhardt |
| 5,483,569 A | 1/1996 | Annis |
| 5,485,312 A | 1/1996 | Horner |
| 5,490,193 A | 2/1996 | Kuroda |
| 5,490,218 A | 2/1996 | Krug |
| 5,493,444 A | 2/1996 | Khoury |
| 5,493,517 A | 2/1996 | Frazier |
| 5,493,596 A | 2/1996 | Annis |
| 5,503,424 A | 4/1996 | Agopian |
| 5,506,880 A | 4/1996 | Scardino |
| 5,519,225 A | 5/1996 | Mohr |
| 5,524,133 A | 6/1996 | Neale |
| 5,528,702 A | 6/1996 | Mitsuoka |
| 5,528,703 A | 6/1996 | Lee |
| 5,541,856 A | 7/1996 | Hammermeister |
| 5,546,189 A | 8/1996 | Svetkoff |
| 5,568,256 A | 10/1996 | Korner |
| 5,580,471 A | 12/1996 | Fukumoto |
| 5,589,162 A | 12/1996 | Muraoka |
| 5,591,967 A | 1/1997 | Moake |
| 5,592,561 A | 1/1997 | Moore |
| 5,595,767 A | 1/1997 | Cinquin |
| 5,600,303 A | 2/1997 | Husseiny |
| 5,600,485 A | 2/1997 | Iwaki |
| 5,600,700 A | 2/1997 | Krug |
| 5,604,634 A | 2/1997 | Khoury |
| 5,606,167 A | 2/1997 | Miller |
| 5,619,596 A | 4/1997 | Iwaki |
| 5,625,192 A | 4/1997 | Oda |
| 5,625,717 A | 4/1997 | Hashimoto |
| 5,629,669 A | 5/1997 | Asano |
| 5,638,420 A | 6/1997 | Armistead |
| 5,642,393 A | 6/1997 | Krug |
| 5,642,394 A | 6/1997 | Rothschild |
| 5,647,018 A | 7/1997 | Benjamin |
| 5,664,574 A | 9/1997 | Chance |
| 5,668,846 A | 9/1997 | Fox |
| 5,679,956 A | 10/1997 | Johnston |
| 5,680,525 A | 10/1997 | Sakai |
| 5,684,565 A | 11/1997 | Oshida |
| 5,692,028 A | 11/1997 | Geus |
| 5,692,029 A | 11/1997 | Husseiny |
| 5,692,446 A | 12/1997 | Becker |
| 5,698,854 A | 12/1997 | Gupta |
| 5,699,400 A | 12/1997 | Lee |
| 5,703,921 A | 12/1997 | Fujita |
| 5,706,816 A | 1/1998 | Mochizuki |
| 5,726,449 A | 3/1998 | Yoshiike |
| 5,739,539 A | 4/1998 | Wang |
| 5,740,221 A | 4/1998 | Norman |
| 5,745,542 A | 4/1998 | Gordon |
| 5,748,305 A | 5/1998 | Shimono |
| 5,748,697 A | 5/1998 | Tam |
| 5,754,617 A | 5/1998 | Itoh |
| 5,754,621 A | 5/1998 | Suzuki |
| 5,756,875 A | 5/1998 | Parker |
| 5,757,981 A | 5/1998 | Kawakubo |
| 5,761,334 A | 6/1998 | Nakajima |
| 5,764,683 A | 6/1998 | Swift |
| 5,764,719 A | 6/1998 | Noettling |
| 5,768,334 A | 6/1998 | Maitrejean |
| 5,777,742 A | 7/1998 | Marron |
| 5,778,046 A | 7/1998 | Molloi |
| 5,779,641 A | 7/1998 | Hatfield |
| 5,784,429 A | 7/1998 | Arai |
| 5,786,597 A | 7/1998 | Lingren |
| 5,787,145 A | 7/1998 | Geus |
| 5,794,788 A | 8/1998 | Massen |
| 5,796,802 A | 8/1998 | Gordon |
| 5,796,868 A | 8/1998 | Dutta-Choudhury |
| 5,799,100 A | 8/1998 | Clarke |
| 5,800,355 A | 9/1998 | Hasegawa |
| 5,802,133 A | 9/1998 | Kawai |
| 5,805,660 A | 9/1998 | Perion |
| 5,809,171 A | 9/1998 | Neff |
| 5,815,198 A | 9/1998 | Vachtsevanos |
| 5,815,264 A | 9/1998 | Reed |
| 5,828,722 A | 10/1998 | Ploetz |
| 5,828,774 A | 10/1998 | Wang |
| 5,834,153 A | 11/1998 | Hasegawa |
| 5,835,558 A | 11/1998 | Maschke |
| 5,835,561 A | 11/1998 | Moorman |
| 5,838,758 A | 11/1998 | Krug |
| 5,838,759 A | 11/1998 | Armistead |
| 5,841,828 A | 11/1998 | Gordon |
| 5,841,907 A | 11/1998 | Javidi |
| 5,842,578 A | 12/1998 | Cordeiro |
| 5,850,465 A | 12/1998 | Shimura |
| 5,862,198 A | 1/1999 | Samarasekera |
| 5,862,258 A | 1/1999 | Taylor |
| 5,864,598 A | 1/1999 | Hsieh |
| 5,866,907 A | 2/1999 | Drukier |
| 5,870,449 A | 2/1999 | Lee |
| 5,877,849 A | 3/1999 | Ramer |
| 5,881,123 A | 3/1999 | Tam |
| 5,893,095 A | 4/1999 | Jain |
| 5,894,345 A | 4/1999 | Takamoto |
| 5,895,073 A | 4/1999 | Moore |
| 5,901,196 A | 5/1999 | Sauer |
| 5,901,198 A | 5/1999 | Crawford |
| 5,903,623 A | 5/1999 | Swift |
| 5,909,285 A | 6/1999 | Beaty |
| 5,909,477 A | 6/1999 | Crawford |
| 5,909,478 A | 6/1999 | Polichar |
| 5,910,765 A | 6/1999 | Slemon |
| 5,910,973 A | 6/1999 | Grodzins |
| 5,911,139 A | 6/1999 | Jain |

(56) References Cited

U.S. PATENT DOCUMENTS

| | | |
|---|---|---|
| 5,917,190 A | 6/1999 | Yodh |
| 5,926,568 A | 7/1999 | Chaney |
| 5,933,471 A | 8/1999 | Kalvin |
| 5,936,249 A | 8/1999 | Eisen |
| 5,940,468 A | 8/1999 | Huang |
| 5,943,388 A | 8/1999 | Tuemer |
| 5,951,474 A | 9/1999 | Matsunaga |
| 5,953,452 A | 9/1999 | Boone |
| 5,958,336 A | 9/1999 | Duarte |
| 5,960,104 A | 9/1999 | Conners |
| 5,974,111 A | 10/1999 | Krug |
| 5,978,440 A | 11/1999 | Kang |
| 5,981,949 A | 11/1999 | Leahy |
| 5,987,095 A | 11/1999 | Chapman |
| 5,994,706 A | 11/1999 | Allen |
| 6,005,916 A | 12/1999 | Johnson |
| 6,008,496 A | 12/1999 | Winefordner |
| 6,009,142 A | 12/1999 | Sauer |
| 6,011,266 A | 1/2000 | Bell |
| 6,011,620 A | 1/2000 | Sites |
| 6,014,628 A | 1/2000 | Kovarik, Jr. |
| 6,018,561 A | 1/2000 | Tam |
| 6,018,562 A | 1/2000 | Willson |
| 6,031,890 A | 2/2000 | Bermbach |
| 6,035,014 A | 3/2000 | Hiraoglu |
| 6,043,870 A | 3/2000 | Chen |
| 6,049,381 A | 4/2000 | Reintjes |
| 6,056,671 A | 5/2000 | Marmer |
| 6,057,761 A | 5/2000 | Yukl |
| 6,057,909 A | 5/2000 | Yahav |
| 6,058,158 A | 5/2000 | Eiler |
| 6,058,159 A | 5/2000 | Conway |
| 6,060,677 A | 5/2000 | Ulrichsen |
| 6,070,583 A | 6/2000 | Perelman |
| 6,075,591 A | 6/2000 | Vokhmin |
| 6,075,880 A | 6/2000 | Kollhof |
| 6,076,400 A | 6/2000 | Bechwati |
| 6,078,638 A | 6/2000 | Sauer |
| 6,080,994 A | 6/2000 | Carrott |
| 6,081,580 A | 6/2000 | Grodzins |
| 6,084,939 A | 7/2000 | Tamura |
| 6,088,423 A | 7/2000 | Krug |
| 6,094,472 A | 7/2000 | Smith |
| 6,097,427 A | 8/2000 | Dey |
| 6,097,483 A | 8/2000 | Komatsu |
| 6,118,850 A | 9/2000 | Mayo |
| 6,149,300 A | 11/2000 | Greenway |
| 6,151,381 A | 11/2000 | Grodzins |
| 6,153,873 A | 11/2000 | Wolf |
| 6,155,179 A | 12/2000 | Aust |
| 6,157,730 A | 12/2000 | Roever |
| 6,163,403 A | 12/2000 | Carrott |
| 6,163,591 A | 12/2000 | Benjamin |
| 6,175,417 B1 | 1/2001 | Do |
| 6,175,613 B1 | 1/2001 | Boutenko |
| 6,188,747 B1 | 2/2001 | Geus |
| 6,195,413 B1 | 2/2001 | Geus |
| 6,195,444 B1 | 2/2001 | Simanovsky |
| 6,198,795 B1 | 3/2001 | Naumann |
| 6,205,195 B1 | 3/2001 | Lanza |
| 6,205,243 B1 | 3/2001 | Migdal |
| 6,216,540 B1 | 4/2001 | Nelson |
| 6,218,943 B1 | 4/2001 | Ellenbogen |
| 6,220,099 B1 | 4/2001 | Marti |
| 6,222,902 B1 | 4/2001 | Lin |
| 6,229,872 B1 | 5/2001 | Amos |
| 6,233,303 B1 | 5/2001 | Tam |
| 6,236,704 B1 | 5/2001 | Navab |
| 6,236,708 B1 | 5/2001 | Lin |
| 6,246,778 B1 | 6/2001 | Moore |
| 6,249,341 B1 | 6/2001 | Basiji |
| 6,249,567 B1 | 6/2001 | Rothschild |
| 6,252,929 B1 | 6/2001 | Swift |
| 6,255,654 B1 | 7/2001 | Verbinski |
| 6,256,370 B1 | 7/2001 | Yavuz |
| 6,256,404 B1 | 7/2001 | Gordon |
| 6,263,044 B1 | 7/2001 | Joosten |
| 6,263,231 B1 | 7/2001 | Reitter |
| 6,266,393 B1 | 7/2001 | Ein-Gal |
| 6,271,510 B1 | 8/2001 | Boxen |
| 6,272,204 B1 | 8/2001 | Amtower |
| 6,272,230 B1 | 8/2001 | Hiraoglu |
| 6,272,233 B1 | 8/2001 | Takeo |
| 6,278,760 B1 | 8/2001 | Ogawa |
| 6,282,258 B1 | 8/2001 | Stein |
| 6,285,030 B1 | 9/2001 | Williams |
| 6,288,974 B1 | 9/2001 | Nelson |
| 6,289,235 B1 | 9/2001 | Webber |
| 6,292,260 B1 | 9/2001 | Lin |
| 6,292,530 B1 | 9/2001 | Yavus |
| 6,292,533 B1 | 9/2001 | Swift |
| 6,301,327 B1 | 10/2001 | Martens |
| 6,317,509 B1 | 11/2001 | Simanovsky |
| 6,324,243 B1 | 11/2001 | Edic |
| 6,324,245 B1 | 11/2001 | Tam |
| 6,345,113 B1 | 2/2002 | Crawford |
| 6,347,132 B1 | 2/2002 | Annis |
| 6,353,673 B1 | 3/2002 | Shnitser |
| 6,366,638 B1 | 4/2002 | Hsieh |
| 6,370,222 B1 | 4/2002 | Cornick |
| 6,373,916 B1 | 4/2002 | Inoue |
| 6,373,970 B1 | 4/2002 | Dong |
| 6,373,979 B1 | 4/2002 | Wang |
| 6,380,540 B1 | 4/2002 | Maor |
| 6,381,297 B1 | 4/2002 | Hsieh |
| 6,388,788 B1 | 5/2002 | Harris |
| 6,403,960 B1 | 6/2002 | Wellnitz |
| 6,404,841 B1 | 6/2002 | Pforr |
| 6,407,390 B1 | 6/2002 | Rozsa |
| 6,408,042 B1 | 6/2002 | Hsieh |
| 6,415,012 B1 | 7/2002 | Taguchi |
| 6,418,184 B1 | 7/2002 | Wang |
| 6,418,189 B1 | 7/2002 | Schafer |
| 6,418,194 B1 | 7/2002 | McPherson |
| 6,424,692 B1 | 7/2002 | Suzuki |
| 6,430,255 B2 | 8/2002 | Fenkart |
| 6,438,577 B1 | 8/2002 | Owens |
| 6,442,288 B1 | 8/2002 | Haerer |
| 6,445,765 B1 | 9/2002 | Frank |
| 6,448,545 B1 | 9/2002 | Chen |
| 6,453,003 B1 | 9/2002 | Springer |
| 6,459,755 B1 | 10/2002 | Li |
| 6,459,761 B1 | 10/2002 | Grodzins |
| 6,459,764 B1 | 10/2002 | Chalmers |
| 6,463,181 B2 | 10/2002 | Duarte |
| 6,473,489 B2 | 10/2002 | Bani-Hashemi |
| 6,477,221 B1 | 11/2002 | Ning |
| 6,479,826 B1 | 11/2002 | Klann |
| 6,480,285 B1 | 11/2002 | Hill |
| 6,480,564 B1 | 11/2002 | Kim |
| 6,483,894 B2 | 11/2002 | Hartick |
| 6,487,307 B1 | 11/2002 | Hennessey |
| 6,502,984 B2 | 1/2003 | Ogura |
| 6,507,025 B1 | 1/2003 | Verbinski |
| 6,507,278 B1 | 1/2003 | Brunetti |
| 6,515,285 B1 | 2/2003 | Marshall |
| 6,525,331 B1 | 2/2003 | Ngoi |
| 6,526,120 B1 | 2/2003 | Gray |
| 6,532,276 B1 | 3/2003 | Hartick |
| 6,542,574 B2 | 4/2003 | Grodzins |
| 6,542,578 B2 | 4/2003 | Ries |
| 6,542,579 B1 | 4/2003 | Takasawa |
| 6,542,580 B1 | 4/2003 | Carver |
| 6,542,628 B1 | 4/2003 | Muller |
| 6,545,281 B1 | 4/2003 | McGregor |
| 6,549,683 B1 | 4/2003 | Bergeron |
| 6,552,346 B2 | 4/2003 | Verbinski |
| 6,552,809 B1 | 4/2003 | Bergeron |
| 6,559,769 B2 | 5/2003 | Anthony |
| 6,570,177 B1 | 5/2003 | Struckhoff |
| 6,570,708 B1 | 5/2003 | Bergeron |
| 6,570,951 B1 | 5/2003 | Hsieh |
| 6,570,956 B1 | 5/2003 | Rhee |
| 6,574,296 B2 | 6/2003 | Stierstorfer |

(56) References Cited

U.S. PATENT DOCUMENTS

| | | |
|---|---|---|
| 6,574,297 B2 | 6/2003 | Tam |
| 6,580,777 B1 | 6/2003 | Ueki |
| 6,580,778 B2 | 6/2003 | Meder |
| 6,583,895 B1 | 6/2003 | Kuwahara |
| 6,584,170 B2 | 6/2003 | Aust |
| 6,586,193 B2 | 7/2003 | Yguerabide |
| 6,587,575 B1 | 7/2003 | Windham |
| 6,587,595 B1 | 7/2003 | Henkel |
| 6,597,760 B2 | 7/2003 | Beneke |
| 6,603,536 B1 | 8/2003 | Hasson |
| 6,608,921 B1 | 8/2003 | Inoue |
| 6,611,575 B1 | 8/2003 | Alyassin |
| 6,614,872 B2 | 9/2003 | Bueno |
| 6,618,466 B1 | 9/2003 | Ning |
| 6,621,887 B2 | 9/2003 | Albagli |
| 6,621,888 B2 | 9/2003 | Grodzins |
| 6,621,925 B1 | 9/2003 | Ohmori |
| 6,628,745 B1 | 9/2003 | Annis |
| 6,628,982 B1 | 9/2003 | Thomas |
| 6,628,983 B1 | 9/2003 | Gagnon |
| 6,636,581 B2 | 10/2003 | Sorenson |
| 6,637,266 B1 | 10/2003 | Froom |
| 6,644,853 B1 | 11/2003 | Kantor |
| 6,654,443 B1 | 11/2003 | Hoffman |
| 6,661,867 B2 | 12/2003 | Mario |
| 6,663,280 B2 | 12/2003 | Doenges |
| 6,665,373 B1 | 12/2003 | Kotowski |
| 6,671,508 B1 | 12/2003 | Mitsuoka |
| 6,702,459 B2 | 3/2004 | Barnes |
| 6,707,879 B2 | 3/2004 | McClelland |
| 6,713,773 B1 | 3/2004 | Lyons |
| 6,714,623 B2 | 3/2004 | Sako |
| 6,721,387 B1 | 4/2004 | Naidu |
| 6,721,391 B2 | 4/2004 | McClelland |
| 6,724,922 B1 | 4/2004 | Vilsmeier |
| 6,727,506 B2 | 4/2004 | Mallette |
| 6,731,819 B1 | 5/2004 | Fukushima |
| 6,735,274 B1 | 5/2004 | Zahavi |
| 6,735,279 B1 | 5/2004 | Jacobs |
| 6,738,450 B1 | 5/2004 | Barford |
| 6,744,909 B1 | 6/2004 | Kostrzewski |
| 6,746,864 B1 | 6/2004 | McNeil |
| 6,751,349 B2 | 6/2004 | Matama |
| 6,754,374 B1 | 6/2004 | Miller |
| 6,763,148 B1 | 7/2004 | Sternberg |
| 6,768,421 B1 | 7/2004 | Alioto |
| 6,785,357 B2 | 8/2004 | Bernardi |
| 6,785,410 B2 | 8/2004 | Vining |
| 6,791,089 B1 | 9/2004 | Caffrey |
| H2110 H | 10/2004 | Newman |
| 6,801,647 B1 | 10/2004 | Arakawa |
| 6,803,997 B2 | 10/2004 | Stanek |
| 6,804,412 B1 | 10/2004 | Wilkinson |
| 6,807,458 B2 | 10/2004 | Quackenbush |
| 6,813,395 B1 | 11/2004 | Kinjo |
| 6,825,854 B1 | 11/2004 | Beneke |
| 6,829,585 B1 | 12/2004 | Grewal |
| 6,837,422 B1 | 1/2005 | Meder |
| 6,839,403 B1 | 1/2005 | Kotowski |
| 6,839,406 B2 | 1/2005 | Ries |
| 6,843,599 B2 | 1/2005 | Le |
| 6,845,873 B1 | 1/2005 | Chattey |
| 6,856,272 B2 | 2/2005 | Levitan |
| 6,865,287 B1 | 3/2005 | Beneke |
| 6,865,509 B1 | 3/2005 | Hsiung |
| 6,868,138 B2 | 3/2005 | Clinthorne |
| 6,873,261 B2 | 3/2005 | Anthony |
| 6,876,322 B2 | 4/2005 | Keller |
| 6,891,470 B2 | 5/2005 | Bohinc, Jr. |
| 6,895,072 B2 | 5/2005 | Schrock |
| 6,895,338 B2 | 5/2005 | Hsiung |
| 6,899,540 B1 | 5/2005 | Neiderman |
| 6,918,541 B2 | 7/2005 | Knowles |
| 6,920,197 B2 | 7/2005 | Kang |
| 6,922,461 B2 | 7/2005 | Kang |
| 6,924,487 B2 | 8/2005 | Bolozdynya |
| 6,928,141 B2 | 8/2005 | Carver |
| 6,936,828 B2 | 8/2005 | Saccomanno |
| 6,937,692 B2 | 8/2005 | Johnson |
| 6,938,488 B2 | 9/2005 | Diaz |
| 6,940,943 B2 | 9/2005 | Claus |
| 6,950,492 B2 | 9/2005 | Besson |
| 6,952,163 B2 | 10/2005 | Huey |
| 6,970,531 B2 | 11/2005 | Eberhard |
| 6,972,693 B2 | 12/2005 | Brown |
| 6,980,681 B1 | 12/2005 | Hsieh |
| 6,982,643 B2 | 1/2006 | Garfinkle |
| 6,990,171 B2 | 1/2006 | Toth |
| 6,998,617 B2 | 2/2006 | DEmilio |
| 7,000,827 B2 | 2/2006 | Meder |
| 7,005,982 B1 | 2/2006 | Frank |
| 7,012,256 B1 | 3/2006 | Roos |
| 7,020,241 B2 | 3/2006 | Beneke |
| 7,026,944 B2 | 4/2006 | Alioto |
| 7,030,755 B2 | 4/2006 | Bohinc, Jr. |
| 7,043,474 B2 | 5/2006 | Mojsilovic |
| 7,045,787 B1 | 5/2006 | Verbinski |
| 7,046,761 B2 | 5/2006 | Ellenbogen |
| 7,046,768 B1 | 5/2006 | Gilevich |
| 7,050,616 B2 | 5/2006 | Hsieh |
| 7,062,074 B1 | 6/2006 | Beneke |
| 7,064,336 B2 | 6/2006 | Archer |
| 7,065,175 B2 | 6/2006 | Green |
| 7,068,751 B2 | 6/2006 | Toth |
| 7,072,434 B1 | 7/2006 | Tybinkowski |
| 7,092,485 B2 | 8/2006 | Kravis |
| 7,098,461 B2 | 8/2006 | Endo |
| 7,099,004 B2 | 8/2006 | Masten |
| 7,099,432 B2 | 8/2006 | Ichihara |
| 7,100,165 B2 | 8/2006 | Eldridge |
| 7,103,137 B2 | 9/2006 | Seppi |
| 7,105,828 B2 | 9/2006 | Unger |
| 7,115,875 B1 | 10/2006 | Worstell |
| 7,116,235 B2 | 10/2006 | Alioto |
| 7,116,749 B2 | 10/2006 | Besson |
| 7,130,456 B2 | 10/2006 | Hillmann |
| 7,136,716 B2 | 11/2006 | Hsiung |
| 7,139,406 B2 | 11/2006 | McClelland |
| 7,142,109 B1 | 11/2006 | Frank |
| 7,142,633 B2 | 11/2006 | Eberhard |
| 7,151,447 B1 | 12/2006 | Willms |
| 7,154,650 B2 | 12/2006 | Lettington |
| 7,164,138 B2 | 1/2007 | McGregor |
| 7,164,750 B2 | 1/2007 | Nabors |
| 7,183,554 B2 | 2/2007 | Gallagher |
| 7,183,906 B2 | 2/2007 | Zanovitch |
| 7,193,515 B1 | 3/2007 | Roberts |
| 7,203,276 B2 | 4/2007 | Arsenault |
| 7,204,125 B2 | 4/2007 | Fine |
| 7,207,713 B2 | 4/2007 | Lowman |
| 7,212,113 B2 | 5/2007 | Zanovitch |
| 7,212,661 B2 | 5/2007 | Samara |
| 7,215,738 B2 | 5/2007 | Muenchau |
| 7,233,644 B1 | 6/2007 | Bendahan |
| 7,233,682 B2 | 6/2007 | Levine |
| 7,244,941 B2 | 7/2007 | Roos |
| 7,257,189 B2 | 8/2007 | Modica |
| 7,269,527 B1 | 9/2007 | Frank |
| 7,322,745 B2 | 1/2008 | Agrawal |
| 7,324,921 B2 | 1/2008 | Sugahara |
| 7,356,115 B2 | 4/2008 | Ford |
| 7,356,174 B2 | 4/2008 | Leue |
| 7,366,282 B2 | 4/2008 | Peschmann |
| 7,369,643 B2 | 5/2008 | Kotowski |
| 7,379,530 B2 | 5/2008 | Hoff |
| 7,391,028 B1 | 6/2008 | Rubenstein |
| 7,397,891 B2 | 7/2008 | Johnson |
| 7,400,701 B1 | 7/2008 | Cason |
| 7,411,198 B1 | 8/2008 | Holland |
| 7,417,440 B2 | 8/2008 | Peschmann |
| 7,418,077 B2 | 8/2008 | Gray |
| 7,430,479 B1 | 9/2008 | Holslin |
| 7,453,987 B1 | 11/2008 | Richardson |
| 7,471,764 B2 | 12/2008 | Kaval |

(56) References Cited

U.S. PATENT DOCUMENTS

| | | |
|---|---|---|
| 7,483,510 B2 | 1/2009 | Carver |
| 7,486,768 B2 | 2/2009 | Allman |
| 7,517,149 B2 | 4/2009 | Agrawal |
| 7,519,148 B2 | 4/2009 | Kotowski |
| 7,525,101 B2 | 4/2009 | Grodzins |
| 7,526,064 B2 | 4/2009 | Akery |
| 7,529,341 B2 | 5/2009 | Schlomka |
| 7,550,738 B1 | 6/2009 | DeVito |
| 7,579,845 B2 | 8/2009 | Peschmann |
| 7,592,601 B2 | 9/2009 | Frank |
| 7,660,388 B2 | 2/2010 | Gray |
| 7,720,194 B2 | 5/2010 | Connelly |
| 7,720,195 B2 | 5/2010 | Allman |
| 7,734,066 B2 | 6/2010 | Delia |
| 7,734,102 B2 | 6/2010 | Bergeron |
| 7,742,568 B2 | 6/2010 | Smith |
| 7,759,649 B2 | 7/2010 | Frank |
| 7,769,132 B1 | 8/2010 | Hurd |
| 7,769,133 B2 | 8/2010 | Carver |
| 7,783,004 B2 | 8/2010 | Kotowski |
| 7,783,005 B2 | 8/2010 | Kaval |
| 7,792,248 B2 | 9/2010 | Strecker |
| 7,813,540 B1 | 10/2010 | Kraft |
| 7,817,776 B2 | 10/2010 | Agrawal |
| 7,851,766 B2 | 12/2010 | Frank |
| 7,856,081 B2 | 12/2010 | Peschmann |
| 7,860,213 B2 | 12/2010 | Akery |
| 7,876,879 B2 | 1/2011 | Morton |
| 7,876,880 B2 | 1/2011 | Kotowski |
| 7,899,232 B2 | 3/2011 | Gudmundson |
| 7,915,596 B2 | 3/2011 | Clothier |
| 7,928,400 B1 | 4/2011 | Diawara |
| 7,963,695 B2 | 6/2011 | Kotowski |
| 7,973,697 B2 | 7/2011 | Reilly |
| 7,982,191 B2 | 7/2011 | Friedman |
| 7,991,133 B2 | 8/2011 | Mills |
| 7,995,705 B2 | 8/2011 | Allman |
| 8,054,938 B2 | 11/2011 | Kaval |
| 8,059,781 B2 | 11/2011 | Agrawal |
| 8,073,099 B2 | 12/2011 | Niu |
| 8,135,110 B2 | 3/2012 | Morton |
| 8,138,770 B2 | 3/2012 | Peschmann |
| 8,170,177 B2 | 5/2012 | Akery |
| 8,173,970 B2 | 5/2012 | Inbar |
| 8,243,167 B2 * | 8/2012 | Liang ............... G06K 9/4614 348/208.6 |
| 8,243,876 B2 | 8/2012 | Morton |
| 8,275,091 B2 | 9/2012 | Morton |
| 8,304,740 B1 | 11/2012 | Frank |
| 8,356,937 B2 | 1/2013 | Kotowski |
| 8,385,501 B2 | 2/2013 | Allman |
| 8,389,942 B2 | 3/2013 | Morton |
| 8,428,217 B2 | 4/2013 | Peschmann |
| 8,433,036 B2 | 4/2013 | Morton |
| 8,457,275 B2 | 6/2013 | Akery |
| 8,472,583 B2 * | 6/2013 | Star-Lack ............. G01V 5/005 378/4 |
| 8,483,356 B2 | 7/2013 | Bendahan |
| 8,491,189 B2 | 7/2013 | Kotowski |
| 8,503,605 B2 | 8/2013 | Morton |
| 8,579,506 B2 | 11/2013 | Morton |
| 8,644,453 B2 | 2/2014 | Morton |
| 8,668,386 B2 | 3/2014 | Morton |
| 8,674,706 B2 | 3/2014 | Peschmann |
| 8,687,765 B2 | 4/2014 | Kotowski |
| 8,735,833 B2 | 5/2014 | Morto |
| 8,750,452 B2 | 6/2014 | Kaval |
| 8,774,357 B2 | 7/2014 | Morton |
| 8,798,232 B2 | 8/2014 | Bendahan |
| 8,831,176 B2 | 9/2014 | Morto |
| 8,837,670 B2 | 9/2014 | Akery |
| 8,840,303 B2 | 9/2014 | Morton |
| 8,908,831 B2 | 12/2014 | Bendahan |
| 8,929,509 B2 | 1/2015 | Morton |
| 8,958,526 B2 | 2/2015 | Morton |
| 8,971,485 B2 | 3/2015 | Morton |
| 8,993,970 B2 | 3/2015 | Morton |
| 9,020,095 B2 | 4/2015 | Morton |
| 9,020,096 B2 | 4/2015 | Allman |
| 9,025,731 B2 | 5/2015 | Kotowski |
| 9,042,511 B2 | 5/2015 | Peschmann |
| 9,052,403 B2 | 6/2015 | Morton |
| 9,057,679 B2 | 6/2015 | Morton |
| 9,086,497 B2 | 7/2015 | Bendahan |
| 9,111,331 B2 | 8/2015 | Parikh |
| 9,121,958 B2 | 9/2015 | Morton |
| 9,158,027 B2 | 10/2015 | Morton |
| 9,218,933 B2 | 12/2015 | Langeveld |
| 9,223,049 B2 | 12/2015 | Kotowski |
| 9,223,050 B2 | 12/2015 | Kaval |
| 9,223,052 B2 | 12/2015 | Morton |
| 9,268,058 B2 | 2/2016 | Peschmann |
| 9,274,065 B2 | 3/2016 | Morton |
| 9,279,901 B2 | 3/2016 | Akery |
| 9,285,498 B2 | 3/2016 | Carver |
| 9,310,322 B2 | 4/2016 | Panesar |
| 9,310,323 B2 | 4/2016 | Bendahan |
| 9,316,760 B2 | 4/2016 | Bendahan |
| 9,329,285 B2 | 5/2016 | Gozani |
| 9,332,624 B2 | 5/2016 | Morton |
| 2001/0016030 A1 | 8/2001 | Nicolas |
| 2001/0021013 A1 | 9/2001 | Hecht |
| 2001/0021244 A1 | 9/2001 | Suzuki |
| 2001/0028696 A1 | 10/2001 | Yamada |
| 2001/0033636 A1 | 10/2001 | Hartick |
| 2001/0038681 A1 | 11/2001 | Stanton |
| 2001/0038705 A1 | 11/2001 | Rubbert |
| 2001/0038707 A1 | 11/2001 | Ohara |
| 2001/0048734 A1 | 12/2001 | Uppaluri |
| 2001/0053197 A1 | 12/2001 | Murayama |
| 2002/0001366 A1 | 1/2002 | Tamura |
| 2002/0015475 A1 | 2/2002 | Matsumoto |
| 2002/0016546 A1 | 2/2002 | Cerofolini |
| 2002/0017620 A1 | 2/2002 | Oomori |
| 2002/0018199 A1 | 2/2002 | Blumenfeld |
| 2002/0024016 A1 | 2/2002 | Endo |
| 2002/0027970 A1 | 3/2002 | Chapman |
| 2002/0028994 A1 | 3/2002 | Kamiyama |
| 2002/0031246 A1 | 3/2002 | Kawano |
| 2002/0037068 A1 | 3/2002 | Oikawa |
| 2002/0044691 A1 | 4/2002 | Matsugu |
| 2002/0049660 A1 | 4/2002 | Obrador |
| 2002/0054694 A1 | 5/2002 | Vachtsevanos |
| 2002/0067259 A1 | 6/2002 | Fufidio |
| 2002/0067793 A1 | 6/2002 | Stierstorfer |
| 2002/0085046 A1 | 7/2002 | Furuta |
| 2002/0088952 A1 | 7/2002 | Rao |
| 2002/0094062 A1 | 7/2002 | Dolazza |
| 2002/0094064 A1 | 7/2002 | Zhou |
| 2002/0094119 A1 | 7/2002 | Sahadevan |
| 2002/0098518 A1 | 7/2002 | Levinson |
| 2002/0106052 A1 | 8/2002 | Menhardt |
| 2002/0122528 A1 | 9/2002 | Besson |
| 2002/0124664 A1 | 9/2002 | Call |
| 2002/0126800 A1 | 9/2002 | Matsumoto |
| 2002/0127586 A1 | 9/2002 | Mortensen |
| 2002/0141625 A1 | 10/2002 | Nelson |
| 2002/0150200 A1 | 10/2002 | Zonneveld |
| 2002/0161534 A1 | 10/2002 | Adler |
| 2002/0168083 A1 | 11/2002 | Garms |
| 2002/0168657 A1 | 11/2002 | Chen |
| 2002/0172324 A1 | 11/2002 | Ellengogen |
| 2002/0172409 A1 | 11/2002 | Saito |
| 2002/0175291 A1 | 11/2002 | Reeder |
| 2002/0175921 A1 | 11/2002 | Xu |
| 2002/0176351 A1 | 11/2002 | Masaki |
| 2002/0176534 A1 | 11/2002 | Meder |
| 2002/0186862 A1 | 12/2002 | McClelland |
| 2002/0188197 A1 | 12/2002 | Bishop |
| 2002/0191209 A1 | 12/2002 | Yasumaru |
| 2002/0198731 A1 | 12/2002 | Barnes |
| 2003/0012420 A1 | 1/2003 | Verwoerd |
| 2003/0023469 A1 | 1/2003 | Lee |
| 2003/0023592 A1 | 1/2003 | Modica |

(56) References Cited

U.S. PATENT DOCUMENTS

| | | |
|---|---|---|
| 2003/0024315 A1 | 2/2003 | Merkel |
| 2003/0031289 A1 | 2/2003 | Hsieh |
| 2003/0031291 A1 | 2/2003 | Yamamoto |
| 2003/0036006 A1 | 2/2003 | Feke |
| 2003/0038945 A1 | 2/2003 | Mahner |
| 2003/0043964 A1 | 3/2003 | Sorenson |
| 2003/0068557 A1 | 4/2003 | Kumashiro |
| 2003/0072414 A1 | 4/2003 | Sakaida |
| 2003/0072418 A1 | 4/2003 | Albagli |
| 2003/0072484 A1 | 4/2003 | Kokko |
| 2003/0076924 A1 | 4/2003 | Mario |
| 2003/0081720 A1 | 5/2003 | Swift |
| 2003/0081859 A1 | 5/2003 | Kasutani |
| 2003/0082516 A1 | 5/2003 | Straus |
| 2003/0085163 A1 | 5/2003 | Chan |
| 2003/0085348 A1 | 5/2003 | Megerle |
| 2003/0085353 A1 | 5/2003 | Almogy |
| 2003/0091145 A1 | 5/2003 | Mohr |
| 2003/0095633 A1 | 5/2003 | VanWoezik |
| 2003/0095692 A1 | 5/2003 | Mundy |
| 2003/0108150 A1 | 6/2003 | Franke |
| 2003/0128812 A1 | 7/2003 | Appleby |
| 2003/0138147 A1 | 7/2003 | Ongkojoyo |
| 2003/0144800 A1 | 7/2003 | Davis |
| 2003/0148393 A1 | 8/2003 | Woodbury |
| 2003/0149346 A1 | 8/2003 | Arnone |
| 2003/0165213 A1 | 9/2003 | Maglich |
| 2003/0179853 A1 | 9/2003 | Amemiya |
| 2003/0194121 A1 | 10/2003 | Eberhard |
| 2003/0201394 A1 | 10/2003 | Peoples |
| 2003/0205676 A1 | 11/2003 | Nelson |
| 2003/0206649 A1 | 11/2003 | Moshe |
| 2003/0210139 A1 | 11/2003 | Brooks |
| 2003/0215051 A1 | 11/2003 | Suzuki |
| 2003/0215054 A1 | 11/2003 | Fenkart |
| 2003/0215143 A1 | 11/2003 | Zakrzewski |
| 2003/0231788 A1 | 12/2003 | Yukhin |
| 2003/0231791 A1 | 12/2003 | Torre-Bueno |
| 2004/0012853 A1 | 1/2004 | Garcia |
| 2004/0013239 A1 | 1/2004 | Gregerson |
| 2004/0016271 A1 | 1/2004 | Shah |
| 2004/0017882 A1 | 1/2004 | Misawa |
| 2004/0017883 A1 | 1/2004 | Takagi |
| 2004/0017888 A1 | 1/2004 | Seppi |
| 2004/0017935 A1 | 1/2004 | Avinash |
| 2004/0022425 A1 | 2/2004 | Avinash |
| 2004/0027127 A1 | 2/2004 | Mills |
| 2004/0037462 A1 | 2/2004 | Lewis |
| 2004/0041082 A1 | 3/2004 | Harmon |
| 2004/0051030 A1 | 3/2004 | Olszak |
| 2004/0051265 A1 | 3/2004 | Nadeau |
| 2004/0062342 A1 | 4/2004 | Cahill |
| 2004/0062349 A1 | 4/2004 | Schuster |
| 2004/0062351 A1 | 4/2004 | Yoshioka |
| 2004/0066882 A1 | 4/2004 | Eberhard |
| 2004/0066884 A1 | 4/2004 | HermannClaus |
| 2004/0066890 A1 | 4/2004 | Dalmijn |
| 2004/0075058 A1 | 4/2004 | Blevis |
| 2004/0080315 A1 | 4/2004 | Beevor |
| 2004/0082846 A1 | 4/2004 | Johnson |
| 2004/0083958 A1 | 5/2004 | Saidman |
| 2004/0086075 A1 | 5/2004 | Hein |
| 2004/0086078 A1 | 5/2004 | Adams |
| 2004/0086160 A1 | 5/2004 | Zimmermann |
| 2004/0087844 A1 | 5/2004 | Yen |
| 2004/0101097 A1 | 5/2004 | Wakayama |
| 2004/0101098 A1 | 5/2004 | Bijjani |
| 2004/0102700 A1 | 5/2004 | Asafusa |
| 2004/0109231 A1 | 6/2004 | Haisch |
| 2004/0119591 A1 | 6/2004 | Peeters |
| 2004/0120009 A1 | 6/2004 | White |
| 2004/0120454 A1 | 6/2004 | Ellenbogen |
| 2004/0120857 A1 | 6/2004 | Smith |
| 2004/0126895 A1 | 7/2004 | Overbeck |
| 2004/0134986 A1 | 7/2004 | Studer |
| 2004/0141056 A1 | 7/2004 | Izumi |
| 2004/0141584 A1 | 7/2004 | Bernardi |
| 2004/0142386 A1 | 7/2004 | Rigler |
| 2004/0148137 A1 | 7/2004 | Zerwekh |
| 2004/0160599 A1 | 8/2004 | Hamamatsu |
| 2004/0161073 A1 | 8/2004 | Nokita |
| 2004/0175041 A1 | 9/2004 | Miller |
| 2004/0176677 A1 | 9/2004 | Hwu |
| 2004/0179647 A1 | 9/2004 | Zhao |
| 2004/0202154 A1 | 10/2004 | Aklepi |
| 2004/0212492 A1 | 10/2004 | Boesch |
| 2004/0212499 A1 | 10/2004 | Bohinc |
| 2004/0213377 A1 | 10/2004 | Endo |
| 2004/0213600 A1 | 10/2004 | Watanabe |
| 2004/0218729 A1 | 11/2004 | Xue |
| 2004/0225222 A1 | 11/2004 | Zeng |
| 2004/0232054 A1 | 11/2004 | Brown |
| 2004/0236520 A1 | 11/2004 | Williams |
| 2004/0240612 A1 | 12/2004 | Suzuki |
| 2004/0247071 A1 | 12/2004 | Dafni |
| 2004/0247171 A1 | 12/2004 | Hashimoto |
| 2004/0251415 A1 | 12/2004 | Verbinski |
| 2004/0252024 A1 | 12/2004 | Huey |
| 2004/0252870 A1 | 12/2004 | Reeves |
| 2004/0253660 A1 | 12/2004 | Gibbs |
| 2004/0256565 A1 | 12/2004 | Adams |
| 2004/0258198 A1 | 12/2004 | Carver |
| 2004/0258202 A1 | 12/2004 | Wernick |
| 2004/0263379 A1 | 12/2004 | Keller |
| 2004/0264624 A1 | 12/2004 | Tanaka |
| 2004/0264648 A1 | 12/2004 | Claus |
| 2004/0265175 A1 | 12/2004 | Witty |
| 2005/0001728 A1 | 1/2005 | Appelt |
| 2005/0008119 A1 | 1/2005 | McClelland |
| 2005/0008203 A1 | 1/2005 | Dixon |
| 2005/0011849 A1 | 1/2005 | Chattey |
| 2005/0017181 A1 | 1/2005 | Kearfott |
| 2005/0018812 A1 | 1/2005 | Wolfs |
| 2005/0023477 A1 | 2/2005 | Archer |
| 2005/0023479 A1 | 2/2005 | Grodzins |
| 2005/0024199 A1 | 2/2005 | Huey |
| 2005/0025280 A1 | 2/2005 | Schulte |
| 2005/0025350 A1 | 2/2005 | Engelbart |
| 2005/0025377 A1 | 2/2005 | Avinash |
| 2005/0029460 A1 | 2/2005 | Iwatschenko-Borho |
| 2005/0031069 A1 | 2/2005 | Kaucic |
| 2005/0031076 A1 | 2/2005 | McClelland |
| 2005/0053307 A1 | 3/2005 | Nose |
| 2005/0057354 A1 | 3/2005 | Jenkins |
| 2005/0058242 A1 | 3/2005 | Peschmann |
| 2005/0058350 A1 | 3/2005 | Dugan |
| 2005/0061955 A1 | 3/2005 | Endo |
| 2005/0069085 A1 | 3/2005 | Lewis |
| 2005/0074088 A1 | 4/2005 | Ichihara |
| 2005/0085721 A1 | 4/2005 | Fauver |
| 2005/0094856 A1 | 5/2005 | Warren |
| 2005/0098728 A1 | 5/2005 | Alfano |
| 2005/0100135 A1 | 5/2005 | Lowman |
| 2005/0105665 A1 | 5/2005 | Grodzins |
| 2005/0105680 A1 | 5/2005 | Nabors |
| 2005/0110672 A1 | 5/2005 | Cardiasmenos |
| 2005/0111618 A1 | 5/2005 | Sommer |
| 2005/0113961 A1 | 5/2005 | Sabol |
| 2005/0117683 A1 | 6/2005 | Mishin |
| 2005/0117693 A1 | 6/2005 | Miyano |
| 2005/0117700 A1 | 6/2005 | Peschmann |
| 2005/0123093 A1 | 6/2005 | Lawaczeck |
| 2005/0123174 A1 | 6/2005 | Gorsky |
| 2005/0128069 A1 | 6/2005 | Skatter |
| 2005/0133708 A1 | 6/2005 | Eberhard |
| 2005/0135535 A1 | 6/2005 | Wallace |
| 2005/0135668 A1 | 6/2005 | Polichar |
| 2005/0147199 A1 | 7/2005 | Dunham |
| 2005/0153356 A1 | 7/2005 | Okawa |
| 2005/0156734 A1 | 7/2005 | Zerwekh |
| 2005/0157842 A1 | 7/2005 | Agrawal |
| 2005/0157844 A1 | 7/2005 | Bernardi |
| 2005/0163354 A1 | 7/2005 | Ziegler |
| 2005/0169421 A1 | 8/2005 | Muenchau |

(56) References Cited

U.S. PATENT DOCUMENTS

| | | |
|---|---|---|
| 2005/0173284 A1 | 8/2005 | Ambrefe |
| 2005/0189412 A1 | 9/2005 | Hudnut |
| 2005/0190882 A1 | 9/2005 | McGuire |
| 2005/0198226 A1 | 9/2005 | Delia |
| 2005/0205793 A1 | 9/2005 | Bohinc |
| 2005/0206514 A1 | 9/2005 | Zanovitch |
| 2005/0207655 A1 | 9/2005 | Chopra |
| 2005/0212913 A1 | 9/2005 | Richter |
| 2005/0219523 A1 | 10/2005 | Onuma |
| 2005/0220247 A1 | 10/2005 | Ruddy |
| 2005/0220264 A1 | 10/2005 | Homegger |
| 2005/0224719 A1 | 10/2005 | Polichar |
| 2005/0226375 A1 | 10/2005 | Eberhard |
| 2005/0240858 A1 | 10/2005 | Croft |
| 2005/0248450 A1 | 11/2005 | Zanovitch |
| 2005/0249416 A1 | 11/2005 | Leue |
| 2005/0251397 A1 | 11/2005 | Zanovitch |
| 2005/0251398 A1 | 11/2005 | Zanovitch |
| 2005/0258372 A1 | 11/2005 | McGregor |
| 2005/0259868 A1 | 11/2005 | Sones |
| 2005/0265517 A1 | 12/2005 | Gary |
| 2005/0271184 A1 | 12/2005 | Ovadia |
| 2005/0275545 A1 | 12/2005 | Alioto |
| 2005/0275831 A1 | 12/2005 | Silver |
| 2005/0276443 A1 | 12/2005 | Slamani |
| 2005/0279936 A1 | 12/2005 | Litman |
| 2005/0283079 A1 | 12/2005 | Steen |
| 2006/0000911 A1 | 1/2006 | Stekel |
| 2006/0002504 A1 | 1/2006 | DeMan |
| 2006/0008054 A1 | 1/2006 | Ohara |
| 2006/0009269 A1 | 1/2006 | Hoskinson |
| 2006/0013455 A1 | 1/2006 | Watson |
| 2006/0013464 A1 | 1/2006 | Ramsay |
| 2006/0017605 A1 | 1/2006 | Lovberg |
| 2006/0018434 A1 | 1/2006 | Jacobs |
| 2006/0018517 A1 | 1/2006 | Chen |
| 2006/0019409 A1 | 1/2006 | Nelson |
| 2006/0027751 A1 | 2/2006 | Kurita |
| 2006/0034503 A1 | 2/2006 | Shimayama |
| 2006/0036167 A1 | 2/2006 | Shina |
| 2006/0045235 A1 | 3/2006 | Bruder |
| 2006/0045323 A1 | 3/2006 | Ateya |
| 2006/0056584 A1 | 3/2006 | Allman |
| 2006/0064246 A1 | 3/2006 | Medberry |
| 2006/0065844 A1 | 3/2006 | Zelakiewicz |
| 2006/0072702 A1 | 4/2006 | Chapman |
| 2006/0083418 A1 | 4/2006 | Watson |
| 2006/0084872 A1 | 4/2006 | Ichikawa |
| 2006/0086794 A1 | 4/2006 | Knowles |
| 2006/0093088 A1 | 5/2006 | Sowerby |
| 2006/0097171 A1 | 5/2006 | Balchunas |
| 2006/0098773 A1 | 5/2006 | Peschmann |
| 2006/0098842 A1 | 5/2006 | Levine |
| 2006/0098866 A1 | 5/2006 | Whitson |
| 2006/0109949 A1 | 5/2006 | Tkaczyk |
| 2006/0114477 A1 | 6/2006 | Cox |
| 2006/0115044 A1 | 6/2006 | Wu |
| 2006/0115109 A1 | 6/2006 | Whitson |
| 2006/0116566 A1 | 6/2006 | Bruijns |
| 2006/0119837 A1 | 6/2006 | Raguin |
| 2006/0133650 A1 | 6/2006 | Xie |
| 2006/0133659 A1 | 6/2006 | Hammond |
| 2006/0138331 A1 | 6/2006 | Guillebaud |
| 2006/0140341 A1 | 6/2006 | Carver |
| 2006/0141615 A1 | 6/2006 | Lu |
| 2006/0142662 A1 | 6/2006 | VanBeek |
| 2006/0142984 A1 | 6/2006 | Weese |
| 2006/0173268 A1 | 8/2006 | Mullick |
| 2006/0176062 A1 | 8/2006 | Yang |
| 2006/0182221 A1 | 8/2006 | Bernhardt |
| 2006/0203960 A1 | 9/2006 | Schlomka |
| 2006/0204080 A1 | 9/2006 | Sones |
| 2006/0215811 A1 | 9/2006 | Modica |
| 2006/0249685 A1 | 11/2006 | Tanaka |
| 2006/0255929 A1 | 11/2006 | Zanovitch |
| 2006/0257005 A1 | 11/2006 | Bergeron |
| 2006/0262902 A1 | 11/2006 | Wattenburg |
| 2006/0269135 A1 | 11/2006 | Ramsay |
| 2006/0273257 A1 | 12/2006 | Roos |
| 2006/0274916 A1 | 12/2006 | Chan |
| 2006/0282886 A1 | 12/2006 | Gaug |
| 2006/0284094 A1 | 12/2006 | Inbar |
| 2007/0001123 A1 | 1/2007 | Andrews |
| 2007/0003122 A1 | 1/2007 | Sirohey |
| 2007/0058037 A1 | 3/2007 | Bergeron |
| 2007/0083414 A1 | 4/2007 | Krohn |
| 2007/0085010 A1 | 4/2007 | Letant |
| 2007/0118399 A1 | 5/2007 | Avinash |
| 2007/0140423 A1 | 6/2007 | Foland |
| 2007/0147585 A1 | 6/2007 | Eilbert |
| 2007/0156281 A1 | 7/2007 | Leung |
| 2007/0165777 A1 | 7/2007 | Anwar |
| 2007/0168467 A1 | 7/2007 | Hu |
| 2007/0172129 A1 | 7/2007 | Tortora |
| 2007/0189454 A1 | 8/2007 | Georgeson |
| 2007/0194909 A1 | 8/2007 | Garfield |
| 2007/0195994 A1 | 8/2007 | McClelland |
| 2007/0200566 A1 | 8/2007 | Clark |
| 2007/0206719 A1 | 9/2007 | Suryanarayanan |
| 2007/0210255 A1 | 9/2007 | Bjorkholm |
| 2007/0210921 A1 | 9/2007 | Volpi |
| 2007/0228284 A1 | 10/2007 | Polichar |
| 2007/0237293 A1 | 10/2007 | Singh |
| 2007/0269005 A1 | 11/2007 | Chalmers |
| 2007/0280502 A1 | 12/2007 | Paresi |
| 2007/0290136 A1 | 12/2007 | Ivan |
| 2008/0023631 A1 | 1/2008 | Majors |
| 2008/0037707 A1 | 2/2008 | Rothschild |
| 2008/0048872 A1 | 2/2008 | Frank |
| 2008/0075230 A1 | 3/2008 | Oreper |
| 2008/0084963 A1 | 4/2008 | Clayton |
| 2008/0118021 A1 | 5/2008 | Dutta |
| 2008/0128624 A1 | 6/2008 | Cooke |
| 2008/0152082 A1 | 6/2008 | Bouchard |
| 2008/0159591 A1 | 7/2008 | Ruedin |
| 2008/0170670 A1 | 7/2008 | Bhatt |
| 2008/0198967 A1 | 8/2008 | Connelly |
| 2008/0198970 A1 | 8/2008 | Kirshner |
| 2008/0205594 A1 | 8/2008 | Bjorkholm |
| 2008/0230709 A1 | 9/2008 | Tkaczyk |
| 2008/0236275 A1 | 10/2008 | Breed |
| 2008/0253653 A1 | 10/2008 | Gable |
| 2008/0260097 A1 | 10/2008 | Anwar |
| 2008/0304622 A1 | 12/2008 | Morton |
| 2009/0014662 A1 | 1/2009 | Suhami |
| 2009/0034790 A1 | 2/2009 | Song |
| 2009/0067575 A1 | 3/2009 | Seppi |
| 2009/0086907 A1 | 4/2009 | Smith |
| 2009/0116617 A1 | 5/2009 | Mastronardi |
| 2009/0127459 A1 | 5/2009 | Neustadter |
| 2009/0168964 A1 | 7/2009 | Safai |
| 2009/0174554 A1 | 7/2009 | Bergeron |
| 2009/0236531 A1 | 9/2009 | Frank |
| 2009/0238336 A1 | 9/2009 | Akery |
| 2009/0245462 A1 | 10/2009 | Agrawal |
| 2009/0257555 A1 | 10/2009 | Chalmers |
| 2009/0283690 A1* | 11/2009 | Bendahan ............ G01V 5/0033 250/390.01 |
| 2009/0285353 A1 | 11/2009 | Ellenbogen |
| 2009/0316851 A1 | 12/2009 | Oosaka |
| 2009/0323894 A1 | 12/2009 | Hu |
| 2010/0020937 A1 | 1/2010 | Hautmann |
| 2010/0161504 A1 | 6/2010 | Casey |
| 2010/0177868 A1 | 7/2010 | Smith |
| 2010/0177873 A1 | 7/2010 | Chen |
| 2010/0295689 A1 | 11/2010 | Armistead |
| 2011/0019797 A1 | 1/2011 | Morton |
| 2011/0019799 A1 | 1/2011 | Shedlock |
| 2011/0038453 A1 | 2/2011 | Morton |
| 2011/0060426 A1 | 3/2011 | Morton |
| 2011/0064192 A1 | 3/2011 | Morton |
| 2011/0075808 A1 | 3/2011 | Rothschild |
| 2011/0172972 A1 | 7/2011 | Gudmundson |
| 2011/0204243 A1 | 8/2011 | Bendahan |

(56) References Cited

U.S. PATENT DOCUMENTS

| | | |
|---|---|---|
| 2011/0235777 A1 | 9/2011 | Gozani |
| 2011/0266643 A1 | 11/2011 | Engelmann |
| 2012/0093367 A1 | 4/2012 | Gudmundson |
| 2012/0099710 A1 | 4/2012 | Kotowski |
| 2012/0104276 A1 | 5/2012 | Miller |
| 2012/0105267 A1 | 5/2012 | DeLia |
| 2012/0116720 A1 | 5/2012 | Klann |
| 2013/0001048 A1 | 1/2013 | Panesar |
| 2014/0185771 A1 | 7/2014 | Morton |
| 2014/0197321 A1 | 7/2014 | Bendahan |
| 2015/0036798 A1 | 2/2015 | Morton |
| 2015/0078519 A1 | 3/2015 | Morton |
| 2015/0301220 A1 | 10/2015 | Morton |
| 2015/0325010 A1 | 11/2015 | Bedford |
| 2015/0355117 A1 | 12/2015 | Morton |
| 2015/0355369 A1 | 12/2015 | Morton |
| 2016/0025889 A1 | 1/2016 | Morton |
| 2016/0033674 A1 | 2/2016 | Allman |

FOREIGN PATENT DOCUMENTS

| | | |
|---|---|---|
| CA | 2307439 C | 7/2008 |
| CN | 101303317 A | 11/2008 |
| EP | 0077018 A1 | 4/1983 |
| EP | 0455177 A2 | 11/1991 |
| EP | 0459648 A1 | 12/1991 |
| EP | 0577380 A1 | 1/1994 |
| EP | 0919186 A2 | 6/1999 |
| EP | 1413898 A1 | 4/2004 |
| EP | 2270547 | 1/2011 |
| GB | 2158572 A | 11/1985 |
| GB | 2255634 A | 11/1992 |
| GB | 2110037 A | 6/1993 |
| GB | 2277013 A | 10/1994 |
| GB | 2368764 A | 5/2002 |
| GB | 2409268 A | 6/2005 |
| GB | 2424065 A | 9/2006 |
| GB | 2438317 A | 11/2007 |
| JP | H0422897 A | 1/1992 |
| JP | 2001233440 A | 8/2001 |
| JP | 2003287507 A | 10/2003 |
| JP | 2005257400 | 9/2005 |
| WO | 1992003837 A1 | 3/1992 |
| WO | 9855851 A1 | 12/1998 |
| WO | 2000049428 | 8/2000 |
| WO | 2002082290 A1 | 10/2002 |
| WO | 2003069498 A1 | 8/2003 |
| WO | 2004010127 A1 | 1/2004 |
| WO | 2004010162 A2 | 1/2004 |
| WO | 2003107113 A3 | 5/2004 |
| WO | 2005086616 A2 | 9/2005 |
| WO | 2005098400 A2 | 10/2005 |
| WO | 2006036076 A1 | 4/2006 |
| WO | 2006053279 A2 | 5/2006 |
| WO | 2006078691 A2 | 7/2006 |
| WO | 2006119603 A1 | 11/2006 |
| WO | 2006119605 | 11/2006 |
| WO | 2006119605 A1 | 11/2006 |
| WO | 2007035359 A2 | 3/2007 |
| WO | 2007055720 A2 | 5/2007 |
| WO | 2007068933 A1 | 6/2007 |
| WO | 2007103216 A2 | 9/2007 |
| WO | 2008017983 A2 | 2/2008 |
| WO | 2009106803 A2 | 9/2009 |
| WO | 2009143169 A1 | 11/2009 |
| WO | 2011069024 A1 | 6/2011 |
| WO | 2011091070 A2 | 7/2011 |
| WO | 2013116549 | 8/2013 |
| WO | 2013119423 A1 | 8/2013 |
| WO | 2014107675 | 7/2014 |
| WO | 2014121097 A1 | 8/2014 |
| WO | 2014124152 A2 | 8/2014 |
| WO | 2016011205 | 1/2016 |

OTHER PUBLICATIONS

ClearView Workstation, L3 Security & Detection Systems, Jun. 9, 2011.
Office Action dated Dec. 27, 2017 for U.S. Appl. No. 15/455,436; (pp. 1-28).
International Search Report for PCT/US10/58809; Rapiscan Systems Inc.; dated Apr. 19, 2011.
Mobile X-Ray Inspection Systems, Internet Citation, Feb. 12, 2007, pp. 1-2, URL:http://web.archive.org/web/20070212000928/http://www.bombdetecti-on.com/cat--details.php?catid=20.
Molchanov P A et al: 'Nanosecond gated optical sensors for ocean optic applications' Sensors Applications Symposium, 2006. Proceedings of the 2006 IEEE Houston, Texas,USA Feb. 7-9, 2006, Piscataway, NJ, USA,IEEE, Feb. 7, 2006 (Feb. 7, 2006), pp. 147-150, XP010917671 ISBN: 978-0-7803-9580-0.
Smith C. R. et al: 'Application of 450 kV computed tomography to engine blocks with steel liners' Materials Evaluation vol. 65, No. 5, 2007, pp. 458-461, XP055108238.
CRS Report for Congress, Aviation Security Technologies and Procedures: Screening Passengers and Baggage, Oct. 26, 2001, pp. 1-12.
Written Opinion on Patentability for PCT/US11/21758; dated Jul. 7, 2011; Rapiscan Systems.
International Search Report and Written Opinion for PCT/US12/54110, dated Dec. 24, 2012.
International Search Report for PCT/US11/21758; dated Jul. 7, 2011, Rapiscan Systems Inc.
International Search Report for PCT/US13/24191, Rapiscan Systems Inc., dated Jun. 25, 2013.
Written Opinion of the International Searching Authority for PCT/US2014/015126, dated May 27, 2014.
International Search Report for PCT/US13/23676, dated Jun. 28, 2013.
Notice of Allowance dated Mar. 16, 2015 for U.S. Appl. No. 13/606,442.
International Search Report for PCT/GB2009/000497, dated Jan. 22, 2010.
International Search Report for PCT/US14/56652, dated Apr. 27, 2015.
First Examination Report for Australian Application No. 2012304490, dated Jul. 7, 2014.
International Preliminary Report on Patentability for PCT/US2014/014198, dated Aug. 4, 2015.
International Preliminary Report on Patentability for PCT/US11/21758, dated Jul. 7, 2011.
International Search Report for PCT/US14/14198, dated May 16, 2014.
International Search Report for PCT/US2014/015126, dated May 27, 2014.
International Search Report for PCT/US2015/040653, dated Dec. 16, 2015.
International Search Report for PCT/US2014/010370, dated May 13, 2014.
Supplementary European Search Report for EP12830287, dated Feb. 27, 2015.
Examination Report for GB14049951, dated Jun. 26, 2015.
International Search Report for PCT/GB09/00575, dated Apr. 7, 2010.
First Office Action for Chinese Patent Application No. CN201280054643.3, dated Aug. 27, 2015.
Examination Report for GB14049951, dated Dec. 4, 2015.
Office Action dated Mar. 7, 2016 for U.S. Appl. No. 14/739,329.
Office Action dated May 14, 2014 for U.S. Appl. No. 13/606,442.
"ClearView Workstation Cargo Inspection Workstation," L-3 Communications Security & Detection Systems, Jul. 27, 2011, 2 pages.
Examination Report for EP12830287.4, dated Jan. 18, 2016.
Office Action for JP2014529885, dated Jan. 28, 2016.
Examination Report for EP12830287.4, dated Oct. 31, 2016.
Examination Report for GB14049951, dated Jun. 27, 2016.
Notice of Allowance dated Dec. 12, 2016 for U.S. Appl. No. 14/739,329.
Third Office Action for Chinese Patent Application No.

(56) References Cited

OTHER PUBLICATIONS

CN201280054643.3, dated Nov. 22, 2016.
Office Action dated Jul. 26, 2018 for US Appl. No. 15/455,436 (pp. 1-14).
Notification of Re-Examination for CN201280054643.3, dated Apr. 2018.
Examination Report for 2304/DELNP/2014, dated Apr. 12, 2018.
Notification of Re-Examination for CN201280054643.3, dated Oct. 30, 2018.
Horner et al., "Phase-Only Matched Filtering", Applied Optics, vol. 23, No. 6, Mar. 15, 1994, pp. 812-816.
Mahalanobis, et al. "Minimum Average Correlation Energy Filters", Applied Optics, vol. 26, No. 17, pp. 3633-3640, Sep. 1987.
Kumar et al. "Spatial frequency domain image processing for biometric recognition", Biometrics ICIP Conference 2002.
Caulfield, et al. "Improved Discrimination in Optical Character Recognition", Applied Optics, vol. 8, pp. 2354-2356, Nov. 1969.
Morin, et al. "Optical Character Recognition (OCR) in Uncontrolled Environments Using Optical Correlators", Proc. SPIE Int. Soc. Opt. Eng. 3715, 346; 1999.
International Search Report for PCT/US2012/054110, dated Dec. 24, 2012.
Office Action for Canadian Patent Application No. 2849398, dated Sep. 21, 2018.
Notification of Preliminary Refusal for Korean Patent Application No. 10-2014-70008915, dated Oct. 22, 2018.
Viggo Butler and Robert W. Poole, Jr., Rethinking Checked-Baggage Screening, Reason Public Policy Institute, Policy Study 297, Jul. 2002.
McLay, Laura A., Jacobson, Sheldon H., and Kobza, John E., A multilevel passenger screening problem for aviation security, Naval Research Logistics (NRL), vol. 53, issue 3, pp. 183-197, 2006.
Sun Olapiriyakul and Sanchoy Das, Design and analysis of a two-stage security screening and inspection system, Journal of Air Transport Management, vol. 13, Issue 2, Mar. 2007, pp. 67-74.
Kelly Leone and Rongfang (Rachel) Liu, The key design parameters of checked baggage security screening systems in airports, Journal of Air Transport Management, vol. 11, Issue 2, Mar. 2005, pp. 69-78.
Pre-Examination Report for Brazilian Patent Application No. P1908881-4, dated Nov. 7, 2018.
Summons to attend oral proceedings for EP097149108, dated Jun. 2, 2015.
First Examination Report for Indian Patent Application No. 6409/DELNP/2010, dated Apr. 26, 2017.

\* cited by examiner

| 301 | CERTSCAN INSPECTION STATUS DASHBOARD | | | | 607 |
|---|---|---|---|---|---|
| CONTAINER/IDENTIFIER | SCANNING | SCANNED | ANALYSIS | COMPLETED STATUS | COMMENTS |
| MCCU3746529 | 14:02 | | | | |
| LFE-354 | 13:40 | 13:41 | 13:42 | | 606c |
| HRZU8375274 | 13:35 | 13:36 | 13:38 | 13:38 | |
| MCCU3530682 | 13:33 | 13:35 | 13:36 | 13:37 | |
| MCCU2750385 | 13:28 | 13:29 | 13:30 | 13:41 | 606a |
| JAB-3857 | 13:25 | 13:26 | 13:28 | 13:28 | 606b VISUAL INSPECTION |
| A294837 | 13:23 | 13:24 | 13:24 | 13:27 | 606d |
| HRZS3004728 | 13:20 | 13:21 | 13:24 | 13:25 | CLEARED |
| B847397 | | | | | |

Rapiscan systems
AN OSI SYSTEMS COMPANY

SCREENING SOLUTIONS

PR-4721

| CERTSCAN | COMPLETED SCANS | | | | |
|---|---|---|---|---|---|
| VIEWS | | | | | |
| PENDING SCAN RECORDS | COMPLETE SCANS 901 | | | EXPORT TO EXCEL: 905 | ALL COMPLETE 906 |
| COMPLETED SCAN RECORDS | FILTER BY SHIPPER: 902 | ALL ▼ | APPLY FILTER 903 904 | | |
| ACTIONS | CONTAINER # | SHIPPER | VESSEL NAME | VOYAGE NUMBER | EXPECTED ARRIVAL DATE |
| SET LOCATION | FSCU6537824 | MSEASTAR | BUXFAVOURITE | 1002 | 02/02/2010 |
| SEARCH CONTAINERS | STRU8331814 | MSEASTAR | EL YUNQUE | EY870S | 02/01/2010 |
| | HRZU580059 | MHORIZON | HORIZ CHALLENGER | 503S | 02/05/2010 |
| | HLXU4361153 | MSEASTAR | BUXFAVOURITE | 1002 | 02/02/2010 |
| | TRLU7176489 | MSEASTAR | BUXFAVOURITE | 1002 | 02/02/2010 |
| | HRZU435044 | MHORIZON | HORIZ CHALLENGER | 503S | 02/05/2010 |
| | FCIU8488553 | MSEASTAR | BUXFAVOURITE | 1002 | 02/02/2010 |
| | SOL254153 | MTRAILER | JAX/SJU BRIDGE | 1962 | 02/04/2010 |
| | STRU4886250 | MSEASTAR | EL MORRO | EM940S | 02/05/2010 |

| | Single pallet 4301 | Double pallet 4302 | Measured 4303 |
|---|---|---|---|
| Cargo width (cm) | 190 | 81 / 82 | 99 |
| Cargo height (cm) | 157 | 150 / 162 | 152 |
| Gap between pallets (cm) | - | 30 | |
| Effective Steel density (g/cc) | 0.51 | 0.65 / 0.55 | 0.65 |
| Rms error of fit (g/cm²) | 4.0 | 2.0 | |

FIG. 48

|  | C | H | O | N | C/O | N*O/C^2 |
|---|---|---|---|---|---|---|
| Cocaine | 68.5 | 7.0 | 20.5 | 4.0 | 3.3 | 0.02 |
| C4 | 22 | 4 | 40 | 35 | 0.6 | 2.89 |
| Fish | 19.9 | 10.5 | 66.2 | 3.5 | 0.3 | 0.58 |
| Produce | 5.9 | 10.6 | 83.5 | 0.0 | 0.1 | 0.00 |
| Paper | 47.0 | 6.0 | 44.0 | 0.0 | 1.1 | 0.00 |

4801 — C/O
4802 — N*O/C^2

SYSTEMS AND METHODS FOR DETECTING THREATS AND CONTRABAND IN CARGO

CROSS-REFERENCE

The present specification relies on U.S. Patent Provisional Application No. 62/298,383, entitled "Tanker Content Assessment" and filed on Feb. 22, 2016, for priority.

In addition, the present specification relates to U.S. patent application Ser. No. 14/739,329, entitled "X-Ray Inspection System That Integrates Manifest Data With Imaging/Detection Processing" and filed on Jun. 15, 2015, which is a continuation of U.S. patent application Ser. No. 13/606,442, of the same title, filed on Sep. 7, 2012, and issued as U.S. Pat. No. 9,111,331 on Aug. 18, 2015, which, in turn, relies on U.S. Patent Provisional Application No. 61/532,093, filed on Sep. 7, 2011, and entitled "X-Ray Inspection System with Integration of Manifest Data with Imaging/Detection Algorithms". The above-referenced applications are incorporated herein by reference in their entirety.

FIELD

The present specification discloses systems for scanning objects and, more specifically, systems for inspection of contents of tankers, containers and vehicles for identifying threat objects and contraband.

BACKGROUND

Cargo containers need to be inspected at ports and other points of entry or transportation to assess the quantity of contents, quality of contents, and any possible anomalies that may be associated with the contents of these containers, including contraband such as explosives, narcotics, currency, chemical and nuclear weapons. In addition, cargo container inspection is useful for cargo manifest verification. A cargo manifest is a physical or electronic shipping document that accompanies the cargo and provides important descriptive information about the cargo, including bills of lading issued by the carrier or its representative(s), the shipment's cosigner and/or consignee, cargo description, amount, value, origin, and/or destination.

Current security systems are limited in their ability to detect contraband concealed in cargo. Standard and advanced X-ray systems also have difficulty detecting anomalies in break-bulk cargo. Computed Tomography (CT) based systems have been shown to be more suitable for the difficult task of detecting aviation-threat explosives in luggage and, more recently, in larger objects. However, the configuration of commonly employed CT systems prevents scaling the system up to long objects such as large cargo containers, large skids and tankers.

The problem is further compounded by the fact that as a result of the image modulation according to atomic numbers of various materials, it is common for X-ray imaging systems to produce images with dark areas. Although these dark areas might indicate anomalies or presence of threat materials, they yield little information about the exact nature of the anomaly or threat. Also, radiographs produced by conventional X-ray systems are often difficult to interpret because objects are superimposed. Therefore, a trained operator must study and interpret each image to render an opinion on whether or not a target of interest, a threat, is present. Operator fatigue and distraction can compromise detection performance, especially when a large number of such radiographs is to be interpreted, such as at high traffic transit points and ports. Even with automated systems, it becomes difficult to comply with the implied requirement to keep the number of false alarms low, when the system is operated at high throughputs.

This difficulty of inspection is magnified when inspecting larger and oftentimes, cluttered pallets, cargo containers, and cargo-carrying vehicles, such as tanker trucks, which are uniquely designed to carry fluid/liquids or dry bulk loads. Current X-ray inspection systems may not provide an accurate indication of the nature of anomalies present in tankers, which can, among other indications be evidence of theft and/or dilution of tanker contents. An X-ray image itself is insufficient to discern an amount, type, and quality of a commodity within a tanker. These parameters are typically needed to verify a manifest corresponding to the truck, or to ensure that there is no theft underway. There is thus added difficulty in inspection of tanker contents and verification of the manifest.

In addition to reporting the quantity and quality of tanker contents, there is a need to identify and report anomalies associated with the tanker contents. It should be noted that an identified anomaly may end up being contraband as well.

Therefore, there is a need to provide an automated detection system that further includes assistance tools to help operators improve their throughput by scrutinizing cargo images more efficiently, thereby increasing detection and analysis speed. Additionally, an accurate automated content detection and assessment system, such as those for tankers, is needed as a means of preventing theft of tanker contents and as a tool for quality control. Such a tanker content assessment can be a manifest verification tool, and may also have applications in cases when the manifest is not useful. Such applications may include: use at a checkpoint where all passing tankers are expected to be full or empty; to confirm that the tanker content is consistent with expected contents (for example, contents are gasoline and not water); and to check for inner-container alterations including possible alterations made to compartments, walls, and other inner portions of a container/tanker that may be an indication of nefarious intents.

There is also a need for automated detection systems that include assistance tools for detecting the presence specific contraband or threat items, such as currency, drugs, cigarettes and firearms during non-intrusive X-ray imaging of vehicles and cargo. There is also a need for algorithms for processing radiographic images that can be employed to characterize cargo and provide estimates of cargo configuration, such as cargo weight and cargo dimensions, for assisting the operators in detecting illegal items. There is further a need for detection algorithms that enable detection of differences between sequential X-ray inspection images of the same object or vehicle, so that changes in an object or vehicle may be tracked over time or distance traveled.

SUMMARY

The present specification discloses a method for verifying a type of a container, the method comprising: obtaining a scanned image of the container; and, applying at least one pixel-value line integral to the scanned image for verifying the type of container.

Optionally, obtaining the scanned image comprises obtaining an X-ray scanned image.

Optionally, applying the pixel-value line integral comprises obtaining pixel attenuation values in a vertical direction at a fixed position within the scanned image. Obtaining pixel attenuation values may further comprise indicating a shape of at least one edge of the container. Optionally, the method comprises indicating the shape of the at least one edge to be at least one of a rounded shape and a straight shape, wherein the indicating the rounded shape verifies the type of container to be a tanker and the straight shape verifies the type of container to be a cargo container.

The present specification also discloses a method for verifying contents of a tanker, the method comprising: generating an X-ray image using an X-ray scanner; using said X-ray image, detecting presence of contents within the tanker; using said X-ray image, determining a capacity of the tanker; calculating a degree of fullness of the tanker based on said contents; and analyzing the contents.

Optionally, detecting presence of contents comprises using a pixel attenuation value threshold to determine a presence of contents within the tanker. Optionally, the pixel attenuation value threshold is 2,500 for a low-energy channel of a 16-bit normalized dual-energy scanned image.

Optionally, determining the capacity of the tanker comprises determining a bottom edge and a top edge of the tanker. Optionally, the method comprises determining whether a lower edge of the contents of the tanker coincides with the bottom edge of the tanker. Optionally, the method further comprises using a pixel attenuation value threshold for determining the top edge of the tanker. Optionally, the pixel attenuation value threshold is 10,000 for a low-energy channel of a 16-bit normalized dual-energy scanned image.

Optionally, calculating a degree of fullness comprises calculating a quantity of the contents relative to the capacity of the tanker.

The method may comprises using X-ray attenuation characteristics for analyzing the contents.

The present specification also discloses a method for identifying contraband in cargo, the method comprising: generating a scanned image using a radiographic source; analyzing the scanned image to compute features of said cargo; comparing the computed features of said cargo using the features of known contraband stored in a database; calculating a probability of the cargo features matching contraband features; and determining that the cargo matches contraband when a value of said probability is more than a threshold value.

The contraband may comprise at least one of currency, drugs, cigarettes, and firearms.

The present specification also discloses a method of identifying firearms within radiographic images of a conveyance carrying the firearms, the method comprising: obtaining from a database a template image of a firearm; generating a radiographic image of the conveyance using a radiographic source; comparing a set of predefined features of the template image with the radiographic image to obtain image regions on the radiographic image comprising features matching with the predefined features; filtering the obtained image regions of the radiographic image to obtain a final set of image regions; classifying the final set of image regions for extracting image properties to determine one or more regions indicating presence of a firearm; and marking the one or more regions on the radiographic image to communicate an alarm.

Optionally, a template image of a firearm is a radiographic image of a firearm with minimal background and no clutter or is based on the type of conveyance in which such a firearm is transported.

The conveyance may be one of a cargo container, a vehicle, a trailer, a boat, a truck, a bus, and a truck driver cab.

The present specification also discloses a method for estimating the weight of a cargo, the method comprising: generating a scanned image of said cargo using a radiographic source; analyzing the scanned image to convert image attenuations to effective organic and steel thickness; determining an atomic density of said cargo; using said scanned image to generate material thickness values and atomic density values for various positions in the cargo; using the material thickness values and atomic density values to compute a weight at a given position in said cargo; and adding the computed weight of all positions to obtain total weight of said cargo.

The present specification also discloses a method for estimating the average pallet size and density in a cargo, the method comprising: generating a scanned image of said cargo using a radiographic source; analyzing the scanned image to generate organic and steel thickness profiles from image attenuation values; correcting the steel thickness profiles for background signal from the cargo; fitting the organic and steel thickness profiles using optimized pallets of cargo; and comparing the fitted profiles with known pallet data.

The present specification also discloses a method for automatically detecting anomalies in a vehicle, using the sequential images of the same vehicle, the method comprising: scanning the vehicle under inspection to generate a current scan image; identifying a most recent image of said vehicle from a database, said image being a historical scan image; determining a transformation that optimally maps the current scan image to the historical scan image; applying a normalization function to intensity profiles of the current scan image and the historical scan image; comparing intensity levels of said current scan image with intensity levels of said historical scan image on a pixel-by-pixel basis; and identifying pixels representative of anomalies in the current scan image.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein:

FIG. 6 illustrates an exemplary dashboard for a service post, as employed in one embodiment of the system described in the present specification;

FIG. 7 depicts an exemplary interface for presenting manifest information, as employed in one embodiment of the system described in the present specification;

FIG. 8 shows an exemplary user interface screen for a data center, as employed in one embodiment of the system described in the present specification;

FIG. 9 shows another exemplary user interface screen for a data center, as employed in one embodiment of the system described in the present specification;

FIG. 43 is a table illustrating a summary of fits to attenuation profile of contents of an exemplary cargo;

FIG. 48 is a table illustrating the elemental composition of selected materials, in accordance with one embodiment of the present specification.

DETAILED DESCRIPTION

Figure 1:
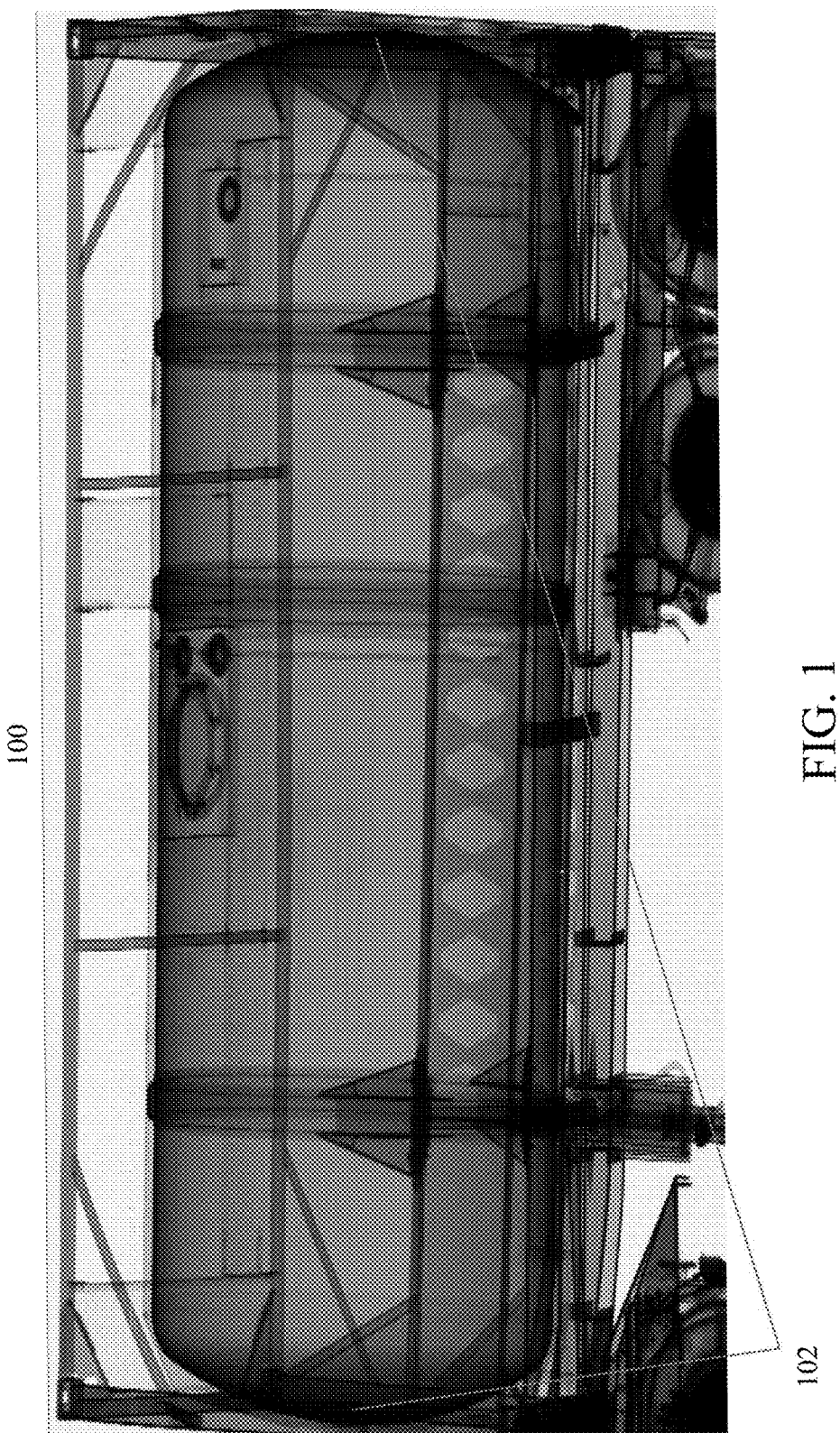
FIG. 1 is an illustration of a scanned image of a tanker, in accordance with an embodiment.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

It should be noted herein that any feature or component described in association with a specific embodiment may be used and implemented with any other embodiment unless clearly indicated otherwise.

It should be noted that all of the processes and methods described herein are implemented by a computing architecture comprising at least one server executing a plurality of programmatic instructions which may be remotely or locally stored in non-transient memory. The programmatic instructions may be executed or controlled using graphical user interfaces that are displayed on client devices which are in wired or wireless data communication with the computing architecture.

In one embodiment, the present specification discloses a method for reporting the quantity and quality of tanker contents, and for identifying and reporting anomalies associated with the tanker contents. Anomalies could be an indication of nefarious intents bringing a need to check a cargo container that is expected to be empty or full, to confirm that the cargo content is consistent with its expected contents; and to check for inner-container alterations including possible alterations made to compartments, walls, and other inner portions of a container/tanker. An identified anomaly could end up being contraband. Anomalies can also be evidence of occurrences of theft and/or dilution of tanker contents, which are difficult to detect. In some embodiments, the method uses scanned images of tankers that are under inspection, obtained by non-intrusive X-ray imaging techniques. This allows the operator or inspector to quickly ascertain and verify the contents of the tanker that is currently being inspected.

In one embodiment, images generated during a scan by an X-ray based inspection system are analyzed for specific features and parameters characteristic of specific contraband or threat items, such as currency, firearms, cigarettes or drugs. Various operator assistance tools are employed for automatic identification of specific banned items in radiographic images. In one embodiment, the system described in the present specification automatically applies detection algorithms to the image and provides alerts to operator if it detects the presence of illegal items in the object being scanned.

In another embodiment, the present specification discloses an automated method of threat detection based on processing and comparison of the X-ray images of a vehicle over time. In one embodiment, the present system provides an automated means to detect differences between sequential X-ray inspections of the same vehicle.

In another embodiment, the present specification discloses a method for characterizing cargo by providing estimates of cargo configuration, such as cargo weight as a function of position or length, pallet size and density. The present specification discloses multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

One of ordinary skill in the art would appreciate that the features described in the present application can operate on any computing platform including, but not limited to: a laptop or tablet computer; personal computer; personal data assistant; cell phone; server; embedded processor; DSP chip or specialized imaging device capable of executing programmatic instructions or code.

It should further be appreciated that the platform provides the functions described in the present application by executing a plurality of programmatic instructions, which are stored in one or more non-volatile memories, using one or more processors and presents and/or receives data through transceivers in data communication with one or more wired or wireless networks.

It should further be appreciated that each computing platform has wireless and wired receivers and transmitters capable of sending and transmitting data, at least one processor capable of processing programmatic instructions, memory capable of storing programmatic instructions, and software comprised of a plurality of programmatic instructions for performing the processes described herein. Additionally, the programmatic code can be compiled (either pre-compiled or compiled "just-in-time") into a single application executing on a single computer, or distributed among several different computers operating locally or remotely to each other.

In embodiments, an application implements the method disclosed in the present specification. In embodiments, the application is integrated with an X-ray inspection/detection system deployed at checkpoints or service posts. In one embodiment, manifest data is imported via the application. In other embodiments, the application processes detected data independent of manifest data. In one embodiment, the application works within the framework of a distributed network, wherein a point of image detection is connected to one or more points of image analysis, whereby an operator can analyze the X-ray image of the cargo. When the X-ray image has been analyzed, a service post which performed the non-intrusive X-ray scan will be notified automatically by the application integrated with the X-ray system. This allows the service post operator to make a decision to either release the cargo or to hold the cargo for further inspection.

It should be noted herein that any feature or component described in association with a specific embodiment may be used and implemented with any other embodiment unless clearly indicated otherwise.

In embodiments, the system of present specification provides several automated tools to make the image-inspection process more efficient and effective. These tools provide assistance to image operators in analyzing the images to identify a tanker and to determine its quantity and type. A tanker is different from any other cargo container due to its shape and because it is designed to carry liquefied loads, dry bulk cargo, or gases. A tanker is typically, but not always, cylindrical in shape and lies horizontally. It can be transported by truck, together referred to as a tanker truck, or by rail. FIG. 1 illustrates an exemplary scanned image 100 of a tanker that is part of a tanker truck. The scanned images, like image 100, may be obtained by dual-energy transmission systems that may range from 1MV to 9MV. In some embodiments, transmission systems with multiple views may be used to obtain the scanned images. When compared with other scanned images (such as those subsequently illustrated in FIGS. 13 and 14) rounded edges 102 of the tanker are seen in contrast from straight edges of other containers. Many variants of tankers exist due to wide variety of commodities that can be transported. Tanker trucks tend to be large; they may be insulated or non-insulated; pressurized or non-pressurized; and designed for single or multiple loads (often by means of internal divisions in their tank).

Embodiments of the specification describe exemplary methods and systems for assessing the contents of a tanker or a tanker truck (hereinafter also referred to as 'tanker').

Figure 2:
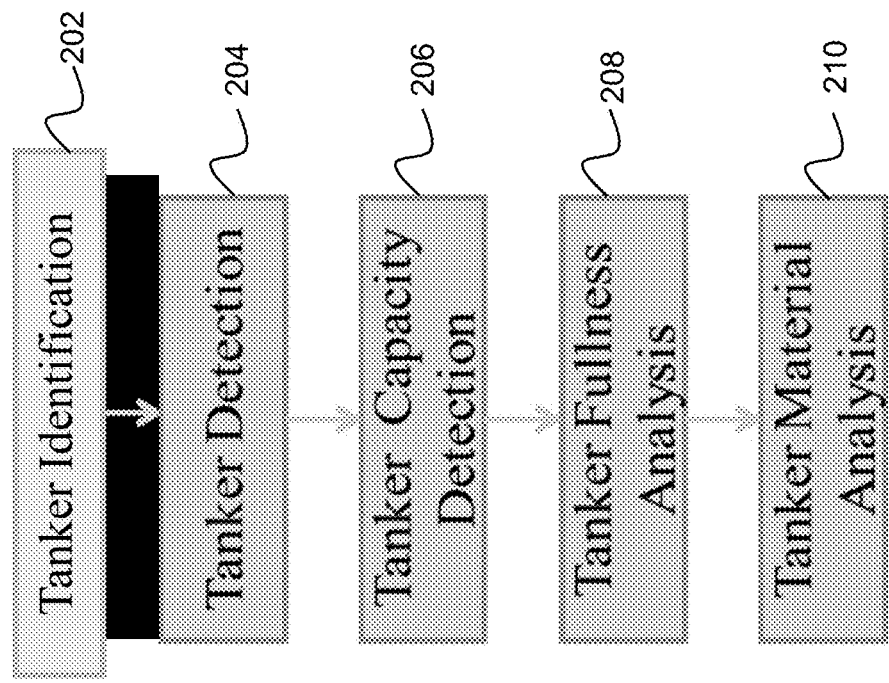
FIG. 2 is an exemplary flow chart illustrating a process of assessing contents of a tanker, in accordance an embodiment.

FIG. 2 is an exemplary flow chart illustrating a process of assessing contents of a tanker, in accordance with an embodiment. In embodiments, the described process is used by an algorithm, such as a software algorithm to assess a tanker's contents. The algorithm may be implemented at one or both of a point where a non-intrusive X-ray scan is performed and a point where image analysis is performed (refer FIG. 4). At 202, a scanned image is presented to the algorithm. The scanned image may be an X-ray scanned image. Tanker identification may be performed in a first sub-step by using object shape, size, aspect ratio, and patterns to eliminate cars, pickup trucks, vans, or any other type of vehicle (except cargo containers and tankers) from the process. The remaining image may be of a container or tanker. In a second sub-step, for a scanned image that survives the first sub-step, line integrals may be applied to identify the presence of a tanker by distinguishing it from cargo containers.

Figure 3:
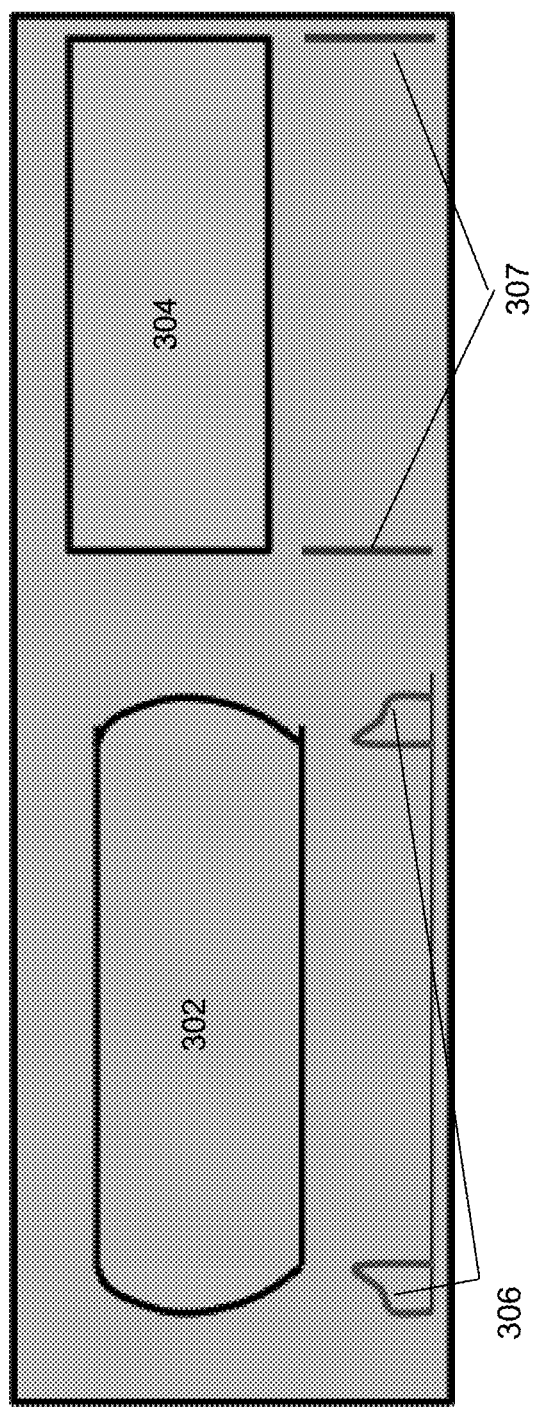
FIG. 3 illustrates an exemplary output for a scanned image of a tanker.

As discussed, a distinguishing feature of a tanker vs. a container is the rounded edge of a tanker in contrast to the straight edge of a container. Applying a pixel-value integration technique distinguishes tankers from containers. In an example, for an image, if f(x,y) represents the attenuation value of a pixel at location (x,y), then ∫f(x,y)dy provides the sum of attenuation values observed along the y-direction at position x. By generating these vertical line integrals across the entire image, rounded and straight edges can be identified to establish the presence of a tanker or cargo container, respectively. FIG. 3 illustrates an exemplary simplified algorithm input for a scanned image of a tanker 302 with rounded edges and of a container 304 with straight edges. Integrating the scanned image of the container 304 along its vertical edges results in sharp peaks 307 corresponding to the straight edges of the container. The shape is different from 306 obtained from integrating the ends of a scanned image of a tanker, resulting from the rounded-edges of tanker 302 For the decision-making process, if the maximum line-integral result, i.e., the maximum of the sums of attenuation values, exceeds 230,000, then it may be determined that the object is not a tanker. If the maximum integral result falls between 100,000 and 230,000, then the conveyance may be determined to be a tanker if other factors, such as and not limited to object height, vertical dimension, and horizontal distance between the edges, are consistent with tanker geometry. In an alternative embodiment, a binary image of the region of interest may be used in place of transmission values of the image.

Referring again to FIG. 2, at 204, the contents of the tanker identified at 202, are analyzed and detected. In embodiments, a watershed segmentation method is used to segment the input image into meaningful physical objects based on magnitude of image gradient. In embodiments, the largest object that meets pre-defined attenuation thresholds may represent the tanker content. In an embodiment, an attenuation threshold of an integral result of 2,500 for an object, measured from a 16-bit normalized dual-energy image generated from the low-energy channel, is used to determine the presence of content in the tanker. A top edge of the largest object identified (content) may represent the content level. If the largest object identified (content) does not meet or exceed the attenuation threshold, then the tanker may be considered to be empty.

Once 204 is completed and the tanker is detected with contents, at 206, capacity (or volume) of the tanker is detected. A bottom edge of the interior space within the tanker may coincide with a lower edge of content of the tanker. In embodiments, a top edge of the tanker may be determined by searching upward from a top surface of the tanker content. In embodiments, the top edge of the tanker is determined if the pixel value is within a pre-determined threshold level. In an embodiment, using the 16-bit normalized dual-energy image generated from the low-energy channel, a threshold transmission pixel value of 10,000 is used to determine the top edge of the tanker. If the pixel value is greater than the threshold, then the pixel is determined to be not part of the top edge of the tanker, and the algorithm may continue searching for the top edge.

At 208, after the top and bottom edges of the tanker are determined, a relative fullness of the tanker may be calculated by identifying location of a top surface of the tanker's content, with respect to the tanker's inner (top and bottom) edges.

Knowledge of the tanker's type, or any other information describing the tanker, may be available from its manifest. The knowledge may be used to map relative fullness of the tanker to its capacity (absolute volume). Alternatively, the tanker type may be identified by individually observing interior and exterior characteristics of the tanker, that are unique to a particular tanker type. Calibration data for various tanker types and various fullness levels may be collected to train the algorithm and validate accuracy of the calculated absolute-volume.

In some cases, surface-level turbulence may be present in the tanker's content during the tanker's scan and acquisition of the scanned image. Characterization of this turbulence may be required to estimate with acceptable precision, the relative or absolute volume of the content.

At 210, material of the tanker's content may be analyzed. In embodiments, tanker's image may be scanned by x-rays that are captured by a flat, 2D detector array after passing twice through the side walls of the tanker. As a result, measured attenuation of each radiated beam that passes through the tanker may vary with height of the tanker. The attenuation will be a function of its exit point from the tanker and the amount of content inside the tanker. The algorithm, in accordance with embodiments of the specification, will characterize the x-ray attenuation profile as a function of height, the content types of interest, the various tanker types, the amount of content present in the tanker, the percent of the tanker that is occupied, and any other information. Calibration data may be used to model the characterization process, and to validate accuracy of the characterization process. In embodiments, the calibration data is based on empirical data such as but not limited to scans of different liquid types (regular gasoline, premium gasoline, diesel fuel, water, or any other type of liquid, solid, or gas type that may be contained within a tanker) at various percentage fill levels (for example, in 5% increments). Characteristics of these images may be used to compare the scanned image and further refine the detection result.

Measured attenuation values for both high- and low-energy x-rays may be associated with different depths of content, independent from the tanker. Therefore, the measured attenuation values may be used to determine the attenuation properties of the content in isolation. Once the attenuation values of the content are determined, mu-ratio, mu-difference, and effective atomic number values can be generated. In an embodiment, Mu-ratio=Log(*HE*)/Log(*LE*); and Mu-difference=Log(*HE*)−Log(*LE*);

where, LE is the pixel value for the normalized low energy channel of the scanned image, HE is the pixel value for the normalized high energy channel of the scanned image, and Log is the natural logarithm.

This information may be used to differentiate content types, such as to differentiate water from gasoline, and one type of fuel grade from another. In embodiments, surface turbulence of tanker's content is shown to vary with content-type. In such cases, turbulence features in a scanned image may be used to identify a content-type.

Figure 4:
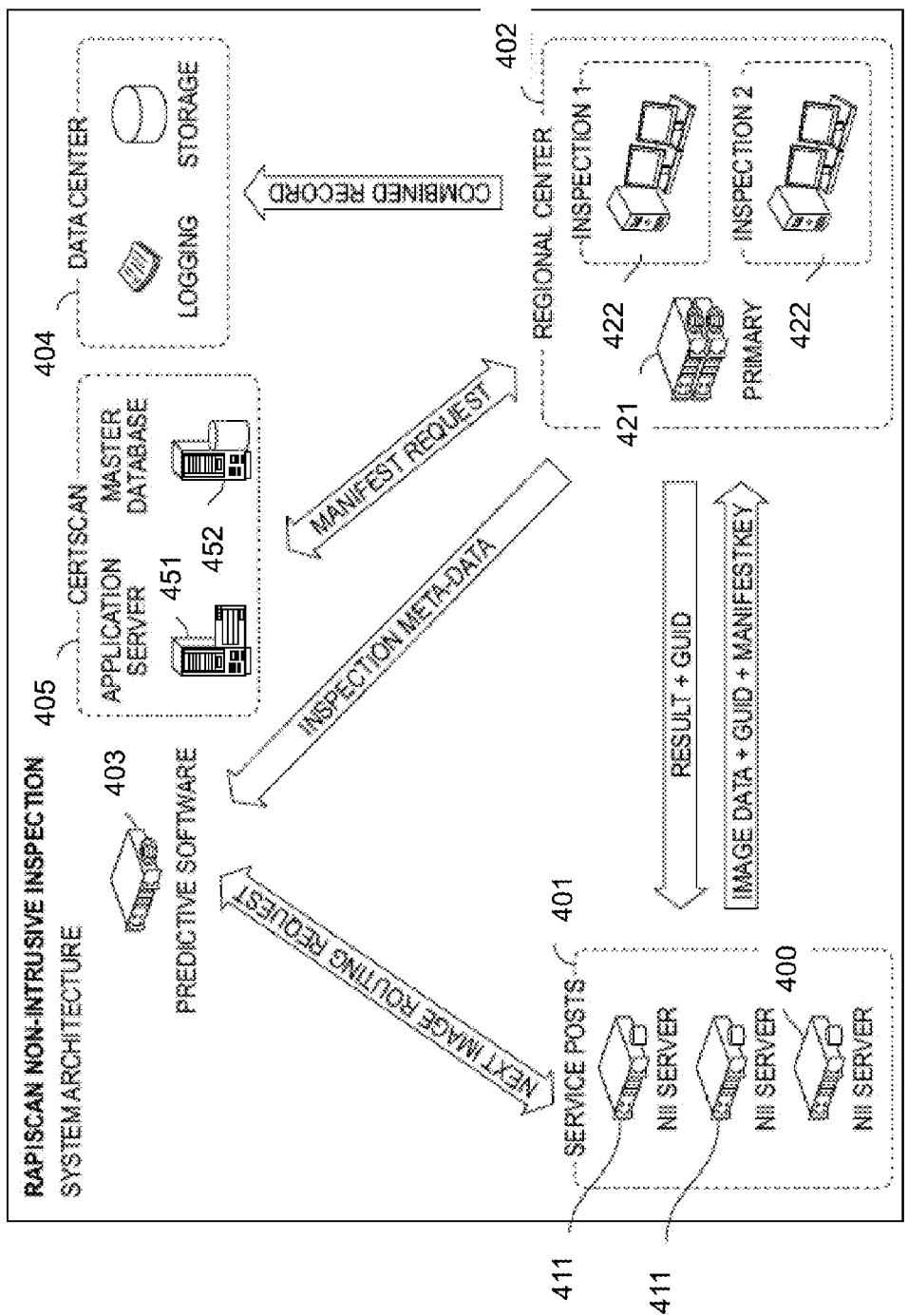
FIG. 4 illustrates an exemplary architecture of a distributed inspection network that uses non-intrusive X-ray scanning, according to one embodiment of the present specification.

In embodiments, tanker content assessment, described in context of FIGS. 1-3, is a part of a distributed inspection network, which may be deployed at ports, borders, and other types of check posts. FIG. 4 illustrates the architecture of an exemplary distributed inspection network that uses non-intrusive X-ray scanning disclosed in the various embodiments. The components of system architecture are described as follows:

Service Post and Regional Center

Referring to FIG. 4, service post 401 is the point where a non-intrusive X-ray scan is performed. It should be noted herein that one exemplary scanning and inspection system that may be employed with the systems and methods of the present invention includes, but is not limited to the Rapiscan Eagle Mobile inspection system. Any suitable system for inspecting cargo, cargo containers, and their contents may be employed. As such, U.S. patent application Ser. Nos. 12/780,910; 13/370,941; 13/548,873; 13/532,862; 13/168,440; 13/175,792; 13/433,270; 13/281,622; 13/108,039; 12/675,471; 12/993,831; 12/993,832; 12/993,834; 12/997,251; 12/919,482; 12/919,483; 12/919,484; 12/919,485; 12/919,486; 12/784,630; 12/784,465; 12/834,890; 13/009,765; 13/032,593; 13/368,178; and Ser. No. 13/368,202, all assigned to the assignee of the present invention represent various systems that may be employed with the present invention and are herein incorporated by reference in their entirety. In addition, U.S. Pat. Nos. 5,638,420; 6,542,580; 7,876,879; 7,949,101; 6,843,599; 7,483,510; 7,769,133; 7,991,113; 6,928,141; 7,517,149; 7,817,776; 7,322,745; 7,720,195; 7,995,705; 7,369,643; 7,519,148; 7,876,879; 7,876,880; 7,860,213; 7,526,064; 7,783,004; 7,963,695; 7,991,113; 8,059,781; 8,135,110, 8,170,177; 8,223,919; and 8,243,876 all assigned to the assignee of the present invention represent various screening systems that may be employed with the present invention are herein incorporated by reference in their entirety.

Service post 401 further comprises at least one, and preferably a set, of non-intrusive inspection (NII) servers 411 through which the service post interfaces with other components of the system. After scanning, the operator responsible for controlling or operating service post 401 can verify that the X-ray image produced by the non-intrusive X-ray scan is of sufficient quality to be effectively analyzed. In one embodiment, the image analysis is performed at a regional center 402. In one embodiment, if the image is incomplete, or is corrupted, black (from attenuating cargo) or is unacceptable in any manner, the service post operator may request a rescan. This can happen in cases where the time between the scan and analysis is close and the truck is still available. In embodiments, application disclosed in FIGS. 1 to 3 is implemented at either one or both of a service post 401 and a regional center 402.

Servers 411 at service post 401 comprise standard non-intrusive inspection software. When a vehicle is about to be scanned, the software at the service post queries a predictive or routing software application 403 to receive an instruction, routing information, or any other data to identify a target regional center for analysis. Regional center 402 comprises at least one server 421 and inspection monitors 422. As a new X-ray image is generated at service post 401, it is transmitted onward from service post 401 to server 421 located at regional center 402, pursuant to routing information received from software application 403, for analysis by an inspection operator located at that regional center and for subsequent storage. It should be appreciated that, in embodiments, regional center 402 and service posts 411 are geographically remote from each other.

In one embodiment, the image is allocated to a regional center and/or an operator within that regional center via predictive or routing software 403, but the work is only allocated after the image transmission is complete. In one embodiment, to streamline the data transmission activity, predictive software 403 allocates an image to regional center 402 before the image has been completely generated.

In one embodiment, in the event of the operator becoming unavailable, such as due to PC failure, log off, etc., another operator in local regional center 402 is selected automatically by predictive software 403.

Further, the system will fall back on an alternative regional center in the event of a transmission error. In one embodiment, images are buffered until a center comes back on line.

In one embodiment, each X-ray inspection image is associated with a GUID (Globally Unique Identifier), which is a unique ID across all systems. The GUID is used for associating each image with its particular manifest data. In one embodiment, identifying information, such as license plate, CCTV images etc. are also associated with the GUID at the time of scanning. In one embodiment, the GUID is a 128-bit number displayed in hexadecimal. This information may be transmitted to the inspection operators at the regional center, if required.

When the X-ray image and (optionally) manifest data have been analyzed, service post 401 which performed the non-intrusive X-ray scan is notified automatically by means of a data transmission from a software application referred to herein as CertScan 405. The CertScan application presents an interface to the operator at the service post 401, which shows the operator a rolling status of all non-intrusive X-ray scans performed at that service post, along with relevant data to allow service post 401 to either release the cargo or to hold it for further inspection. In one embodiment, the relevant data includes license plate number, work order number, and results of scan. CertScan 405 application system may also be responsible for importing the manifest data associated with the cargo or vehicle being scanned. In one embodiment, manifest data can come in one or more of several forms, such as but not limited to a) a hardcopy of the manifest; b) from a computer owned and connected to the customer database; or c) from a customer database accessed directly by CertScan 405. The format in which manifest data is supplied depends on the customer, and their local requirements and regulations.

Predictive Software 403

Predictive software 403 operates to optimally balance the load distribution of image analysis among multiple regional centers and operators. Predictive software 403 processes meta-data from multiple regional centers and service post connectors to analyze and predict the best distribution of images to operators. For example, predictive software 403 uses historical meta-data on inspection queue lengths, workload, contention time, and a randomization factor to varying degrees, to allocate work to regional centers and individual operators.

Logging and Validation

At various stages of the process, the system provides localized and centralized logging, auditing, and accounting for each action performed by an X-ray scanning operator and an X-ray image inspection analyst. Centralized logging may be provided at a data center 404. During all steps of the process, from scanning, through inspection to search, the system provides a journal of actions for each non-intrusive X-ray scan and X-ray image inspection analysis.

Inspection Performance and Metrics

In one embodiment, the system records several X-ray image inspection metrics, such as image coverage, tools used, mean time to inspect, and time pending, among other variables. These metrics can yield information for operators/image analysts such as what tools were used (for example, zoom, contrast, brightness, and other parameters), how long it took to analyze the image, and/or what part of the image was analyzed using tools. This information can then be applied to measure attentiveness and diligence of operators. For example, this information may be reviewed for each X-ray image inspection analyst, and is useful in training, review and performance evaluation. In one embodiment, inspection metrics may be measured quantitatively and be assigned minimum and maximum values, against which the operators' performance may be evaluated.

Besides helping to assess the proficiencies of the analysts, data logs also allow an assessment of inspection volumes at regional centers and the speed at which analyses are performed.

In one embodiment, the system provides for secondary X-ray image inspection, for a percentage of images, or if required, on targeted users. If required in certain cases, the X-ray image inspection process is repeated twice to cross-check results. The second X-ray image inspection can be assigned to either a purely random X-ray image scanning operator, or to nominated workstations for quality and training purposes, in various embodiments. The final X-ray image inspection result would not be sent to the service post until both inspections are complete. If either result is "suspicious", the suspicious result would be recorded, and any disagreement would be flagged.

In one embodiment, training images may be inserted into the workflow to pass on suspicious images to operators as part of their standard workload. The system then carefully segregates the results from these images, without the X-ray scanning operator knowing the difference. This allows for discrete and impromptu training of operators.

If a suspicious finding is communicated back to the service post, the operators can choose to manually open and search the suspicious cargo. In one embodiment, the system allows the operators to record detailed comments about the manual search process, which can provide both useful information about the suspicious cargo and useful feedback to trainers.

CertScan Software Application 405

Still referring to FIG. 4, the primary goal of CertScan application 405 is to present manifest information clearly for the non-intrusive X-ray image analysis inspector to quickly ascertain the contents of the cargo container or light vehicle that is currently being inspected. Application 405 may be executed on an application server 451 and may interface with a master database 452. In one embodiment, the manifest information and related data that CertScan application 405 provides may be imported into master database 452 through any suitable means, such as EDI (Electronic Data Interchange), web services, or OCR scanning of manifest documentation. The manifest information that is provided by these sources may include, but is not limited to, the following data elements:

Container Number
Arrival Date
Shipping Line
Bill of Lading Number
Port of Origin
Exporter
Consignee
Container Manifest Besides use in security inspections, additional related data captured in CertScan application database 452 may be used for internal statistical analysis, financial forecasting, and operational reporting. In one embodiment, application 405 generates various reports, including daily, weekly, and monthly data related to the expected arrival dates of cargo containers and light vehicles, as well as data regarding actual cargo containers and light vehicles scanned. In one embodiment, captured data further includes information such as the number of containers scanned at each site, average time taken to analyze a scan, scans without supporting data, number of scans with threats and without threats, etc. In one embodiment, this data is presented in real time on a user interface, referred to herein as 'Dashboard'.

In one embodiment, the use of CertScan system 405 is extended to provide reporting through online customer portals or electronic data exchange. Additionally, CertScan 405 may also be extended to provide web services for supporting "cloud" type solutions. In one embodiment, web services include obtaining manifest data and publishing or transmitting results of the scan along with any anomalies noted. These additional features are all value-added services for the security scanning system. Thus, the reports provided by CertScan application 405 may be coupled with x-ray images (JPG) which are produced by the scanning software, to create a combined reporting package. These reports may be provided to customers for their own analysis and audit purposes.

Figure 5:
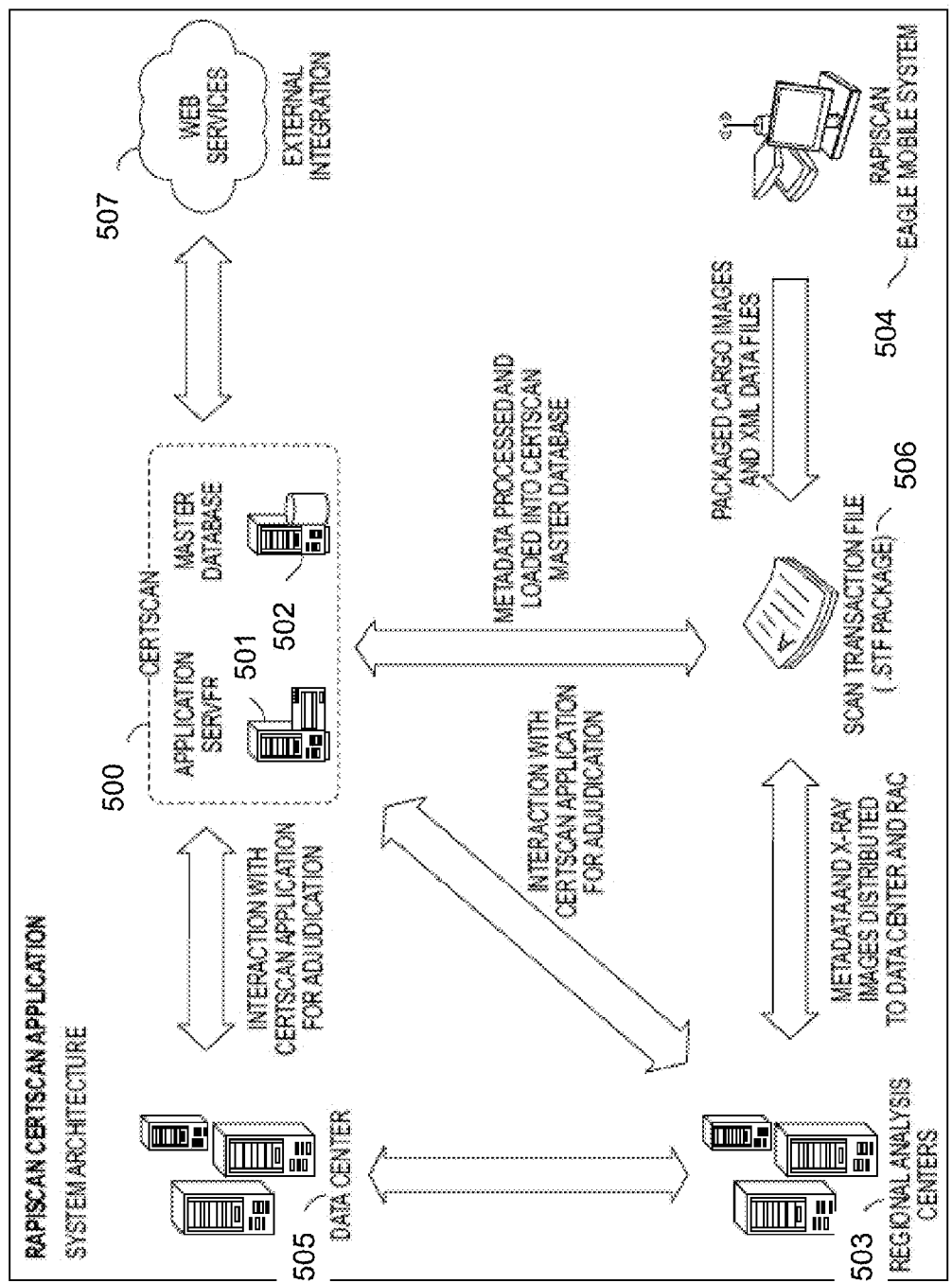
FIG. 5 is a diagram presenting the overall system architecture of an exemplary imaging system as described in an embodiment of the present specification.

FIG. 5 is a diagram presenting an overall system architecture of a CertScan application 500 (shown as 405 in FIG. 4), according to one embodiment of the present invention. The hardware for running CertScan application 500 may include an application server 501 and a master database 502. CertScan application 500 may provide manifest data to a regional center 503, which may be used by an operator in conjunction with a scanned X-ray image to analyze and determine the disposition of the cargo or light vehicles. In one embodiment, each regional center has a graphical user interface (GUI)—the CertScan Application Dashboard or CertScan Dashboard, which shows the analyst all non-intrusive X-ray scans ready for analysis. Using the CertScan Application Dashboard, the image analyst may select an X-ray Image for analysis. At the time of selection, CertScan Dashboard may display the cargo and/or light vehicle manifest data along with its X-ray image. Once adjudication is determined, the image analyst may record the result in a database associated with CertScan Application 500. The CertScan Dashboard at a service post 504 that performed the X-ray scan, may be then updated with the result. The result may allow the service post operator to take appropriate action of releasing or holding for further inspection, the cargo and/or light vehicles.

As mentioned earlier, scan images are packaged with metadata and sent from service post 504 to a data center 505 and regional center 503. The metadata may also be processed and loaded into CertScan master database 502. In one embodiment, the scan images and metadata are packaged together as a scan transaction file 506, with a '.stf' extension, for easy communication between service post 504, regional center 503, data center 505, and CertScan application database 502. In one embodiment, metadata includes information such as time of scan, the operator ID, and whether a rescan is required. This data may help establish the time it takes to transmit images and to analyze a scan. This information may also enable work quality monitoring and statistical reporting.

In one embodiment, a CertScan primary application may be a web-based application that resides at data center 505. The CertScan Dashboard in the data center may display all non-intrusive X-ray scans being performed and information on all regional centers, as well as all status information. The data center may also serve as a storage location for all X-ray images.

In one embodiment, CertScan Application 500 is externally integrated with web services 507, which may be used to generate reports as described earlier. In one embodiment, CertScan application 500 is integrated with the inspection software to provide a comprehensive solution for efficient non-intrusive X-ray inspection.

Collection of Manifest Data

As described above, manifest data can come in one or more of several forms, such as but not limited to a) a hardcopy of the manifest; b) from a computer owned and connected to the customer database; or c) from a customer database accessed directly by CertScan Application 500. In one embodiment, CertScan Application 500 accepts cargo and light vehicle manifest data in multiple formats including, but not limited to:

Electronic Data Interchange
Formatted Data Files (Fixed Width or XML)
Transportation Management System Interfaces
2D Bar Code Reader
Manifest Documentation Some methods, such as Electronic Data Interchange (EDI) of formatted data files may be preferred to facilitate faster import of data into CertScan master database 502 before the cargo arrives. When using EDI to acquire the cargo container and/or light vehicle data provided by the customer, data integration may be accomplished by importation of a formatted flat file. In embodiments, application 500 is designed to support other data exchange formats that are widely accepted by Freight Management Systems (FMS) standards, web services, or OCR scanning of manifest documentation. One of ordinary skill in the art would appreciate that the system may be configured to accept additional or other forms of manifest input.

In one embodiment, a lack of manifest information may be used to detect hidden compartments and contraband such as weapons, nuclear materials, among other contraband. More specifically, in one embodiment, incomplete or otherwise inadequate manifest information may be indicative of cargo that requires further inspection.

Thus, in one embodiment, the present specification includes systems and methods for automatically and rapidly detecting the presence of high-atomic-number (high-Z) materials such as nuclear materials; nuclear weapons; and, shielding materials that may be used to shield radiation emitted by such materials as well as by radiological dispersal devices, which can prevent them from being detected by radiation detectors. The present specification also includes the detection of other types of high-Z materials that may be smuggled in cargo due to their value, such as gold and platinum bullion, and works of art and antiquities containing high-Z materials.

The present specification therefore advantageously employs a threat detection algorithm that uses physical properties such as material density, mass absorption coefficient, and dimension to determine whether high-Z materials are present in the cargo.

The threat detection method and algorithm requires a much shorter analysis time and, thus, allows for higher system throughput compared to a conventional system, which requires an inspector manually reviewing the image or cargo for objects that are highly attenuating. For example, if multiple objects that are highly attenuating are identified, the inspector would need to make contrast enhancements with each object using a computer and input device, such as mouse. Each object has to be then evaluated for its total attenuation (or transmission) value by using the computer to select a region of interest within the object and making an estimate of the average attenuation (or transmission) value, which reflects the total attenuation (or transmission) along the X-ray path through the cargo. Before the net attenuation (or transmission) of the object can be estimated, the attenuation (or transmission) of the surrounding background material has to be analyzed. Then, to generate an average net attenuation (or transmission) of the object, the background must be subtracted from the total attenuation (or added to the transmission). Finally, the inspector must examine the shape and size of the object, and combine these estimates with the estimated net attenuation (or transmission) to reach a conclusion of whether the object represents a threat. This procedure would have to be repeated for each object and, therefore, if performed accurately, would be a very time-intensive procedure.

The threat detection process described in the present specification, in one embodiment, operates by first receiving, on a computing platform, a radiographic image of an object from an X-ray imaging system, which typically comprises a radiation source positioned opposite to, or away from, a detector array. At least a part of the area bounded by the radiation source and detector array is an inspection region, through which the cargo being inspected passes, or within which the cargo is positioned. In one embodiment, the screening system acquires the original image, which is then processed by the methods described herein. The X-ray imaging system is in electrical communication, either wired or wirelessly, with the computing platform. The threat detection algorithm then performs a first level analysis to generate a first "suspicious object" binary map by measuring a number of physical attributes. Each area on the initial binary map is used as a mask to electronically crop out part of the X-ray radiographic image for analysis, including its surrounding background attenuation (or transmission) and physical characteristics such as attenuation, size, and shape. Then, a decision is made of whether that area or portion could represent a high-Z object. This decision process results in a second binary map, which highlights those regions that represent potential high-Z threats.

In using the threat detection method and algorithm with the methods of the present specification the threat or no-threat decision time ranges from typically less than one second for cargo determined not to have any suspicious objects, to less than approximately 5 seconds for cargo having a plurality of objects or areas of interest. U.S. patent application Ser. No. 12/780,910, entitled "Systems and Methods for Automated, Rapid Detection of High Atomic Number Materials" is herein incorporated by reference in its entirety.

Dashboard for Real-Time Updates

As mentioned earlier, data is presented by CertScan application 500 in real time through a GUI referred to herein as a "Dashboard". In embodiments, the CertScan Dashboard is executed on all or a combination of the three components of the system—the service post, the regional centers and the data center. In one embodiment, the CertScan Dashboard displays a rolling list of non-intrusive X-ray scans, with data elements that are appropriate for each of the three locations.

In one embodiment, the CertScan application controls the flow of all X-ray image manifest data to ensure all three components have the content and data necessary to carry out their operations.

Service Post Dashboard

FIG. 6 illustrates an exemplary GUI (Dashboard) for the service post that is provided by the CertScan Application. This GUI has the goal of providing the service post operator with the optimal information to assist in deciding if the cargo being scanned is to be released or held for further inspection. Referring to FIG. 6, the data displayed on the Service Post Dashboard may include the container ID number 601, scan start time 602 and scan end time 603, time of start 604 and time of completion 605 of analysis of image and data at the regional center, the status (result) 606, as conveyed by the regional center, and comments 607, if any, from the regional center analyst. In one embodiment, the status or result 606 is indicated visually and by means of color coding. Thus, for example, green 606a may indicate 'ready to clear', red 606b may indicate the need for manual or visual inspection, blue 606c may indicated 'under analysis', and yellow 606d may represent already 'cleared'.

The CertScan Dashboard located at the service post need not display any information about which regional center performed the X-ray image analysis or the identity of the image analyst who performed the analysis.

Regional Center Dashboard

This CertScan Dashboard aims to provide the regional center image analyst with the information required to quickly and efficiently analyze the X-ray image for potential threats or contraband, and enables the analyst to record the results of the image inspections.

The image analyst uses the CertScan Dashboard to select an X-ray scan ready for analysis. The CertScan Dashboard located at the regional center may not display any information about which service post performed the non-intrusive X-ray scan or the identity of the service post operator who performed the X-ray scan.

In one embodiment, CertScan application interface for the image analyst is designed to be easy to use, and presents manifest information in a manner such that the analyst requires minimal time to evaluate the cargo container and/or light vehicle manifest data and record scan results.

Figure 7:
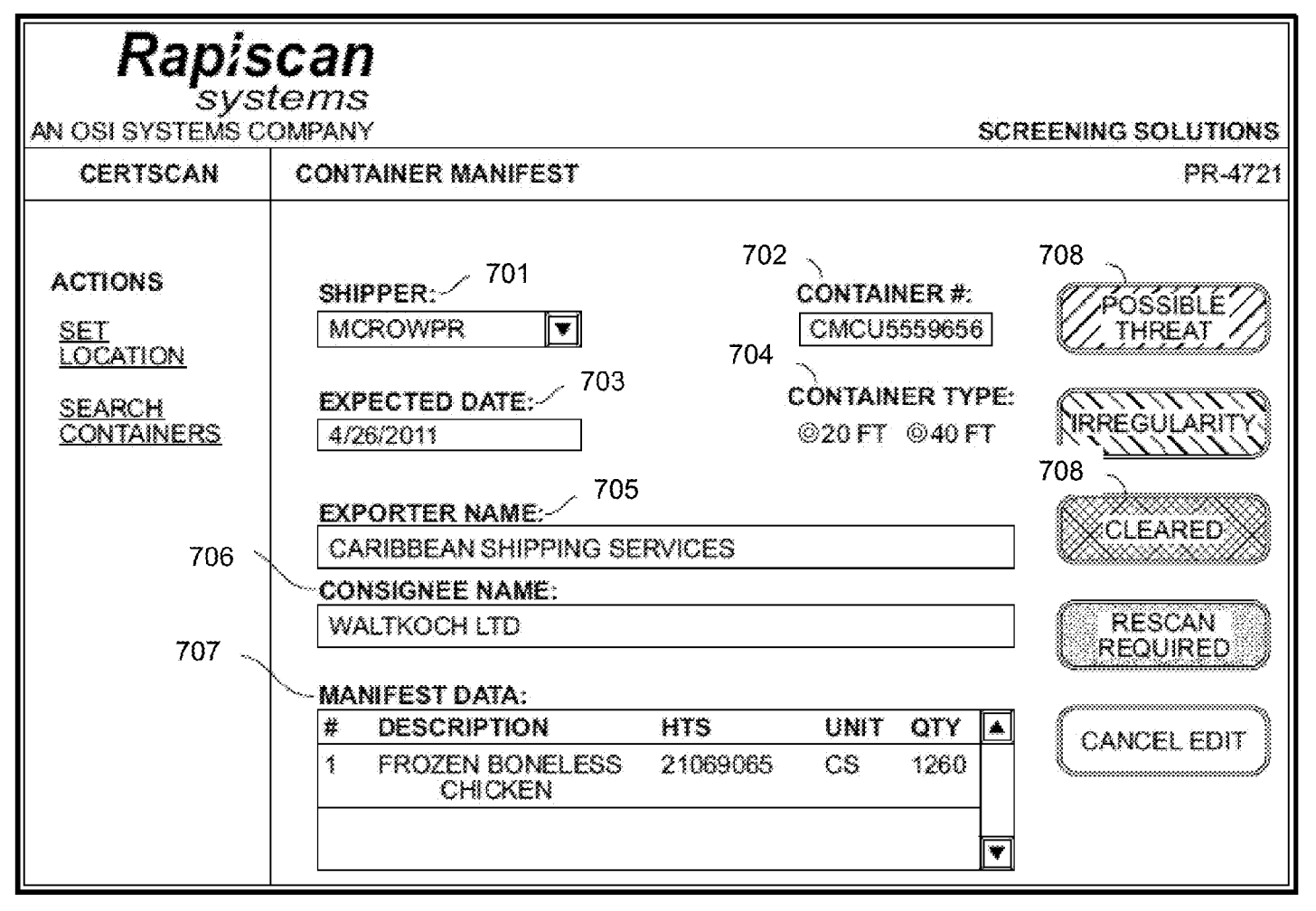

The CertScan user interface at the regional center is integrated with the inspection software to retrieve the cargo container and/or light vehicle manifest information once the X-ray scan is complete. An exemplary interface presenting the manifest information to the image analysis inspector is shown in FIG. 7. Referring to FIG. 7, the interface screen provides manifest data such as shipper ID 701, container number 702, expected date of arrival of shipment 703, type (size) of container 704, and names of the exporter 705 and the consignee 706. The screen also includes a manifest table 707 which provides data such as description of item (contents), harmonized tariff schedule (HTS), item unit, and unit quantity.

The X-ray image analysis inspector can thus verify if information about the cargo container and light vehicle matches with the scanned images. The image analysis inspector can then record the inspection result in the interface screen, using the color coded result buttons 708. In most cases the result will be 'Cleared', which is represented by a green button in one embodiment. However, there may be instances where certain areas in the X-ray Image cannot be identified clearly or it may be identified that contents are potentially harmful. In these cases, two additional results may be recorded—'Irregularity' or 'Possible Threat', represented by yellow and red respectively, in one embodiment. In one embodiment, blue color is used to indicate 'Rescan required' in case the image is unreadable. This may happen, for example, due to an environmental condition which may affect the quality and clarity of the X-ray image. In this case the cargo and vehicle under inspection need to be scanned again.

Data Center Dashboard

The data center uses the CertScan Dashboard to select an X-ray scan at any point of its lifecycle. The CertScan Dashboard located at the data center displays comprehensive information about the service posts performing the non-intrusive X-ray scan and the regional center where analysis of the X-ray image is being performed.

Figure 8:
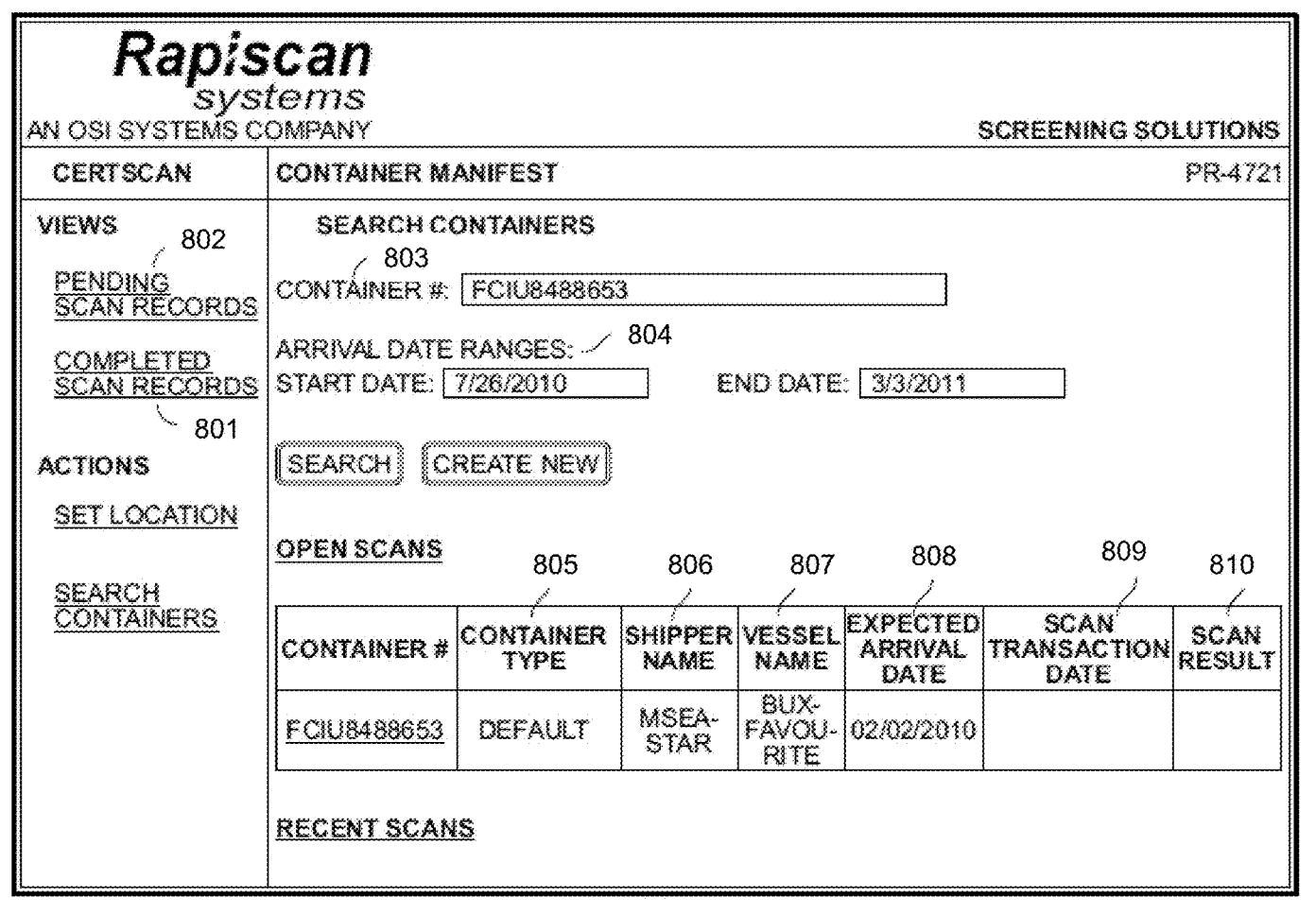

The CertScan application user interface screens for the Data Center provide all the functionality of the regional center, in addition to other functions. FIG. 8 shows an exemplary user interface screen for the data center. Referring to FIG. 8, the interface allows the dater center personnel to search for past scan records 801 as well as un-scanned cargo 802 whose manifest data is loaded in the system. The operator may also search for specific details of a cargo by container number 803 or by arrival date range 804. The search yields records for the specific container, which include data such as container type 805, shipper name 806, vessel name 807, expected arrival date 808, scan date 809 and scan results 810.

FIG. 9 illustrates another exemplary screen for the data center that shows completed scans. Referring to FIG. 9, scan records may be filtered by shipper name 901, or other attributes, such as consignee name, exporter name, date of arrival, among other parameters. In one embodiment, the completed scan records include container number 902, shipper name 903, vessel name 904, voyage number 905, and expected arrival date 906.

One of ordinary skill in the art would appreciate that all the interface screens may be customized to meet the customer's needs, and data may be selected for display accordingly.

System Logging

In one embodiment, the CertScan application performs logging of all activities throughout the full non-intrusive X-ray scanning operation. The application log provides information and reports such as:

Timings related to the non-intrusive X-ray scan process
CertScan Application performance monitoring
CertScan Application system health
CertScan Application error traps One of ordinary skill in the art would appreciate that CertScan application log data may be used for internal system monitoring as well as for reporting based on customer needs.

The applications of the present inventions may be extended to security inspection at ports, borders, aviation checkpoints as well as supply chain security. The system can import manifest data from a port, border or aviation data management system, as the case may be, and compare the obtained information with image of container. In one embodiment, the system of present invention automatically applies detection algorithms to the image and provides alerts to operator, if there are any mismatches with the manifest. This 'Operator Assist' function enables the security personnel to identify threats or other contraband more efficiently, and they can determine if de-vanning or opening the container is required. In one embodiment, multiple operators work in a matrix or networking environment and review the alarms generated automatically by the system. The operators then decide to clear or further investigate the alarms. The application of the system may be extended to supply chain security, where devices that are capable of sending messages through cell phones or satellite networks, may be attached to pallets and containers. These devices may be used to send alarms remotely to a central monitoring station, along with X-ray and video images if there is an alarm.

One of ordinary skill in the art would appreciate that although the process of an operator inspecting an image to verify that the cargo matches the manifest is much more efficient than manually opening the container, it still requires significant labor. The labor-intensive nature of the problem is even more evident in applications such as inspecting each railcar in a long train with hundreds of railcars and trying to identify thousands of cargo types. Often, it is difficult to identify the cargo from the numerous images in such cases.

To address this problem, in another embodiment, the present invention is directed towards the analysis of images generated by non-intrusive cargo inspection systems with the goal of improving the efficiency of the process to verify that cargo matches the manifest.

For the purpose of this specification, cargo manifest is defined as a manifest that lists all cargo codes carried on a specific shipment. Further, cargo codes may be standard, also known as harmonization codes, or may be provided by various local custom agencies and may be different depending on the jurisdiction.

In one embodiment, predetermined image features of inspected cargo with an associated cargo code are computed and compared with features associated with the same cargo code saved in a database. The comparison results in a probability that the inspected cargo matches the declared cargo in the manifest. If the probability is greater than a predetermined threshold, the cargo will be declared as matching the manifest. Otherwise, the cargo does not match the manifest. In another embodiment, the probability is presented to the operator and the operator makes the decision. These processes are illustrated by means of flowcharts in FIGS. 10, 11 and 12.

Figure 10:
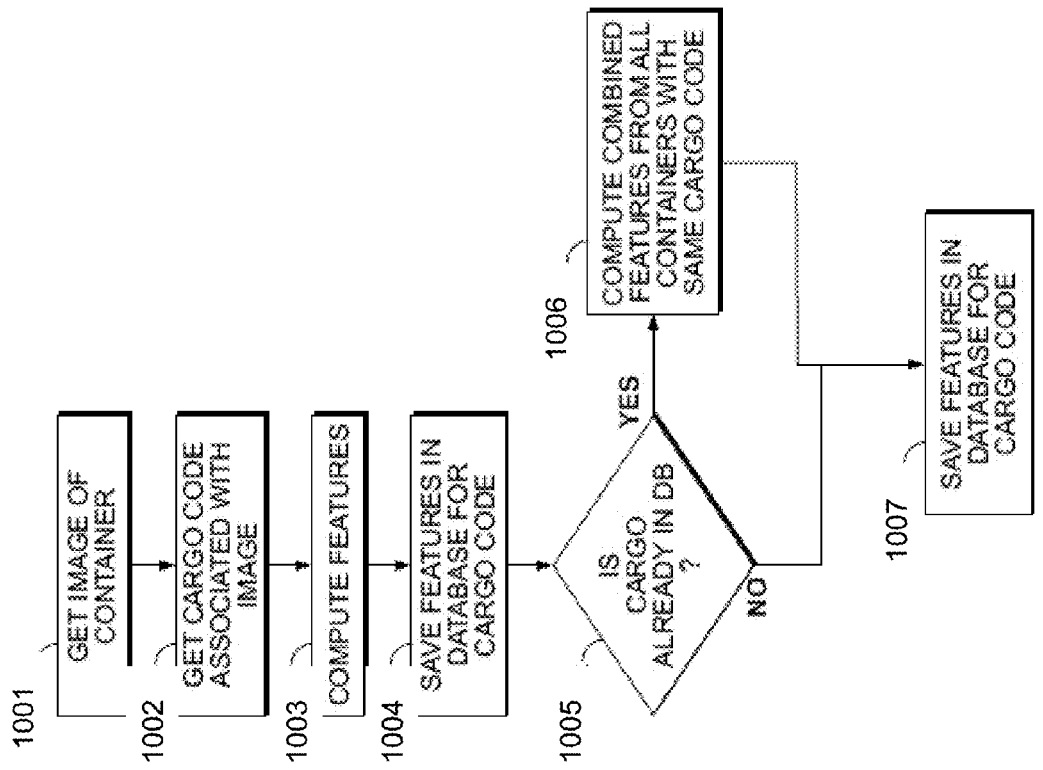
FIG. 10 is flowchart illustrating one process for preparing a features database, according to one embodiment of the system described in the present specification.

Referring to FIG. 10, the process of preparing a features database is shown. In a first step 1001, the system obtains the image of the container. The image is obtained through non-intrusive scanning at any of the service posts, as described above. It should be understood by those of ordinary skill in the art that the radiographic images could be generated by low, medium or high-energy X-rays, gamma rays, neutrons or other type of radiation. The images could also contain atomic-number information generated from any modality of dual-energy or dual-species inspection. The images could be generated by one or more views and could be reconstructed in three-dimensions, from the views.

After obtaining the image, the system obtains cargo code associated with the image, as shown in step 1002. Cargo codes are obtained from manifest data, as described above. Thereafter, features of the image are computed, in step 1003. Computed features and their standard deviation are then saved in the database along with the number of images used to compute the features, and are associated with that cargo code, as shown in step 1004.

The features include, but not limited to, attenuation, texture, atomic number, and/or cargo height. For tomographic and multi-view systems, density is also a useful feature. This also would include elemental composition or features derived from the composition for neutron-based interrogation. It should be understood by those of ordinary skill in the art that other features not listed here could be used to match the cargos.

In the next step 1005, the system checks if any entries for that cargo code are already stored in the database. If so, the system combines features from the containers with same cargo code. This is shown in step 1006. The combination of the feature values takes into account the number of images used to compute the feature value and is weighted accordingly. Also, the user is notified of outlier feature values (values that are outside the three standard deviations or other selected range) for acceptance before the combination takes place. Thereafter the combined set of features for that particular cargo code is saved in the database, as shown in step 1007. Thus, the features saved in the database per cargo code are computed from a combination of feature values from a large number of cargo images with same cargo code. The feature values are updated as additional cargo images are collected. Additional features can also be computed as their usability becomes available.

Figure 11:
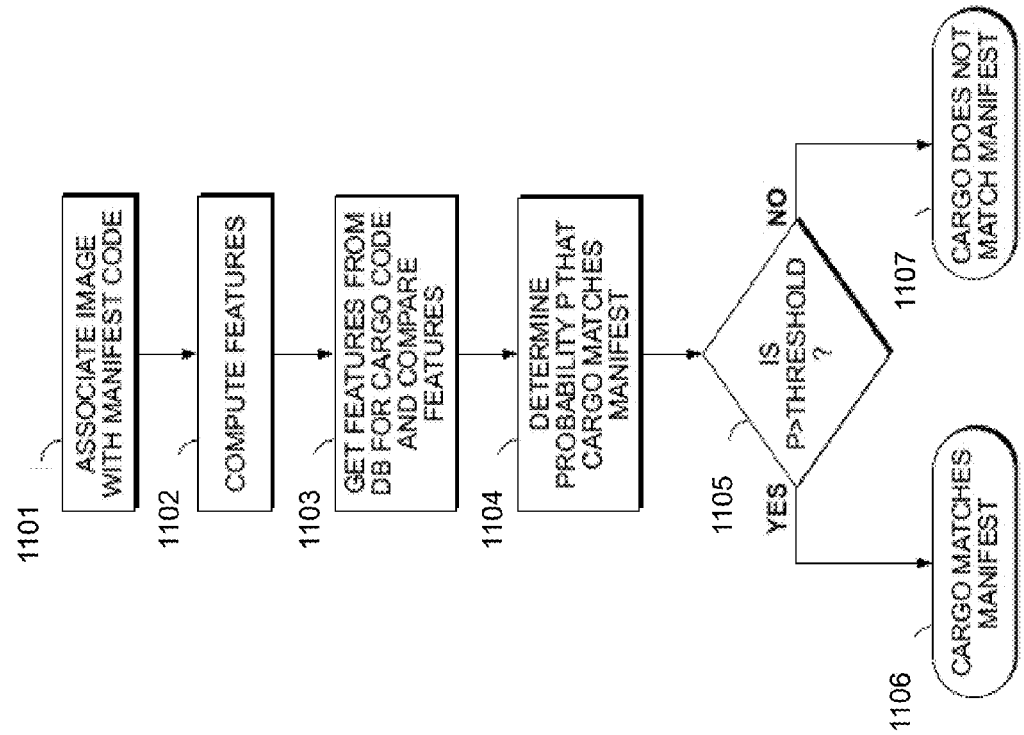
FIG. 11 illustrates the use of the features database described with respect to FIG. 10 to determine if cargo under inspection matches manifest information.

FIG. 11 illustrates a method for performing cargo-manifest verification for an individual cargo container. In the first step 1101, an image captured at a service post is associated with one or more cargo codes, depending on the contents of the shipment as defined in manifest data. Then, the features of the image are computed, in step 1102. Thereafter, the system obtains features for that cargo code stored in a database, and compares them to the computed features. This is shown in step 1103. The system then determines the probability 'P' that cargo matches manifest, in step 1104. Probability 'P' is then compared to a threshold value in step 1105. If 'P' is greater than the threshold value, it implies that cargo matches manifest information declared, as shown in step 1106. If 'P' is less than the threshold value, it indicates that the contents of the cargo are not the same as declared in the manifest, as shown in step 1107.

In one embodiment, the threshold value may be determined in accordance with the user's preferences. For example, if custom office is using the system and they want to detect most contraband even at the expense of higher false alarm rate, they may be able to set a high threshold value, such as 90%. Conversely, if the custom agency does not want to have a high false alarm rate, they can choose to set a low threshold value, such as 60%. Further, the customer may decide that some categories of goods are more important, such as those associated with higher duties, than others, and place different thresholds for different types of goods.

Further, before flagging cargo, a predetermined minimum set of images may be used to compute the features. The customer may decide that the features database is complete and more images do not need to be used. In this case, there is no need to add more images to the database. However, if the database did not use enough images, or the customer wants to improve the accuracy of detection, an authorized operator can request to add more images to the database. The operator should have a high confidence that the cargo matches the manifest, which is generally achieved with experience with the type of cargo coded in the manifest or a manual inspection and verification of the container contents.

Figure 12:
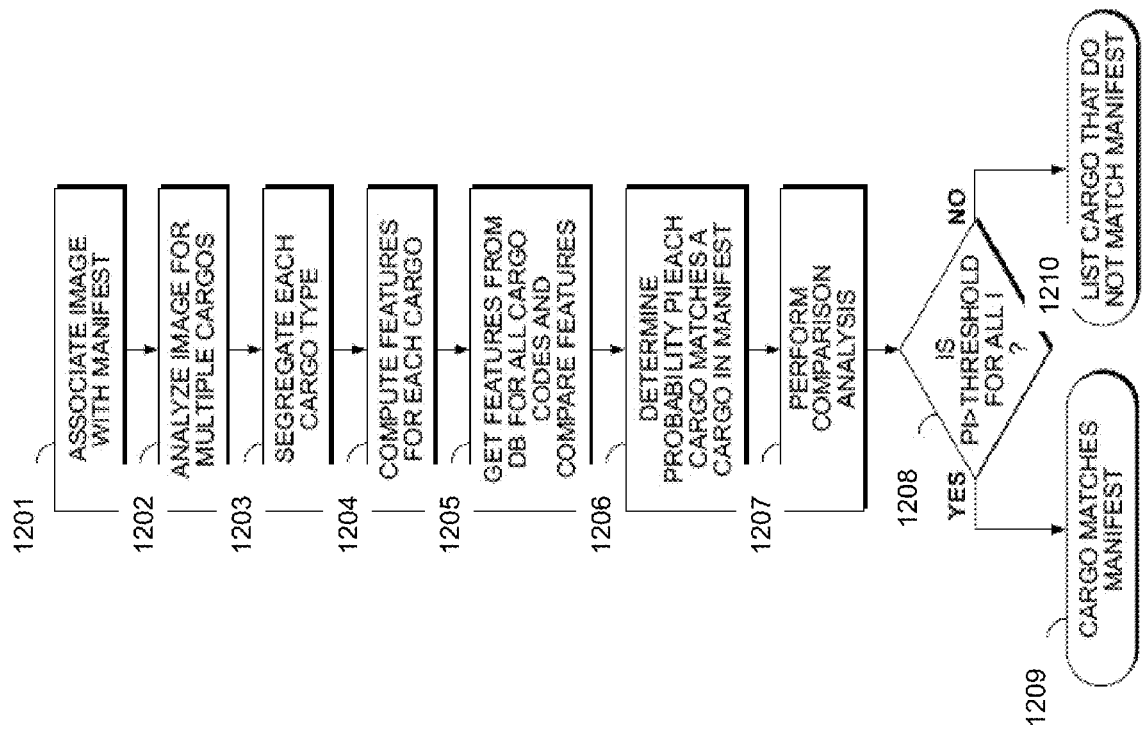
FIG. 12 illustrates the process of using the features database described with respect to FIG. 10 to determine if cargo under inspection matches the manifest, when there is more than one type of cargo present in the shipment.

When a shipment contains more than one type of cargo, the image is analyzed for different types of cargo and segregated. This process is illustrated in FIG. 12. Referring to FIG. 12, the system first associates the image of scanned cargo with manifest information in step 1201. The image is then analyzed to determine if there are multiple cargos, in step 1202. The system then segregates each cargo type, as shown in step 1203. The segregation of cargo types is discussed in greater detail with respect to FIG. 14. The features for each cargo type are then computed in step 1204 and compared in step 1205 with the feature values stored in the database for each cargo type listed in the manifest. A list of probabilities for each segregated cargo is then produced.

Thus, '$P_i$' is the probability that $i^{th}$ cargo matches with the declared manifest. This is shown in step 1206.

Each '$P_i$' is then compared to the threshold value, as shown in step 1207. One of ordinary skill in the art would appreciate that since there are more than one type of cargos, there may be more than one threshold value for comparison. The system checks if $P_i$ is more than the threshold value for all "i" in step 1208. If $P_i$ is more that the threshold value for all "i", it is determined that the cargo matches the manifest, as shown in step 1209. Otherwise, if one or more segregated cargos do not match features for one of the cargo codes in the manifest, the cargo(s) will be assigned as not matching the manifest and all cargos that do not match the manifest are listed. This is shown in step 1210. Alternatively, the probabilities for each segregated cargo may be displayed to the operator for decision.

Figure 14:
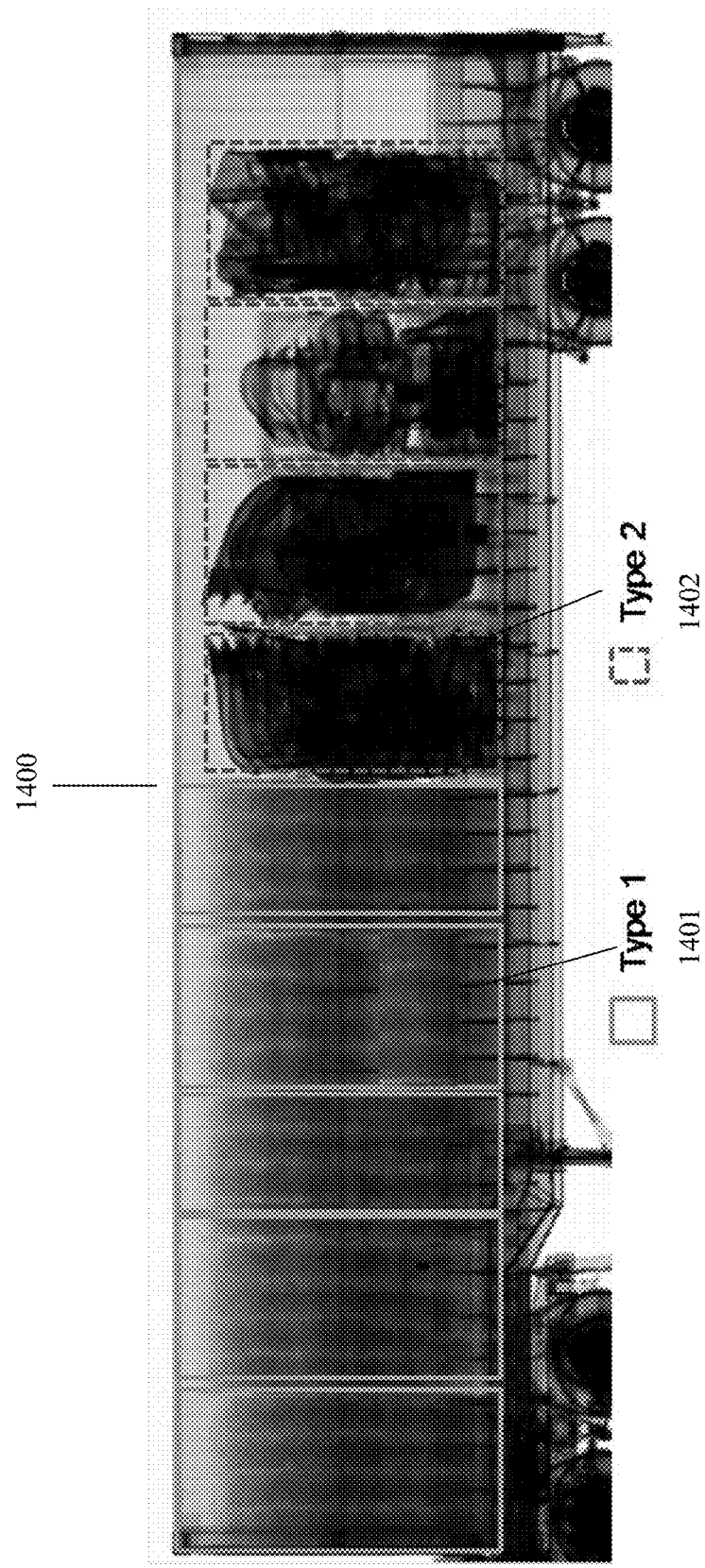
FIG. 14 illustrates the segregation of cargo into various cargo types based upon scanned images.

In one embodiment, an operator can separate the cargo visually and/or with the help of tools, such as a "rubber band" type of tool. In another embodiment, cargo may be automatically segmented and features of the different parts of the cargo may be computed, as shown in FIG. 14. Segmented regions with similar features are assumed to be same cargo. Thus, on the basis of features cargo in image 1400 of FIG. 14 may be segregated into Type 1 1401 and Type 2 1402.

In another embodiment, the operator inspects the image of a container with associated manifest. The operator then requests to retrieve from the image database a number of images of cargo with same cargo code. The operator compares the images visually and/or aided with various image manipulation tools to determine whether the cargo matches the manifest. If the manifest lists more than one cargo code, the operator would request images for each cargo code for comparison.

Figure 13:
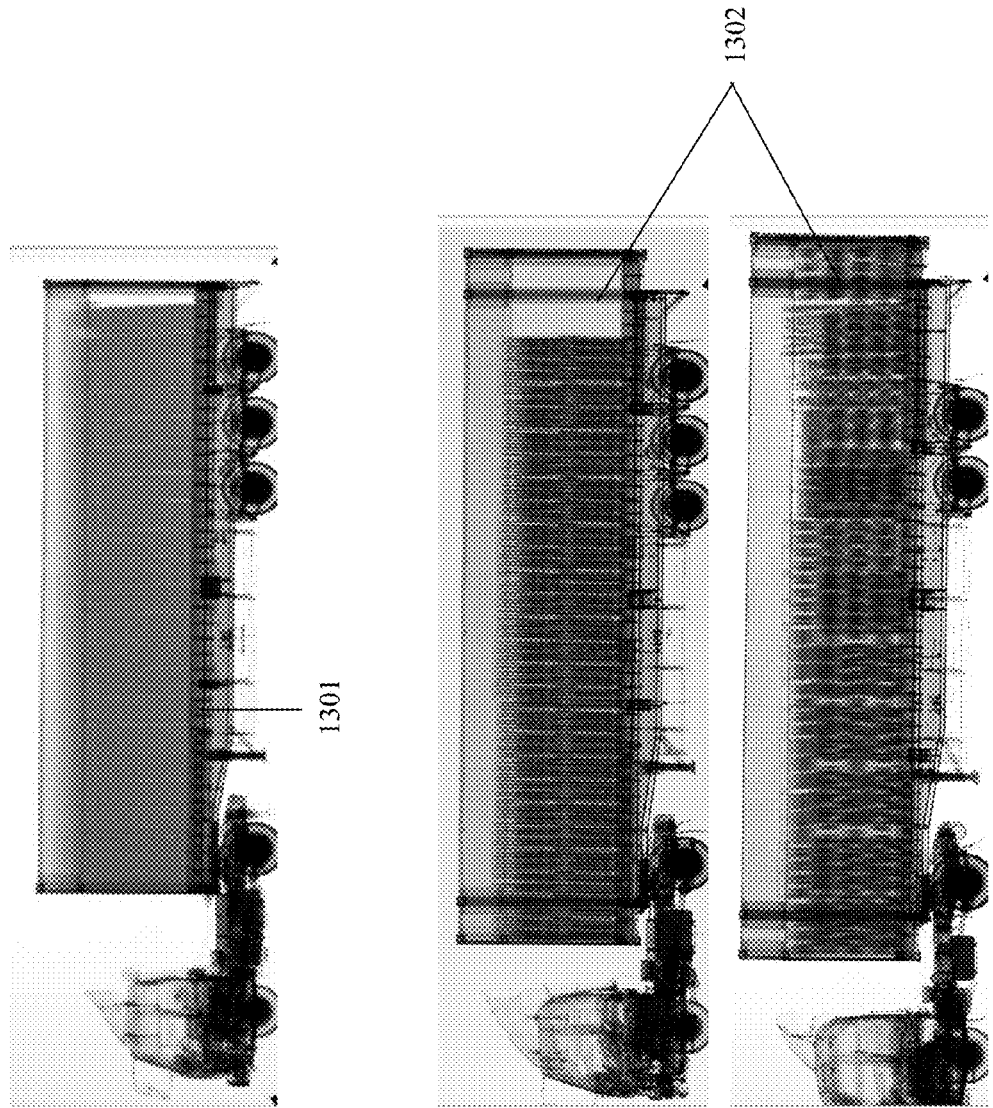
FIG. 13 illustrates how currently scanned images may be visually compared with images from the database of the present specification to determine if cargo matches the manifest.

Another method to assist the operator for determining whether a cargo image matches the manifest is to retrieve a number of images from the image database that have the same cargo type. This is shown in FIG. 13, wherein the current image 1301 of the cargo can be visually compared by the operator with images 1302 of the same cargo type from database. Additional assistance is provided by displaying values of various cargo features of the current and previously imaged cargo. In the example, shown, and by way of example only, the current image 1301 is different from the database images 1302. Thus, the operator should make a decision that the cargo does not match the manifest, because the current image is different from those in the database.

In another embodiment, the present specification discloses a system and method for automatic identification of firearms in radiographic images.

Radiographic systems such as X-ray machines are generally used to detect weapons concealed in a cargo, containers, or vehicles. However, currently available radiographic scanning systems provide two-dimensional images of the objects which by themselves are not always sufficient to accurately identify to the operator the presence or absence of a firearm. In embodiments, a firearm includes but is not limited to a weapon such as handgun, pistol, revolver, rifle, shotgun, BB/pellet gun, and assault rifle. Generally, the X-ray system operators review the real time two-dimensional images collected at X-ray checkpoints and check each image for the presence of objectionable items such as a firearm. As an object, such as a firearm, can be positioned in an infinite number of orientations in a three dimensional space, two-dimensional images of such objects often lack the clarity needed to determine the exact shape of the object just by looking at such images.

Figure 15:
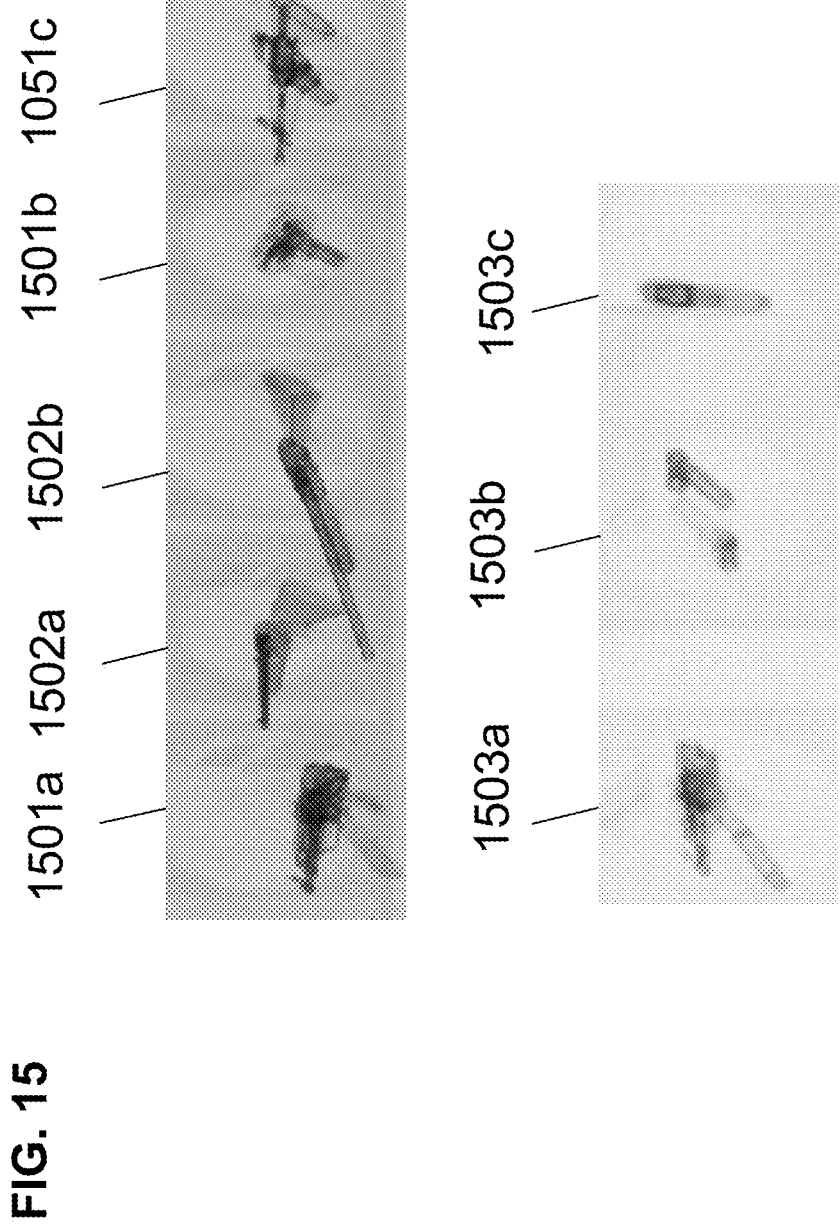
FIG. 15 illustrates three different types of radiographic firearm images with each one positioned in multiple orientations in three-dimensional space.

The above complexity involving two-dimensional images is described with reference to FIG. 15 which shows three different types of firearm images, with each one positioned in multiple orientations in three-dimensional space. As shown in FIG. 15, the images 1501a, 1501b and 1501c represent the same firearm object whereby each image captures the firearm object in a different orientation. Similarly, images 1502a and 1502b represent a single firearm object whereby each image captures the object in a different orientation. Similarly, images 1503a, 1503b and 1503c represent another single firearm object whereby each image captures the object in a different orientation. As a single three-dimensional object may be placed in any of the infinite number of possible three-dimensional orientations in a cargo or vehicle, it is not possible to simply compare a two-dimensional image of such object with a predefined reference image and predict, with high probability, the presence or absence of a firearm. One can appreciate that while it is easy to observe the shape of a firearm in some of the presented images, it may be difficult to identify a firearm from the shapes of other images as well. This task is very subjective and depends on the operator.

In an embodiment, the present specification describes a method wherein the images generated by radiographic systems are further processed through advanced image processing techniques to automatically identify objects such as firearms. While, in an embodiment, the systems and methods disclosed in the present specification are used to support the inspection of land- and sea-transported cargo, cargo-carrying truck cabs, and light vehicles, however, in other embodiments, the method disclosed in this specification may be applied to any transmission x-ray based system inspecting other conveyances and other concealment methods, and is therefore not limited to the discussion herein. In embodiments, firearms such as handguns and rifles can be detected either as single objects or as multiple objects in a commercial package. In embodiments, the systems and methods of the present specification can be used to detect firearms in cargo containers, vehicles, trailers, boats, trucks, buses, and truck driver cabs. In other embodiments, the systems and methods of the present specification can be adapted for any other type of transport and conveyance methods such as luggage and even air passenger carry-on items such as cardboard boxes, without departing from the spirit and scope of the present specification.

In an embodiment, the present specification describes an advanced image processing method for detecting the presence of firearms from two-dimensional radiographic images that involves comparing such images to reference images, which in some embodiments, represent standardized templates of firearms. In an embodiment, the present specification describes a method for detecting the presence of firearms from two-dimensional radiographic images by using a combination of image processing techniques such as Maximally Stable External Regions (MSER) and Speeded Up Robust Features (SURF), resulting in a greatly enhanced probability of detecting firearms placed in any orientation within a three-dimensional space. The method of the present specification results in a lower processing time as well as a lower false alarm rate, and a greatly improved detection rate as compared to prior art radiographic-image based firearm detection methods.

In an embodiment, the present specification describes the creation of reference images, which in some embodiments are predefined templates that are used to identify suspicious regions in an image. A template consists of a radiographic image of a firearm with minimal background and no clutter. These templates are compared with structures within the image-under-inspection to identify firearm candidates. Because of the versatility of each template, its size can be modified and it can be tailored to the type of firearm of interest. In an embodiment, such templates are generated from radiographic image data during a development phase. Template candidates are selected during algorithm development. In an embodiment, the templates comprising image features that result in successful template-matching with radiographic images of firearms are eventually used for firearm detection purposes.

Figure 16A:
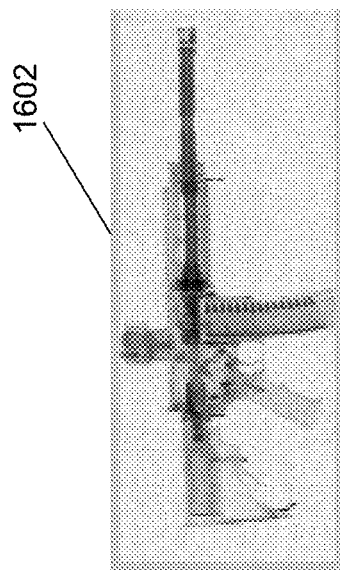
FIG. 16A illustrates an exemplary template of an assault rifle, in accordance with an embodiment of the present specification.
Figure 16B:
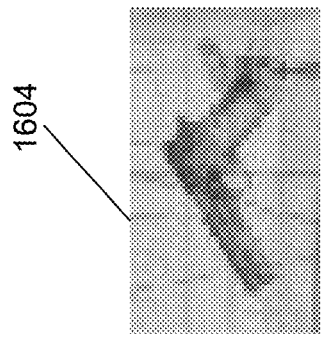
FIG. 16B illustrates an exemplary template of a hand gun, in accordance with an embodiment of the present specification.

FIG. 16A illustrates an exemplary template of an assault rifle 1602, in accordance with an embodiment of the present specification. FIG. 16B illustrates an exemplary template of a hand gun 1604, in accordance with an embodiment of the present specification. A radiographic image obtained from a container or object under inspection may be compared with at least one of templates 1602, 1604 and, if an assault rifle or handgun is present in the object under inspection, a match may result based on the comparison. In embodiments, the template of a firearm is based on the type of conveyance in which such a firearm is transported. Each type of conveyance has a characteristic image background and typical clutter objects for consideration in development of templates. For example, a template used to inspect a vehicle will account for the passenger seats and the steering wheel, and will be optimized to inspect the vehicle floor for firearms. In embodiments, the number and sizes of applicable templates varies for various modes of conveyance such as a light vehicle, container or a truck driver cab. In an embodiment, a radiographic image may be matched against any one of the pre-defined templates for a corresponding mode of transport.

In an embodiment, the features that are used for carrying out a comparison between pre-defined templates and the radiographic image being inspected are based on Maximally Stable External Regions (MSER) techniques, known in the art, which are effective for blob detection and are insensitive to affine transformation. In this context, affine transformation refers to a change in the orientation or size of an imaged firearm due to the firearm's rotation or distance from the x-ray source, respectively. MSER techniques/algorithms are commonly used to find correspondences between image elements/features from two images with different viewpoints, and to extract a comprehensive number of corresponding features between the two images. These features capture the most difficult aspects of recognizing a firearm in a free form of 2D presentation, namely, at various orientations and for various magnifications. In an embodiment, the matched results generated through template matching then undergo a filtering process utilizing the Speeded Up Robust Features (SURF) technique, known in the art. Finally, other features are extracted to support a classification process based on the image region's clutter, background, material, and statistical properties.

Figure 17:
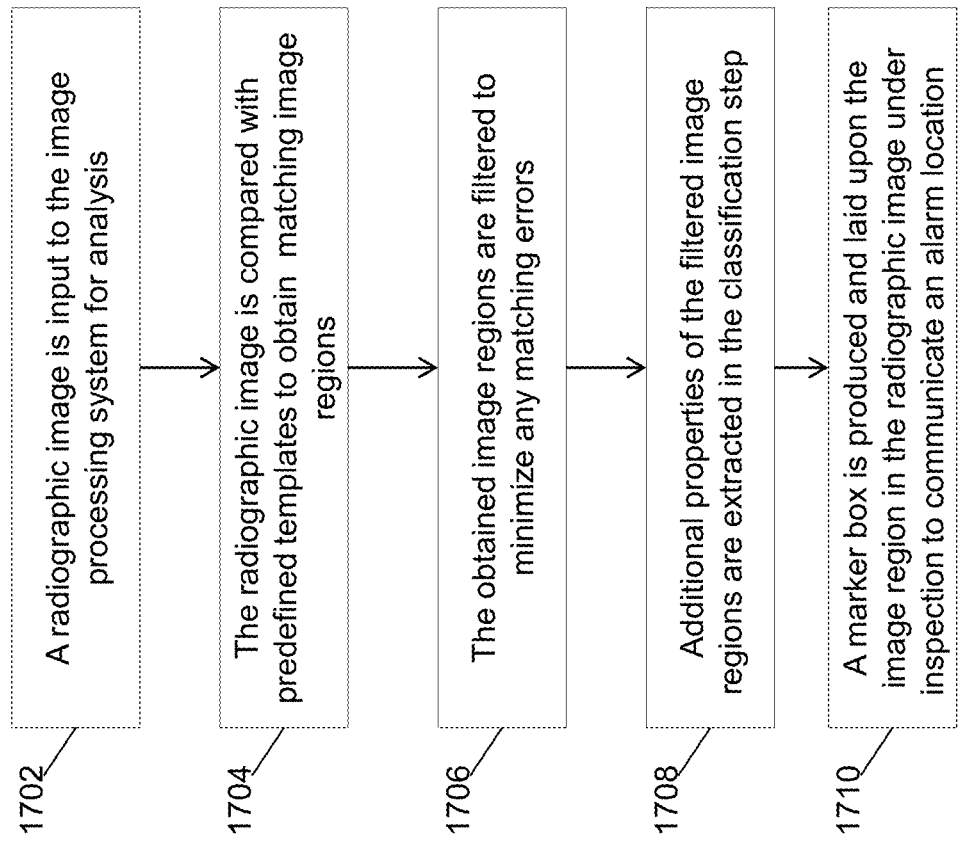
FIG. 17 is a flowchart illustrating the steps of an advanced image processing method, in accordance with an embodiment of the present specification.

FIG. 17 is a flowchart that describes the steps of the advanced image processing method, in accordance with an embodiment of the present specification. As shown in FIG. 17, at step 1702, a radiographic image is input to the image processing system for analysis. The radiographic image may be of a vehicle/cargo carrying goods in which firearms may or may not be present. In an embodiment, a radiographic system such as an X-ray inspection system is coupled to the image processing system such that the images captured by the radiographic system are automatically transmitted to the processing system for advanced image processing in accordance with the present specification. In an embodiment, the image processing system is a part of the radiographic system itself, and in another embodiment, the image processing system is located at a remote location accessible through a central server.

It should be noted herein that the systems of the present specification further comprise at least one processor to control the operation of the entire system and its components. It should further be appreciated that the at least one processor is capable of processing programmatic instructions, has a memory capable of storing programmatic instructions, and employs software comprised of a plurality of programmatic instructions for performing the processes described herein. In one embodiment, the at least one processor is a computing device capable of receiving, executing, and transmitting a plurality of programmatic instructions stored on a volatile or non-volatile computer readable medium.

The input image is analyzed in step 1702 to characterize the conveyance object in the image as either a cargo container or a vehicle, such as but not limited to, cars, trucks, buses, and vans. In embodiments, at transit points that involve the movement of a variety of transport means, the exact transport or conveyance system such as a cargo or a truck corresponding to any radiographic image is also determined through radiographic scanning. In an alternate embodiment, the transport system corresponding to the radiographic image may be manually fed into the image processing system along with the radiographic image to be inspected. In embodiments, in case a cargo unit is characterized in the image, an additional step of determining presence of a tractor unit containing a driver cab coupled with the cargo unit is also performed. Due to the distinctive features of vehicles, containers, and driver cabs, a unique image processing method may be applied for analysis of each.

At step 1704, the processing system compares the radiographic image with predefined templates to obtain possible matching region or points. In an embodiment, regions within the radiographic images are compared with the predefined templates using the MSER method, which serves as the primary feature-detector for firearms identification. The benefits of using the MSER method include its insensitivity to affine transformations, which preserves neighboring intensity topology; and multi-scale detection, which senses both small and large structures in the image. In an embodiment, a set of features are detected by applying the MSER method to both the template and the radiographic image-under-inspection, which can be a transmission image or its inverse (an attenuation image). The features may comprise a central location, orientation scale, and all pixel locations with a predefined region.

Figure 18B:
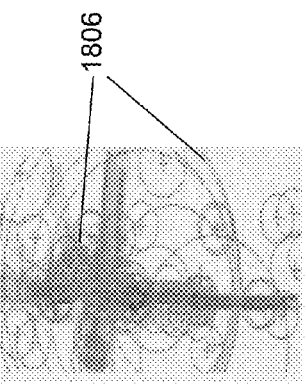
FIG. 18B illustrates an exemplary firearm template comprising a plurality of Maximally Stable External Regions (MSER) features marked thereupon, in accordance with an embodiment of the present specification.
Figure 18A:
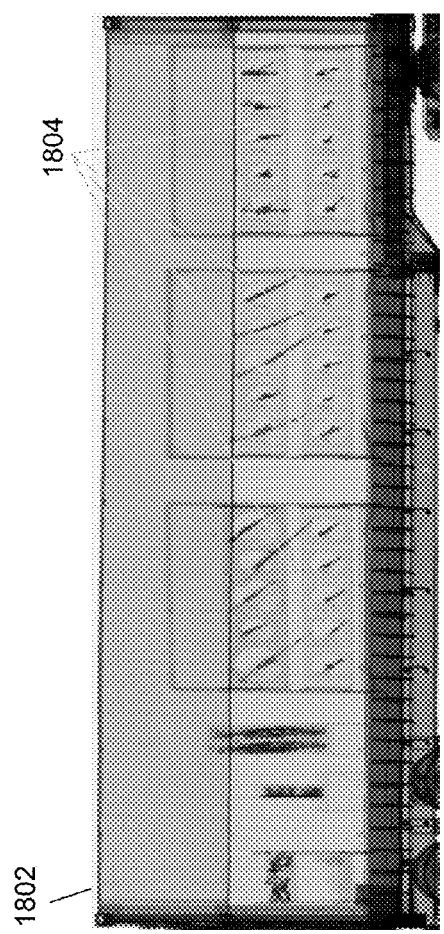
FIG. 18A is an exemplary radiographic image of a cargo container comprising firearms located throughout various orientations.
Figure 18C:
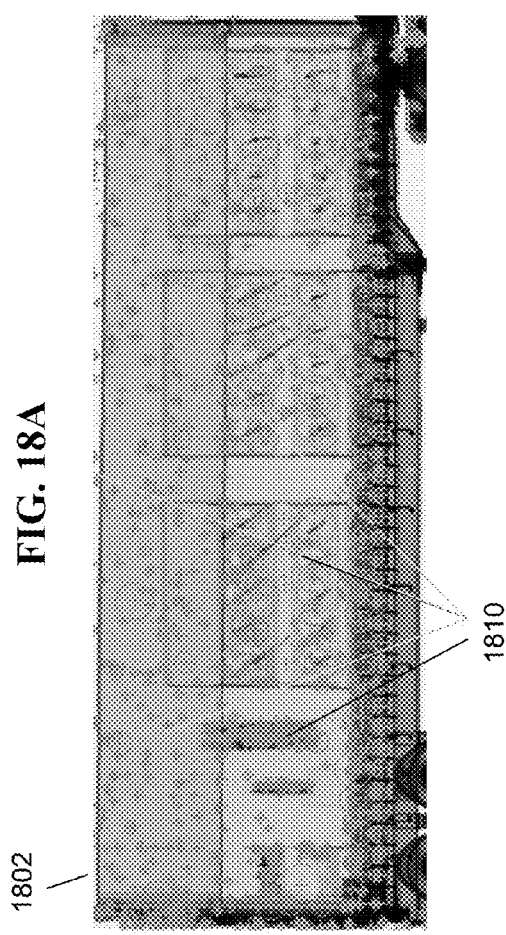
FIG. 18C illustrates the radiographic image of FIG. 18A comprising a plurality of MSER features marked thereon, in accordance with an embodiment of the present specification.

Hence, in an embodiment, at step 1704 in order to compare the radiographic image with a predefined template, using the MSER method, a predefined set of features are marked in both the template and the radiographic image, and then are compared together to obtain a feature set match. FIG. 18A illustrates an exemplary radiographic image of a cargo container 1802 comprising firearms 1804 imaged at various orientations. FIG. 18B illustrates an exemplary firearm template image comprising a plurality of features marked thereon, in accordance with an embodiment of the present specification. In an embodiment, the features 1806 marked on the firearm 1808 image template are determined using the MSER method. FIG. 18C illustrates the radiographic image of FIG. 18A comprising a plurality of features marked thereon, in accordance with an embodiment of the present specification. In an embodiment, the features 1810 marked on the cargo container image 1802 are determined using the same MSER method as used to mark features 1806 on the firearm image 1808 template in FIG. 18B. As can be seen in FIG. 18C a plurality of regions within the cargo container 1802 have features 1810 that are similar to features 1806 marked on the firearm image template 1808. Whether or not each of these regions in the cargo container image 1802 shown in FIG. 18C is a firearms candidate is determined by measuring the rate of change of certain image properties (P) over each incremental distance ΔL in the region. If the measured rate of change (ΔP) is within a certain range of a template value, that is, within the upper and lower thresholds, then the ΔP measurement is repeated over the next ΔL, and so on. If all measured image properties are within the respective thresholds for the template, then the region and the template are determined to be "matched", and this region is stored for further processing. However, if an image-property value is outside a template threshold range, then the region and the template are determined to be "unmatched", and the unmatched region is eliminated as a firearms candidate. In this "thresholds of minimum-intensity increments" process, the image properties, the respective thresholds, and the incremental ΔL value can be varied to optimize the accuracy of firearms-candidate identification.

Figure 18D:
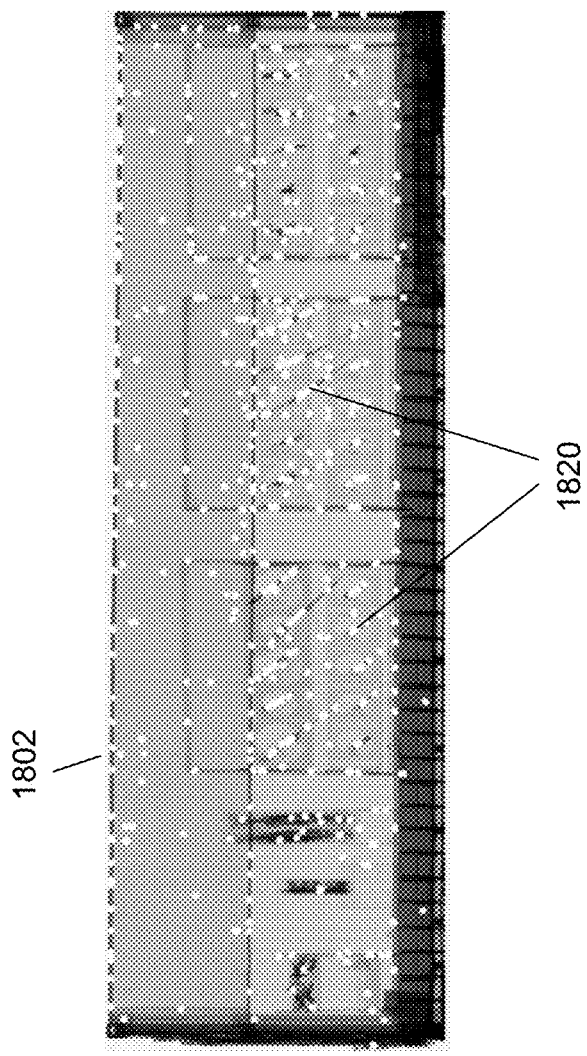
FIG. 18D illustrates an exemplary image obtained by comparing the MSER features marked in FIG. 18C with those marked in FIG. 18B, in accordance with an embodiment of the present specification.

FIG. 18D illustrates an exemplary image obtained by comparing the MSER features marked in FIG. 18C with those marked in FIG. 18B, in accordance with an embodiment of the present specification. In FIG. 18D each white dot 1820 represents an image region comprising marked MSER features that matches with a similarly marked region in the template image shown in FIG. 18B. The robustness of the MSER based image processing method of the present specification is made evident by FIG. 18D illustrating that a single firearm template (FIG. 18B) can be used to identify a variety of firearm types, orientations, and sizes. In embodiments, obtaining an exact match with a template is not necessary, because the aim is to detect firearms as a whole, not their components. In embodiments, sometimes, some regions in FIG. 18D may be identified falsely as firearms, due to reasons such as, the use of imperfect template regions, the match threshold distance being too large, or certain image regions possessing characteristics similar to a firearms image.

In embodiments, similar to the process described above for cargo containers, for the detection of firearms in vehicles and in driver cabs of tractor units, a set of templates is used to generate MSER features used in a template-matching step as detailed with reference to step 1704 of FIG. 17. In an embodiment of the present specification, for cargo containers containing large quantities of cargo, an attenuation radiographic image is used for analysis, rather than a transmission radiographic image, in order to obtain accurate results.

Referring back to FIG. 17, at step 1706, the results obtained at step 1704 are filtered to minimize any matching errors. In an embodiment, a filtering method such as Speeded Up Robust Features (SURF), commonly known in the art, is used to identify salient features in the radiographic image shown in FIG. 18A. The SURF method is a fast and robust algorithm for local, similarity invariant representation and comparison of images. Similar to many other local descriptor-based approaches, using the SURF method, interest points of a given image are defined as salient features from a scale-invariant representation. Such a multiple-scale analysis is provided by the convolution of the initial image with discrete kernels at several scales (box filters). The filtering method also comprises building orientation invariant descriptors, by using local gradient statistics (intensity and orientation). The main advantage of using the SURF method for filtering the results obtained at step 1704, lies in its fast computation of operators using box filters, thus enabling real-time applications such as tracking and object recognition.

Figure 18E:
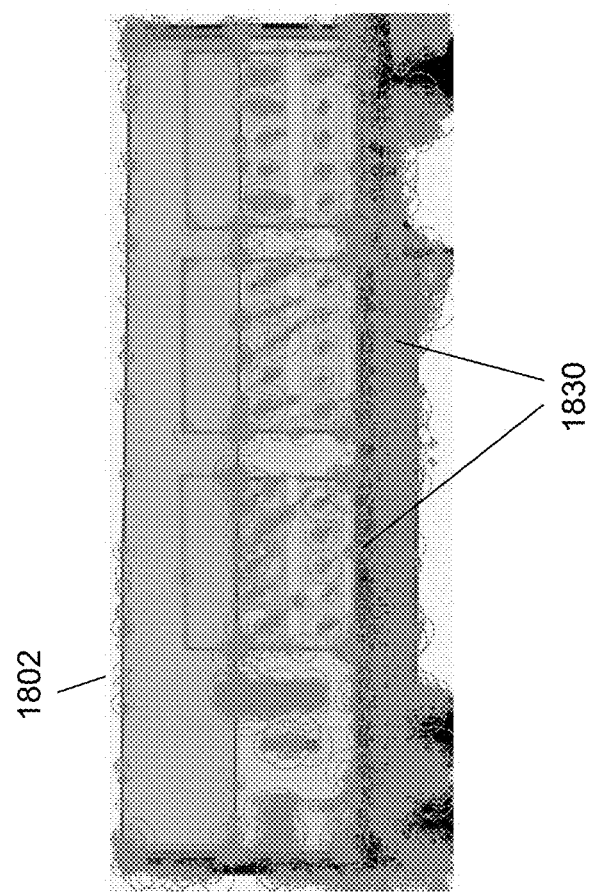
FIG. 18E illustrates the radiographic image of FIG. 18A with markings representing Speeded Up Robust Features (SURF), in accordance with an embodiment of the present specification.

In an embodiment, at step 1706, salient/SURF features are identified in the radiographic image shown in FIG. 18A. FIG. 18E illustrates the radiographic image 1802 of FIG. 18A with markings 1830 representing SURF features, in accordance with an embodiment of the present specification. Since the MSER and SURF techniques generate different features, requiring a positive result from both, i.e., applying a MSER "and" SURF logic to each image region obtained at step 1704, reduces the matching error without compromising detection (true matches). As can be observed in FIG. 18C, a plurality of MSER feature markings 1810 are present near the ceiling of cargo container 1802, while in the image illustrated in FIG. 18E a plurality of SURF markings 1830 are found in the floor region of cargo container 1802. By application of the filtering method both these regions (floor and ceiling) having plurality of markings are discarded as an "AND" logic operation is applied. The application of both the MSER and SURF image processing techniques greatly enhances the probability of accurate detection of firearms as compared to prior art methods using only one type of image processing technique.

Figure 18F:
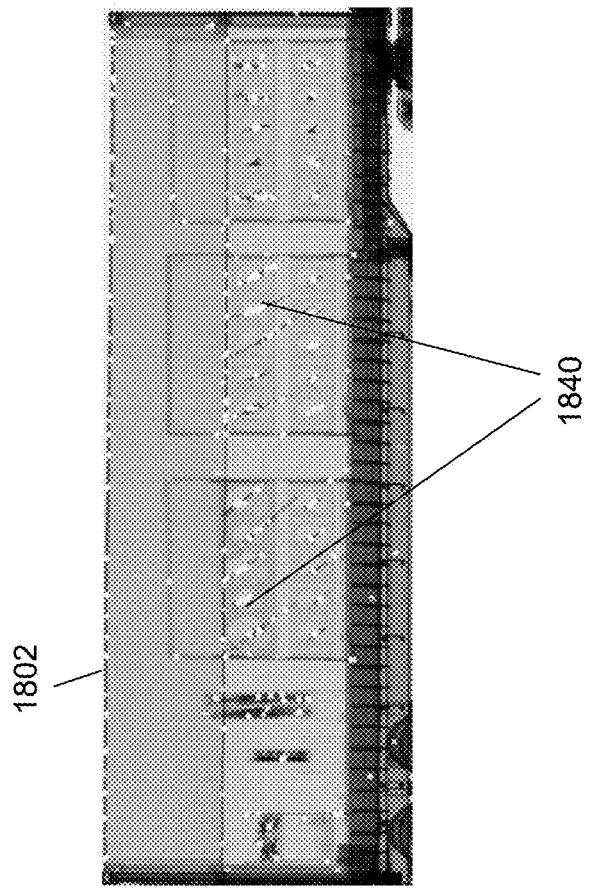
FIG. 18F illustrates a filtered version of the radiographic image shown in FIG. 18D after application of a filtering method, in accordance with an embodiment of the present specification.

FIG. 18F illustrates a filtered version of the radiographic image shown in FIG. 18D after application of the filtering method, in accordance with an embodiment of the present specification. In FIG. 18F, each white dot 1840 represents an image region containing a possible firearm. The filtering process eliminates a plurality of matching errors. Comparison of FIG. 18F with FIG. 18D shows a significant reduction in the matched image regions denoting possible firearms. Further, in an embodiment, some feature markings present along the roof line shown in FIG. 18F, which actually represent matching errors, can be filtered out by applying image processing, wherein the first step is to determine that these markings are located on the roof lines of the container. The roof lines can be identified by their geometric locations with respect to the overall container, and by the uniformity of transmission and attenuation values along the lines. Then, if the regions are isolated within the roof line, and do not extend with template-like properties beyond the roof line, they can be eliminated from consideration as a firearm.

In an embodiment, another filtering method known in the art as Deep Belief Method (DBM) that utilizes a deep neural network composed of inter-connected multiple layers of feature variables may be used at step 1706. DBM is a machine-learning method and may further reduce the template-matching errors.

In embodiments, various other filtering methods may be used in case the radiographic image being analyzed comprises vehicles and driver cabs. These conveyances tend to contain greater clutter density than cargo containers, resulting in more obstructions. In addition, the images typically include engines, steering wheels, seats, glove compartments, and vehicle frames, and identification of these structures and their spatial relationships help to reduce matching errors. For example, using attenuation-based segmentation techniques, the engine can be extracted out, and its surrounding area can be identified by combining the information of the vehicle frame and the engine location. With this information, some template-matching errors associated with the vehicle or tractor-unit structure can be eliminated. Moreover, using the engine-location information together with the segmented passenger-seat information, their relative position can be established to provide the passenger leg-room area. Since vehicle leg-room imagery is invariant, any matched objects within this region would be more highly scrutinized.

At step 1708, once the filtering process is completed, additional properties of the filtered image regions are extracted and used as features for classifications. In embodiments, properties such as effective density, attenuation and associated standard deviation, and geometric properties such as size, area, and aspect ratio, may be extracted. Although these properties are common to all kind of conveyances, in different embodiments, unique classifier routines are applied to each. After the classification performed at step 1708 a set of image regions comprising firearm possibilities are obtained.

Figure 18G:
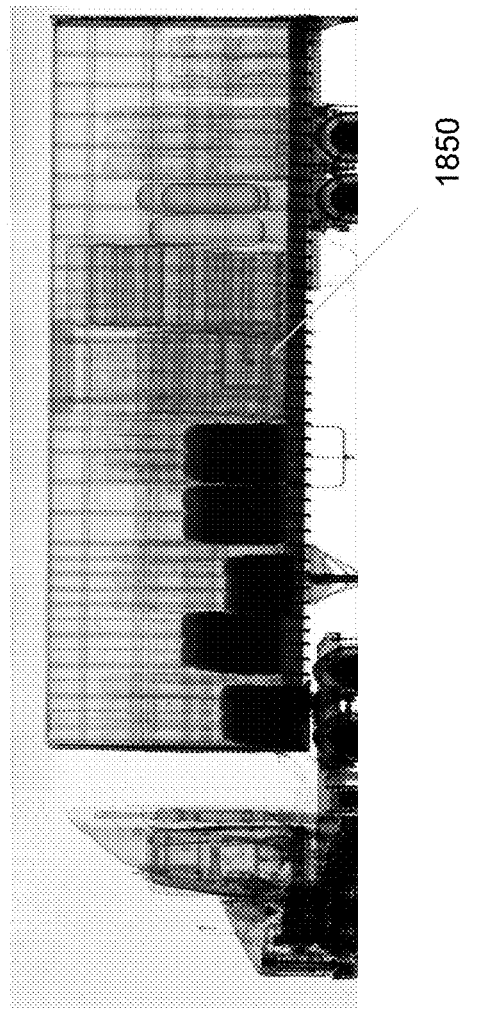
FIG. 18G illustrates a radiographic image of a cargo container after application of a marker box, in accordance with an embodiment of the present specification.

At step 1710, for each image region obtained at step 1708, a marker box is produced and laid upon the image region in the radiographic image under inspection to communicate an alarm location. FIG. 18G illustrates a radiographic image of a cargo container after application of the marker box, in accordance with an embodiment of the present specification. As shown, marker box 1850 is placed on the radiographic image of a cargo container denoting a location comprising firearms.

In another embodiment, the present specification discloses a system for automatically detecting the presence of currency, when a cargo container or a light vehicle is being inspected using non-intrusive X-ray imaging techniques. This allows the operator or inspector to quickly ascertain and verify the contents of the cargo container or vehicle that is currently being inspected. In one embodiment, the system described in the present specification automatically applies detection algorithms to the image and provides alerts to operator if it detects the presence of currency. In one embodiment, images of the cargo generated during a scan by an X-ray based inspection system are analyzed for specific features and parameters characteristic of currency, such as size, shape, texture, density, atomic number, and the location within the container or vehicle. This functionality enables security personnel to identify contraband more efficiently, without requiring opening or manual search of every container being inspected.

In one embodiment, the system of present specification provides several automated tools to make the image-inspection process more efficient and effective. These tools provide assistance to image operators in analyzing the images for contraband, particularly currency and also help in verifying that the cargo being carried is the same as declared in the cargo's manifest.

One of ordinary skill in the art would appreciate that the aforementioned automated tools can operate on any computing platform associated with the X-ray scanning system including, but not limited to: a laptop or tablet computer; personal computer; personal data assistant; cell phone; server; embedded processor; DSP chip or specialized imaging device capable of executing programmatic instructions or code.

It should further be appreciated that the platform provides the functions described in the present application by executing a plurality of programmatic instructions, which are stored in one or more non-volatile memories, using one or more processors and presents and/or receives data through transceivers in data communication with one or more wired or wireless networks.

It should further be appreciated that each computing platform has wireless and wired receivers and transmitters capable of sending and transmitting data, at least one processor capable of processing programmatic instructions, memory capable of storing programmatic instructions, and software comprised of a plurality of programmatic instructions for performing the processes described herein. Additionally, the programmatic code can be compiled (either pre-compiled or compiled "just-in-time") into a single application executing on a single computer, or distributed among several different computers operating locally or remotely to each other.

Figure 21:
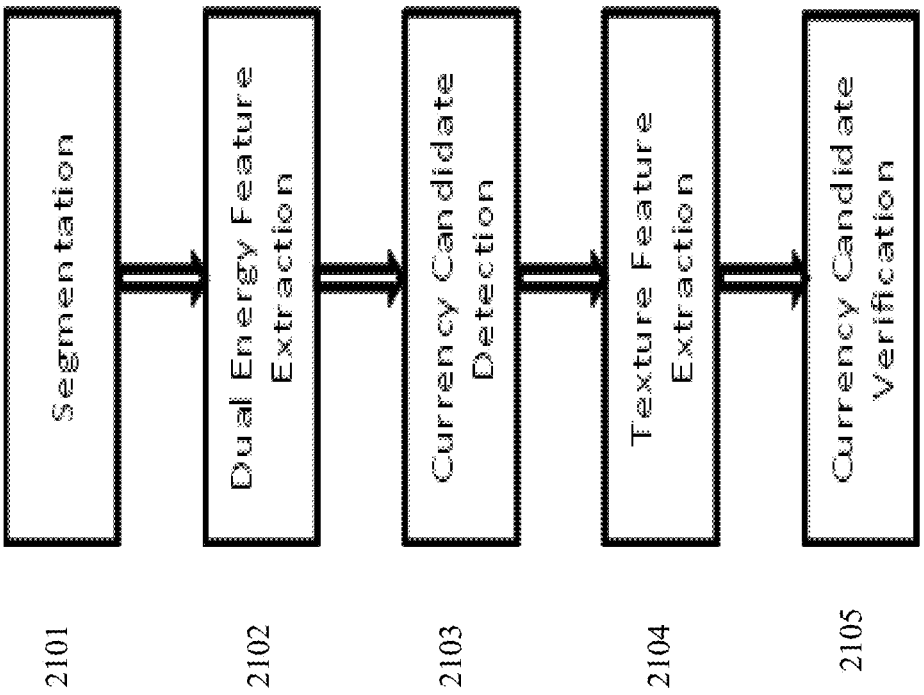
FIG. 21 is a flowchart illustrating a method of detecting currency, according to one embodiment of the system described in the present specification.

FIG. 21 is a flowchart illustrating a method for identifying the presence of currency in an image of a scanned cargo container or vehicle, according to one embodiment of the present specification. Referring to FIG. 21, the first step 2101 of the method involves segmentation of the input image. The input image is the transmission X-ray image and represents the average of the high energy (HE) channel and low energy (LE) channel, which provides density and material discrimination information (atomic number). In one embodiment, the present specification uses a watershed segmentation method to segment the input image into meaningful physical objects based on the gradient magnitude.

The next step 2102 involves a dual-energy feature extraction. As explained earlier, the X-ray scanning system used with the present specification employs a dual energy method of scanning, which is useful for material discrimination. In step 2102, the following features are extracted for each segmented object obtained from the input image in step 2101:

a) Average Intensity: (HE+LE)/2
b) Intensity Difference: HE−LE
c) Mu Ratio: ln(HE)/ln(LE)
d) Mu Diff: ln(HE)−ln(LE)
e) Zeff (effective atomic number) estimated from the standard lookup table (LUT)
f) Zeff estimated from a new lookup table (LUT) generated by Mu Ratio Where HE=High Energy channel and LE=Low Energy Channel.

One of ordinary skill in the art would appreciate that the above characteristics of objects in the image help in classifying the objects as being organic, inorganic, metallic, radioactive, etc., and also help in identifying the particular material composition of each segmented object. Further, the above features are determined (using various functions of the high energy and low energy values) and those determined features are compared against a values from a database storing feature values which have been previously determined for actual currency. In one embodiment, X-ray data is collected for vehicles that contain currency, and features specific of currency are established through analysis. In operation, these features are measured for the object under scan and compared to the established currency specific features.

In step 2103, currency candidate detection is performed. In this step, potential currency or currency-related objects are identified by thresholding the dual-energy features extracted in step 2102. In one embodiment, thresholds are established through analysis of x-ray images that contain currency in realistic environments, and through analysis of potential false-positive candidates.

In step 2104, texture feature extraction is performed. In one embodiment, the following second-order histogram-based texture features are extracted for each potential currency object identified in the previous step:

a) Energy
b) Entropy
c) Inverse different moment
d) Inertia
e) Cluster shade
f) Cluster prominence In the following step 2105, objects identified in the previous steps that could potentially be currency or currency-related verified in order to determine currency objects. In one embodiment, to minimize false-positive detections, the dual-energy features extracted in step 2102 and the texture features extracted in step 2104 for each currency candidate are used in combination as input to a support vector machine classifier to determine whether it is a currency object.

Once a currency object is identified by the process of the present specification, an alert is issued to the operator of the scanning system so that they may take appropriate action.

In one embodiment, features and characteristics that form the basis of detection of currency and are determined as described above, are saved in a database for future reference. This image data can be referred by the scan operators to determine if a cargo currently being scanned has the features characteristic of currency. In one embodiment, these processes of saving relevant image data to the database and comparing the data with current images are integrated with the automated process of currency detection and help to substantially reduce false positives. These processes are illustrated by means of flowcharts in FIGS. 22 and 23.

Figure 22:
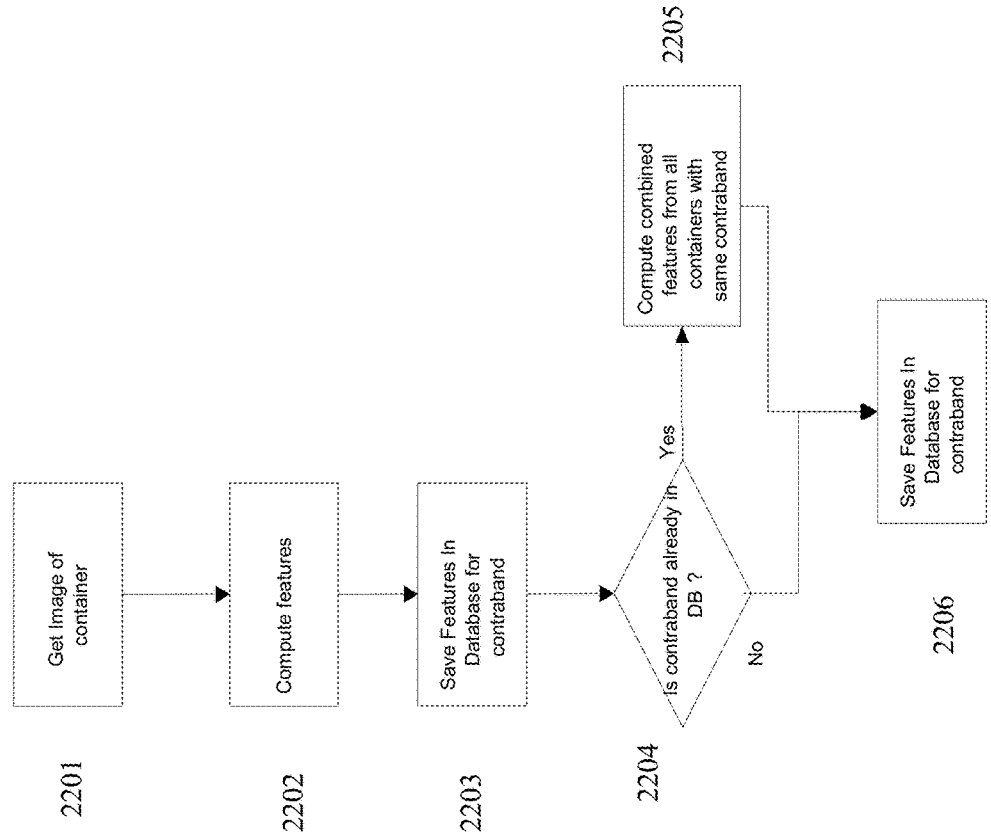
FIG. 22 is flowchart illustrating one process for preparing a features database, according to one embodiment of the system described in the present specification.

FIG. 22 is a flowchart showing a process of preparing a features database. In the first step 2201, the system obtains the image of the container. The image is obtained through non-intrusive scanning by using a suitable scanning system, as described above. In one embodiment, radiographic images are generated that contain atomic-number information generated from any modality of dual-energy or dual-species inspection. The images could be generated by one or more views and could be three dimensional reconstructed from the views.

Thereafter, features of the image are computed, in step 2202. The process of computing features is explained above with reference to steps 2102 through 2104 in FIG. 21. In the next step 2203, computed features and their standard deviations are then saved in the database along with the number of images used to compute the features, and are associated with the particular contraband, which in this case is currency. In one embodiment, specific codes are assigned to different types of contraband to help associate specific features with them.

In one embodiment, the computed features include, but are not limited to, attenuation, texture, atomic number, elemental composition and/or cargo height. For tomographic and multi-view systems, density is also a useful feature. It should be understood by those of ordinary skill in the art that other features not listed here could be used to match the cargo images.

In the next step 2204, the system checks if any entries for that contraband are already stored in the database. If so, the system combines features from the containers with same type of contraband. This is shown in step 2205. The combination of the feature values takes into account the number of images used to compute the feature value and is weighted accordingly. Also, the user is notified of outlier feature values (values that are outside the three standard deviations or other selected range) for acceptance before the combination takes place. Thereafter the combined set of features for that particular contraband is saved in the database, as shown in step 2206. Thus, the features saved in the database per contraband are computed from a combination of feature values from a large number of cargo images found with the same contraband. The feature values are updated as additional cargo images are collected. Additional features can also be used computed as their usability becomes available.

Figure 23:
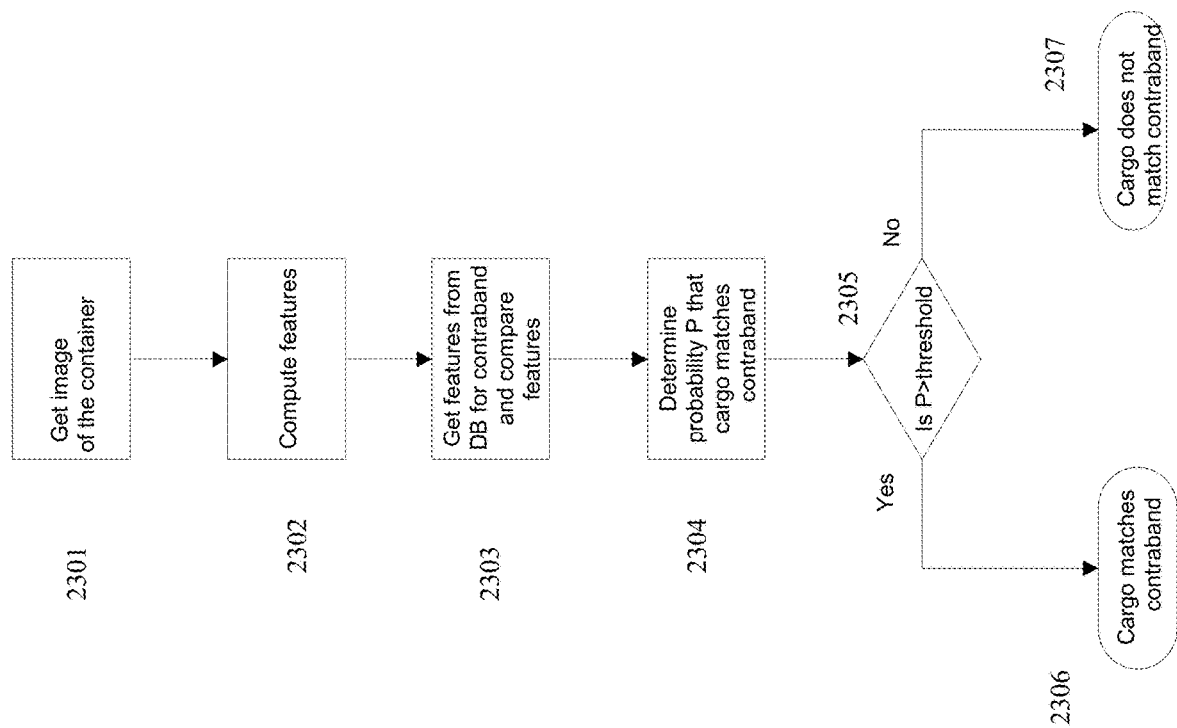
FIG. 23 illustrates the use of the features database described with respect to FIG. 22 to determine if cargo under inspection carries a specific contraband.

FIG. 23 illustrates a method for comparing images of an individual cargo container with the database of contraband features. In the first step 2301, an image is captured by the cargo scanning system. Then, the features of the image are computed, in step 2302. Thereafter, the system obtains features for a specific contraband, such as currency, stored in a database, and compares them to the computed features. This is shown in step 2303. The system then determines the probability 'P' that some contents of cargo match the contraband, in step 2304. Probability 'P' is then compared to a threshold value in step 2305. If 'P' is greater than the threshold value, it implies that some contents of the cargo match with the features of the specific contraband, as shown in step 2306. If 'P' is less than the threshold value, it indicates that the contents of the cargo are not the same as the specific contraband, as shown in step 2307.

In one embodiment, the threshold value may be determined in accordance with the user's preferences. For example, if custom office is using the system and they want to detect most contraband even at the expense of higher false alarm rate, they may be able to set a high threshold value, such as 90%. Conversely, if the custom agency does not want to have a high false alarm rate, they can choose to set a low threshold value, such as 60%. Further, the customer may decide that some categories of goods are more important, such as those associated with higher duties, than others and place different thresholds for different types of goods.

Further, before flagging cargo, a predetermined minimum set of images may be used to compute the features. The customer may decide that the features database is complete and more images do not need to be used. In this case, there is no need to add more images to the database. However, if the database did not use enough images, or the customer wants to improve the accuracy of detection, an authorized operator can request to add more images to the database.

In one embodiment, the system provides additional tools that help in the detection of currency carried in cargo. In one embodiment, an operator assist tool helps to determine when a cargo does not match manifest, thereby indicating presence of contraband. This tool helps in detecting situations such as cargo density being too low or too high for declared cargo, presence of organic material in cargo when manifest cargo is metallic or vice-versa and cargo being too uniform or heterogeneous for declared cargo, for example when an image shows high-density areas which are not compatible with a declared cargo of clothing. In other embodiments, tools for operator assistance include but are not limited to, automatic verification that a container/trailer/rail car is empty; Detection of hidden compartments; and Pallet counting.

Empty Container Verification

The goal of this tool is to verify that a cargo container is empty, and if the container is empty, to eliminate the need for the operator to view the image. Thus, this feature helps in improving operational efficiency of the scanning system. In one embodiment, the definition of not empty is the detection of any object greater than a specified size that attenuates the beam by a specified value. For example, any object greater than 1 cm in any direction that attenuates the beam by more than 5%. Other specifications as minimum detectable mass are also possible.

It may be noted that either the container and/or the system could be slightly tilted, increasing the width at the edges. Also, the truck might be passing through the system at different angles. Also, sometimes images contain artifacts due to bad detectors or linac instabilities. The algorithm for empty container verification takes into account these variations in one embodiment, and further is able to analyze container of any size, detect multiple containers and verify each of them separately.

The empty container verification tool is also useful in detecting more difficult cases of contraband smuggling, where the image of container structure may mask contraband. Examples of this type of smuggling include currency placed in door frames, door panels, container frame, corner blocks or other cases.

Figure 24:
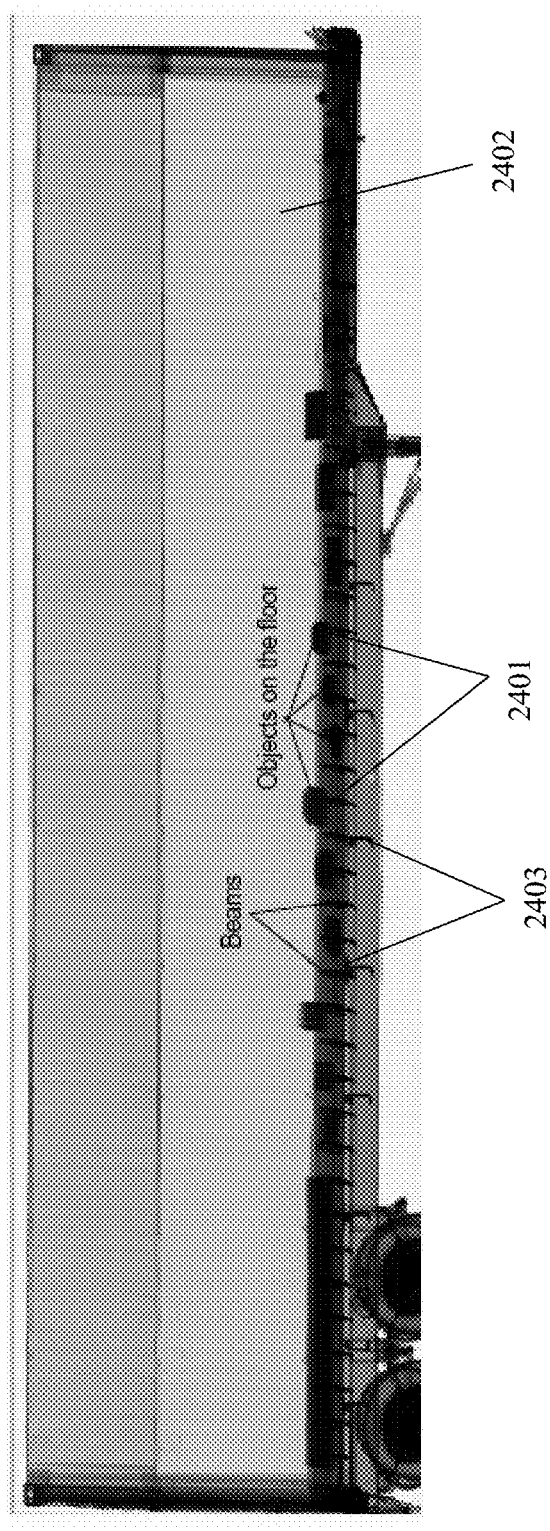
FIG. 24 shows an exemplary case of use of an empty container verification tool.

FIG. 24 shows an exemplary case where the empty container verification tool detects objects 2401 placed on the floor of the container 2402. The algorithm uses parallax to detect objects on the floor without alarming on container structure, such as beams 2403 and other truck support hardware. In the same manner, the tool is able to detect objects placed under the floor as well.

Cargo Uniformity

Figure 25A:
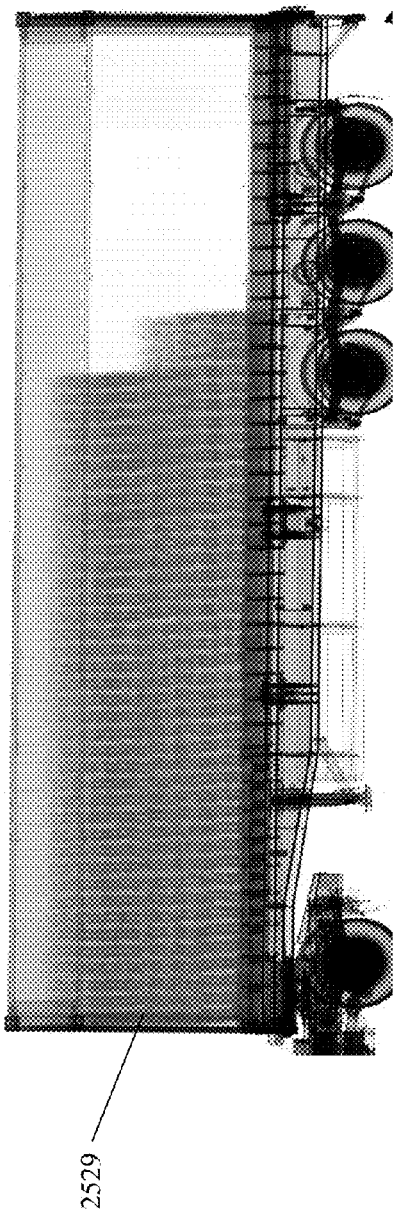
FIG. 25A shows an example of a uniform cargo.
Figure 25B:
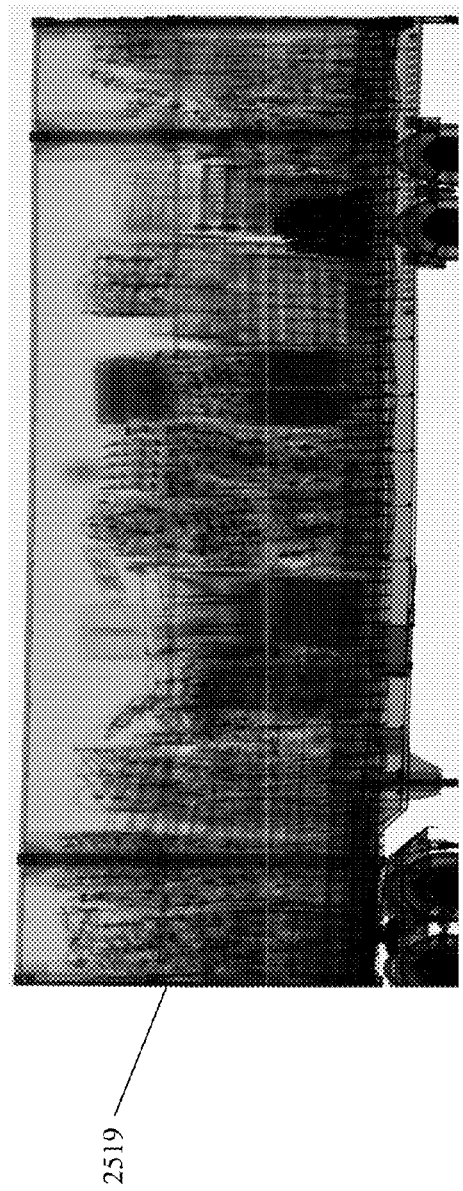
FIG. 25B shows an example of a non-uniform cargo.

One the methods to perform cargo-manifest verification and determine the presence of contraband such as currency, is to check whether a cargo that is supposed to be uniform, also shows a uniform image. In one embodiment, a cargo database specifies which cargos are supposed to be uniform and the cargo uniformity tool alarms if the image is inconsistent with the manifest. Examples of uniform 2529 and non-uniform 2519 cargos are shown in FIGS. 25A and 25B, respectively.

In one embodiment, the algorithm for cargo uniformity is configured to detect uniformity based on a scale parameter "granularity". The average density can also be used to verify the cargo type.

Material Discrimination

In one embodiment, dual-energy images are used for cargo manifest verification by checking whether the cargo is mainly organic, mainly metallic or combination. The images are then compared with the material type declared in the cargo manifest.

Anomaly Detection

In one embodiment, anomalies are automatically detected when the cargo is homogeneous and minimum characteristics of the cargo are specified. The algorithm relies on this information to detect any contraband concealed in the homogeneous cargo.

Figure 26:
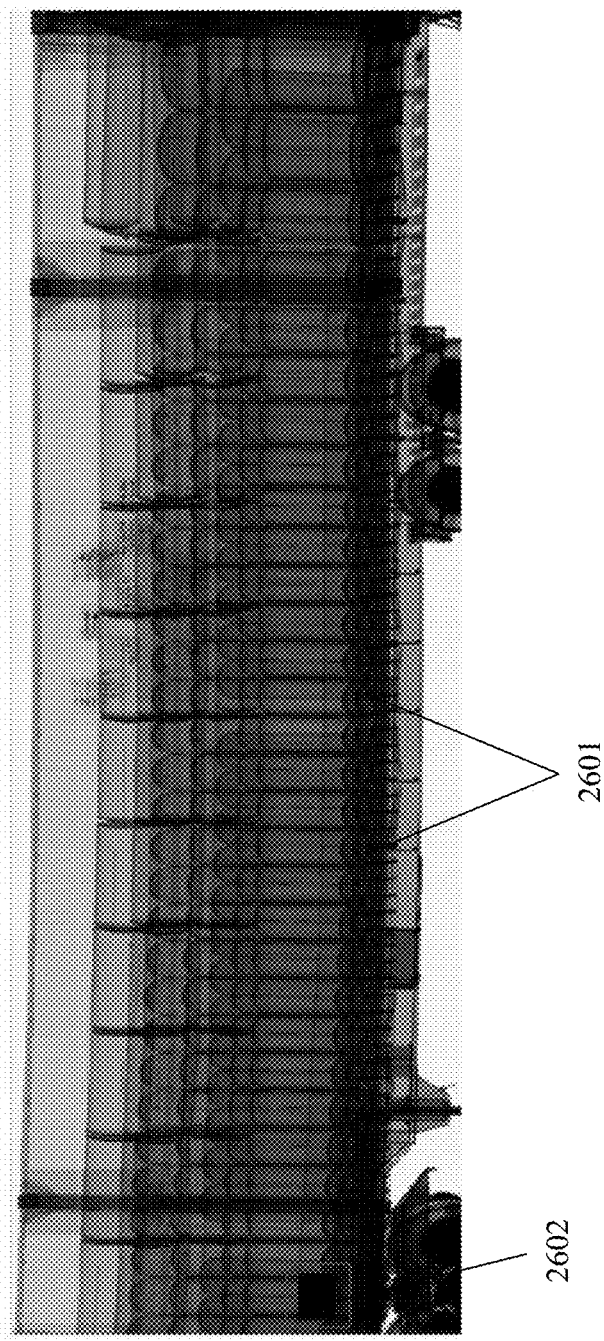
FIG. 26 shows an exemplary case of anomaly detection in periodic cargo.

In one embodiment, anomalies are further automatically detected in periodic cargo. An exemplary case of periodic cargo is illustrated in FIG. 26. Referring to FIG. 26, the detection algorithm does not produce an alarm with repetitive objects 2601, but generates an alarm with an object 2602 of different attenuation or shape.

Pallet Anomalies

In one embodiment, data from manifest and cargo database are used to automatically identify anomalies such as hidden currency inside large bags that are used to carry dry groceries. The operator assist algorithm in this case determines whether the pallet should be homogeneous, and generates an alarm if it is not.

Figure 27:
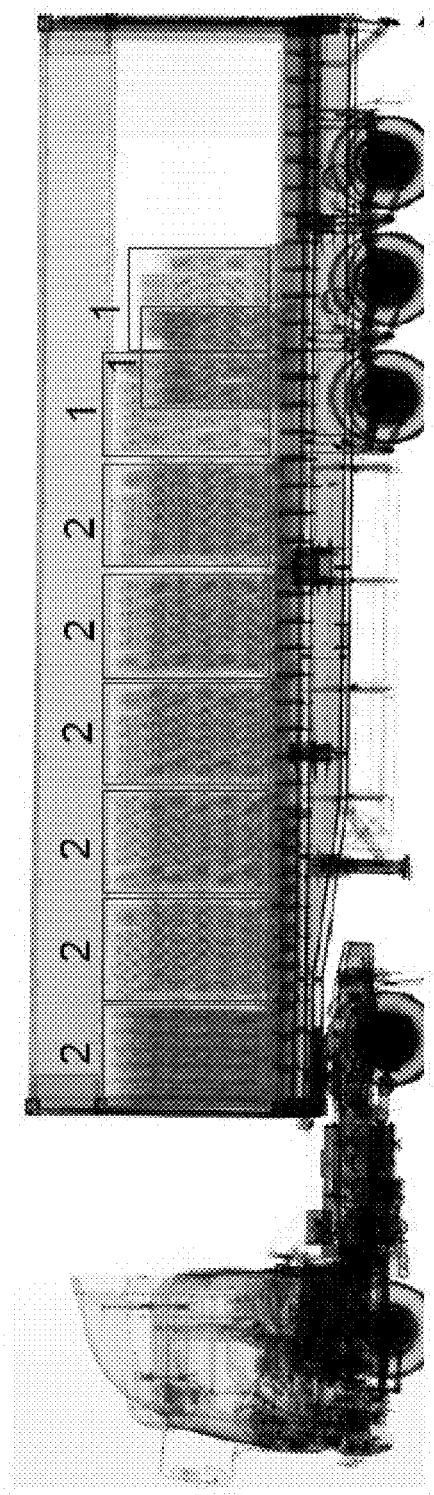
FIG. 27 illustrates an exemplary image with pallet counting.

In some cases, it is useful to count the number of pallets to determine whether the shipper declared them all. In one embodiment, an automated tool detects the total number of pallets and indicates the corresponding locations of detected pallets. In one embodiment, the tool is able to determine when some pallets are placed behind others. FIG. 27 illustrates an exemplary image with pallet counting. As can be seen from the figure, the algorithm is sufficiently sophisticated to determine when pallets are placed behind others.

In one embodiment, an operator assist tool identifies the cargo types in the container. This is useful in cases where the manifest indicates more than one cargo type. As an example, in the image of a container carrying three cargo types, each of the cargo types may be indicated with a different color. One of ordinary skill in the art would appreciate that any other means for indication may be employed to illustrate different types of cargo.

In one embodiment, various operator assist tools may employ pattern recognition algorithms to detect and identify the type of contraband, including currency.

Image Comparison

Figure 28:
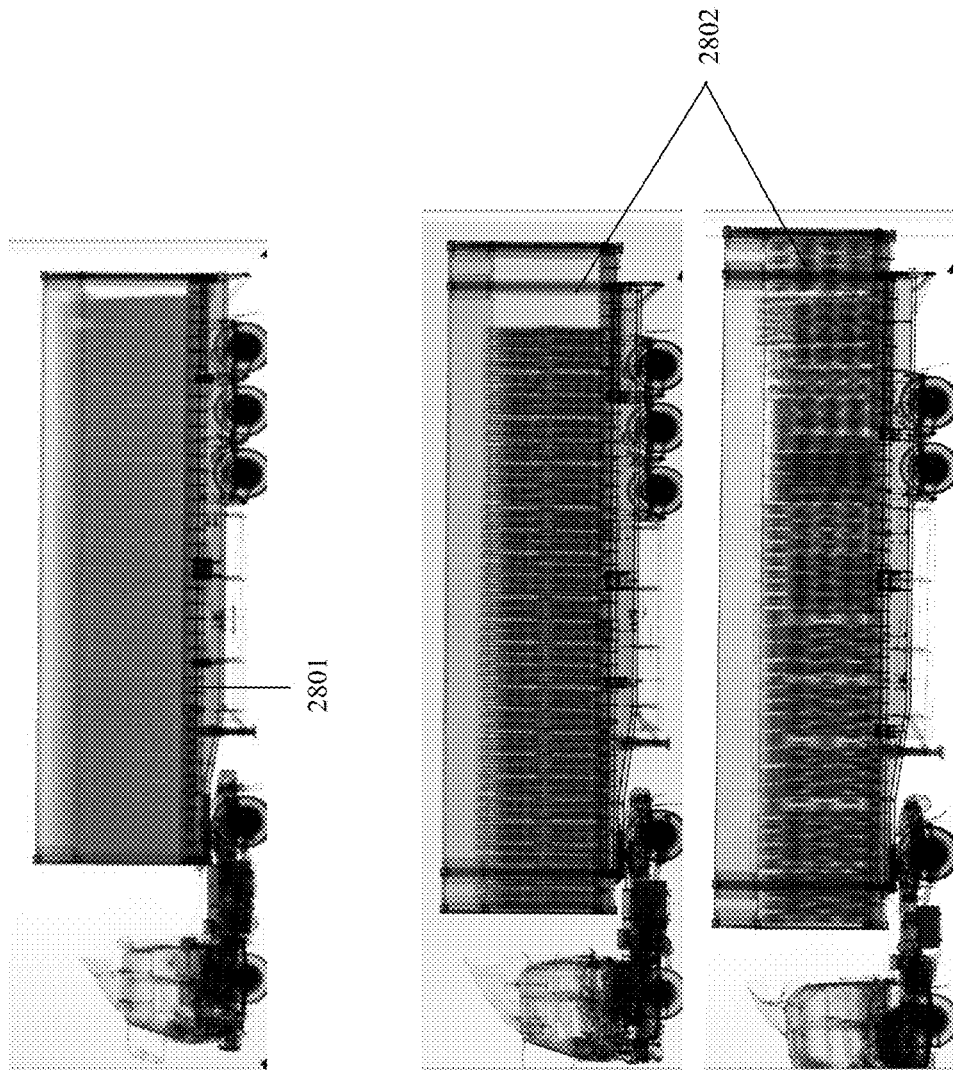
FIG. 28 illustrates how scanned images may be visually compared with images from a database to determine if cargo matches the manifest, according to one embodiment of the present specification.

This assistance tool allows the operator to invoke a number of images of certain type of cargo previously acquired and compare them with the image under analysis. This helps the operator in determining whether a cargo image matches the manifest, and indicates the potential presence of contraband if the present image is very different from the images in the database. This is shown in FIG. 28, wherein the current image 2801 of the cargo can be visually compared by the operator with images 2802 of the same cargo type from the image database. Additional assistance is provided by displaying values of various cargo features of the current and previously imaged cargo. In the example, shown, and by way of example only, the current image 2801 is different from the database images 2802. Thus, the operator should make a decision that the cargo does not match the manifest, because the current image is different from those in the database.

In various embodiments, operator assist tools are also useful in cases where contraband is concealed in parts of the truck other than the container or trailer—for example, when currency is concealed in the spare tire of a truck.

In one embodiment, an operator assist tool allows the operator to request images and analysis results, including past seizures, from previous inspections of a shipper or vehicle with same ID. This historical data helps the operator or automated software to provide a more intelligent decision.

In another embodiment, the present specification discloses an automated method of threat detection based on processing and comparison of the X-ray images of a vehicle over time. In one embodiment, the present system provides an automated means to detect differences between sequential x-ray inspections of the same vehicle.

X-ray screening of vehicles is often utilized at checkpoint entrances to Government facilities to search for illicit cargo such as drugs, weapons, and explosives. In many instances, a vehicle will pass through the same checkpoint on a regular basis. While the cargo within this vehicle will change from visit to visit, the vehicle structure (chassis, fuel tank, etc.) is expected to remain unchanged. Automated detection of differences in vehicle structure through inspection of sequential x-ray images of the same vehicle can improve security and reduce inspection times.

Figure 29:
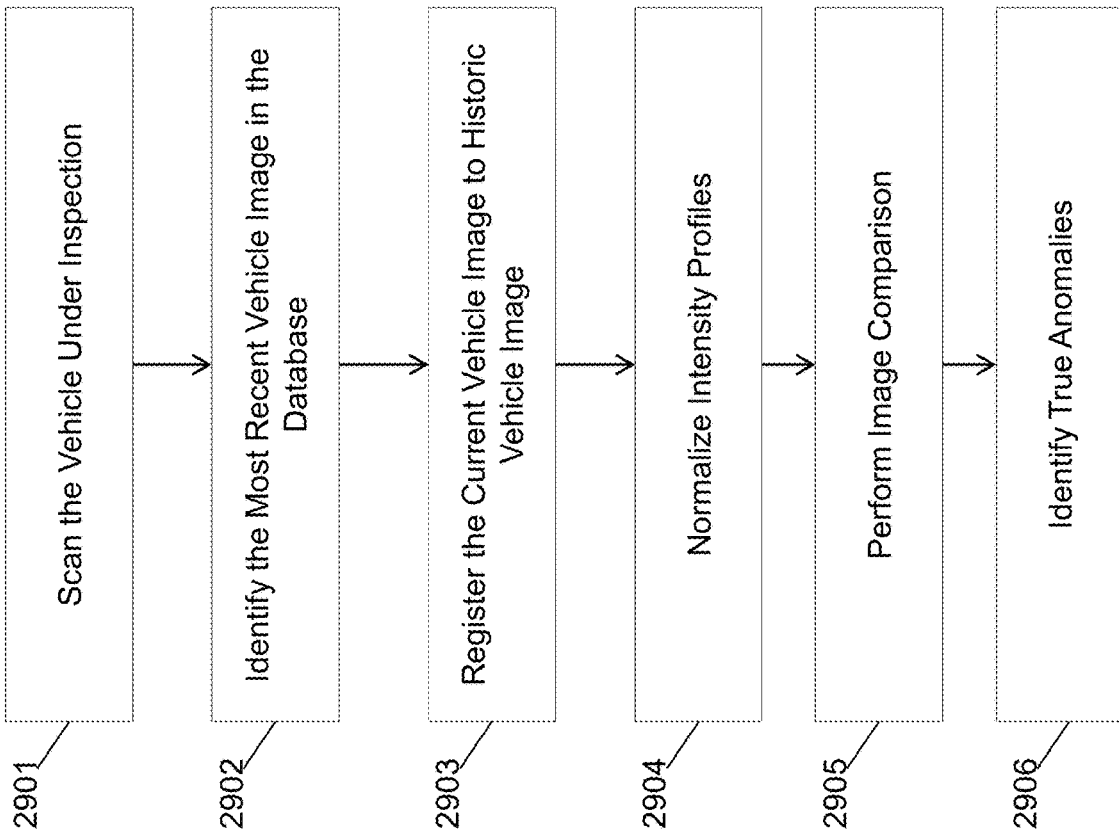
FIG. 29 is a flowchart illustrating a method of automatic threat detection, in accordance with one embodiment.

FIG. 29 is a flowchart illustrating a method of automatic threat detection, in accordance with one embodiment. Referring to FIG. 29, in the first step 2901, the vehicle under inspection is scanned using a high-energy transmission x-ray system. In one embodiment, upon entering the system, the vehicle license plate number or other vehicle identifier is read by the system's optical character recognition (OCR) software, and this unique character set is stored with the just-acquired image. In the next step 2902, the most recent vehicle image in the database is identified. For this, the system software uses the vehicle identifier to query the system database for images associated with the same identifier, and uploads the most recently-acquired of these stored images. Next, in step 2903 the current vehicle image is registered with the historic vehicle image. One of ordinary skill in the art would appreciate that a variety of image registration methods may be applied to determine the transformation that best maps the current image to the historic image.

In the next step 2904, the intensity profiles of the registered images are normalized and scaled similarly. After normalizing, image comparison is performed in step 2905. In this step, the intensity levels of the normalized images are compared on a pixel-by-pixel basis. In one embodiment, an optimized change detection algorithm is employed, wherein if the intensity difference between two pixels is greater than a predefined threshold, it is classified as a potential-difference pixel. The potential difference pixels are then clustered into potential-difference objects based on their spatial location. Finally, in step 2906 true anomalies are identified. In this step, each potential difference object is evaluated by a set of features, such as its size, location, and texture. Based on established alarm-decision criteria, the system reports the location of those potential-difference objects to the operator, which are determined to be true anomalies in need of investigation.

Image Registration Techniques

Image registration is required to compare two images of the same vehicle that differ geometrically. Differences may be due to variances in the respective scan processes, such as non-constant vehicle speed during the scan and differing magnification or view angle due to vehicle position or orientation with respect to the radiation source.

The canonical steps in image registration are detection/matching, transform model estimation, and image re-sampling. It may be appreciated that a variety of frequency-, intensity- and/or feature-based methods may be used to find matching control points to align the historic and current images. For example, a corner-matching feature-based method finds the transformation between two images by matching corresponding corners in the images. A normalized cross-correlation based method is an intensity-based method that finds the transformation between two images by finding the maximum of their normalized cross-correlation value. A priori knowledge of the geometry and ensuing transformations is essential to proper control-point selection.

The method of present specification may use one or more transformation methods, such as but not limited to, affine transformation, piecewise affine transformation, and deformable transformations. Transform model estimations under consideration include a mean-square difference, normalized correlation, and mutual information-based metrics. Both rigid transformation and non-rigid transformation methods, and their combinations, may be employed to account for the image-dimension variation between the current and the historic image due to differences in the scan geometry.

Filtering Techniques

In one embodiment, the present method uses one or more image-smoothing or filtering techniques for reducing image noise prior to the application of the change detection algorithm. Techniques that may be used include Gaussian Blur, a type of image-smoothing filter; Median Filtering, a noise-reduction technique; and Bilateral Filtering, a noise-reduction and edge-preserving technique.

Change Detection Algorithm

In one embodiment, the present method compares the current vehicle image with the historic vehicle image to identify significant differences between the two. For this purpose it makes use of one or more of the following approaches:

i) Ratio-Based Method

The observed pixel value or intensity at a location is defined as I(x, y), and then the ratio of the pixel value or intensities at location #2 to the value at location #1 can be expressed as $$R(x,y) = I_2(x,y)/I_1(x,y)$$

Where $I_2(x, y)$ refers to the current image and $I_1(x, y)$ refers to the reference image. The ratio of intensities is expected to be a constant if the vehicle did not undergo any change, and hence we can expect R(x, y) to remain constant. This suggests that we can use the variance of R(x, y) in a window around a pixel as an indication of a change between the images. If this variance is higher than an established threshold, that pixel can be labeled as a change pixel.

ii) Statistical Method

In this method, the observation D is modeled as a Gaussian random variable with zero mean and variance $\sigma^2$ under the null hypothesis $H_0$, that is, the hypothesis that there is no change between the images. D can be any difference measure. The parameter $\sigma^2$ can be estimated as the sample variance of a training dataset. Hence the conditional density function may be presented as:

$$f(D \mid H_0) = \frac{1}{\sqrt{2\pi\sigma^2}} e^{-\frac{D^2}{2\sigma^2}}$$

The null hypothesis can be accepted if $f(D|H_0)$ is greater than a threshold.

iii) Pixel Difference Method

In some embodiments, change detection is achieved by applying a pixel-difference method. On a pixel-by-pixel basis, the intensity levels of the normalized images are compared. If the intensity difference between two pixels is greater than a predefined threshold, it is classified as a potential-difference pixel.

Grouping Potential-Difference Objects

In one embodiment, potential-difference pixels are grouped into potential-difference objects based on their spatial connectivity, using a connected component labeling algorithm. This algorithm scans an image and groups its pixels into components based on pixel spatial connectivity. All pixels in a connected component have similar intensity values and are in some way connected with one other. Once all groups have been determined, each object is labeled with a gray-level or a color according to the component to which it was assigned.

Anomaly Identification

Classification methods are utilized, in one embodiment, to determine if a potential-difference object represents a true anomaly. The relevant features of a potential-difference object are classified, and objects that satisfy pre-defined classification criteria are labeled as true anomalies. For the purpose of image background subtraction and anomaly identification, some of the techniques that may be used, for example, include—Global Threshold using Otsu's Method, Adaptive threshold method, Edge-based method and Watershed-based method.

Vehicle Identification Number Capture

In one embodiment, for inspection of cargo and vehicles inspection, the present system provides an optional identification number capture system that automatically captures a license plate number, cargo container identification number, or other vehicle identification number. In one embodiment, the identification number capture system comprises cameras positioned to capture the license plate number or other identification number and OCR software that processes the camera images and extracts the ID number. The captured identification numbers are added to the corresponding inspection record.

Figure 30A:
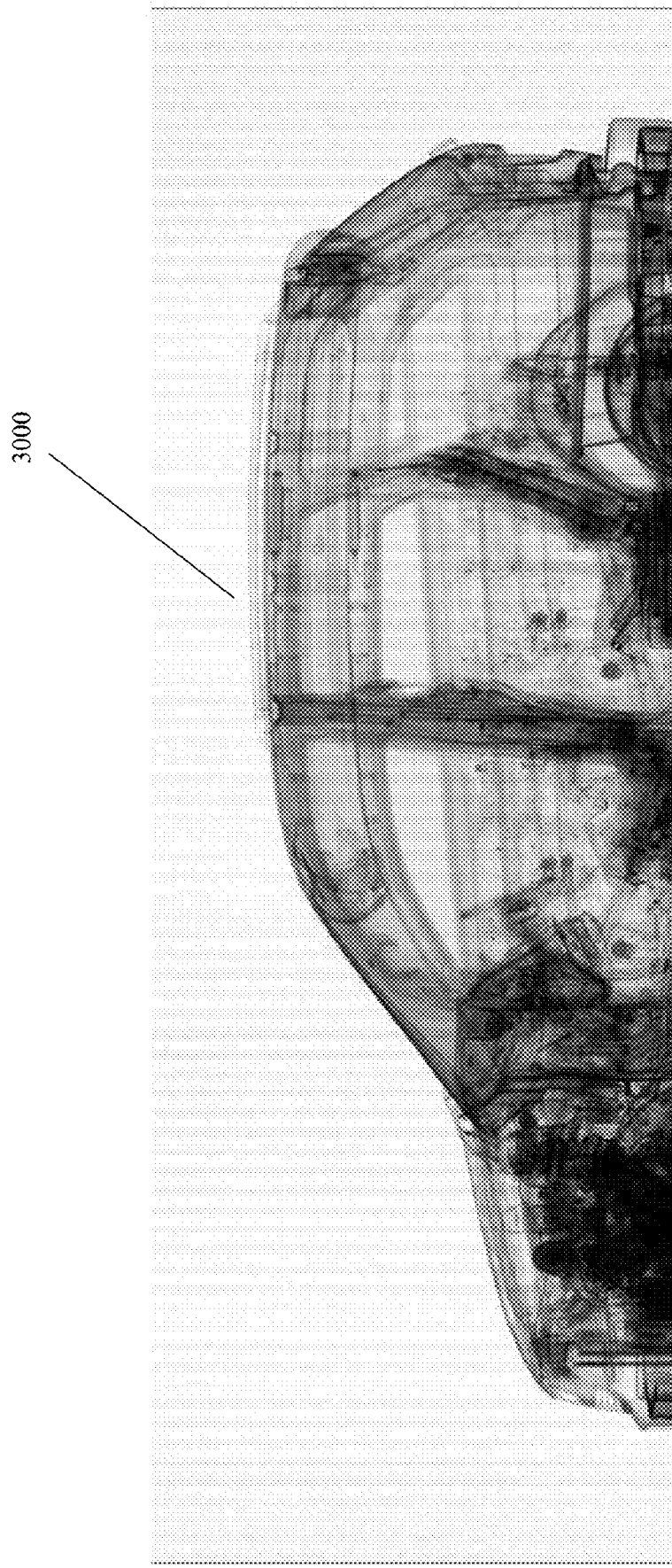
FIG. 30A illustrates a historic image of a vehicle acquired by an inspection system.
Figure 30B:
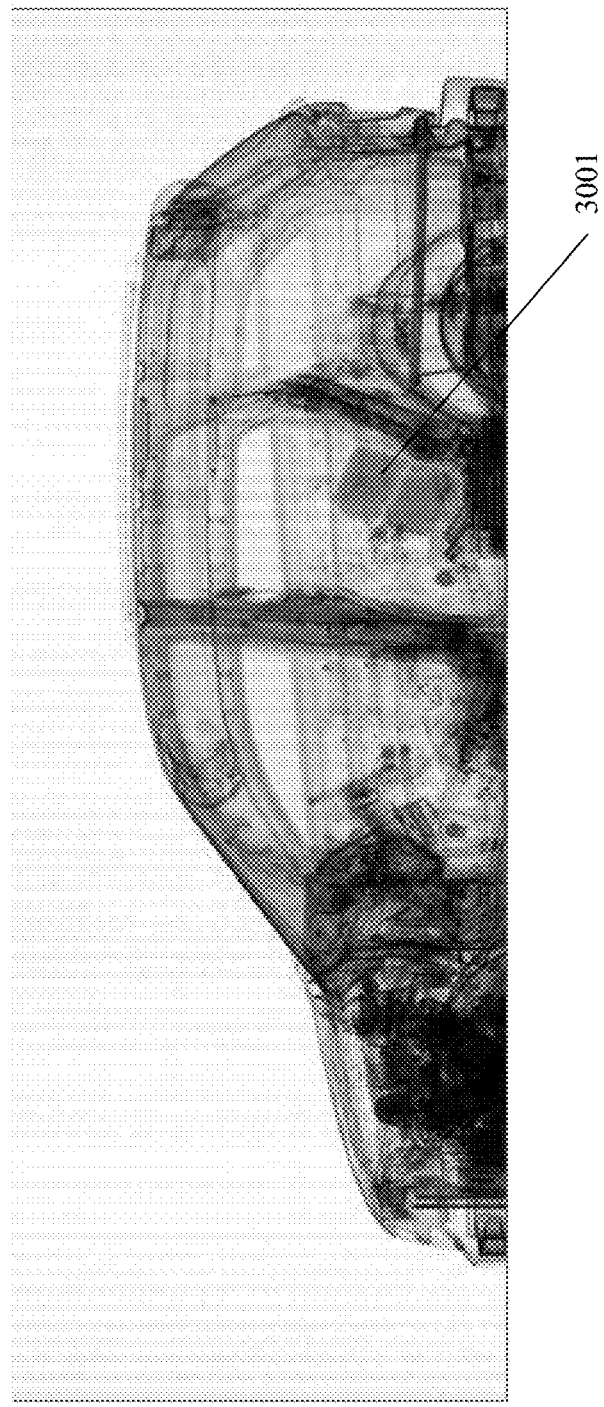
FIG. 30B illustrates the current image of the vehicle of FIG. 30A.

FIGS. 30A through 30E illustrates an example of application of the automatic detection system and method, based on image comparison. FIG. 30A illustrates an exemplary historic image of a vehicle 3000 acquired by an inspection system. FIG. 30B illustrates the current image of the same vehicle, shown by the way of example only, with a contraband item 3001. Here, the current image is transformed (registered) to the space of the historic image.

Figure 30C:
FIG. 30C illustrates the difference between the historic image and current image of a vehicle.

Next, a pixel difference method is applied, to reveal the differences between the current image and historic image. This difference image is shown in FIG. 30C. It may be noted that any non-zero differences in the image of FIG. 30C, other than at the anomaly location, are due to random noise.

Figure 30D:
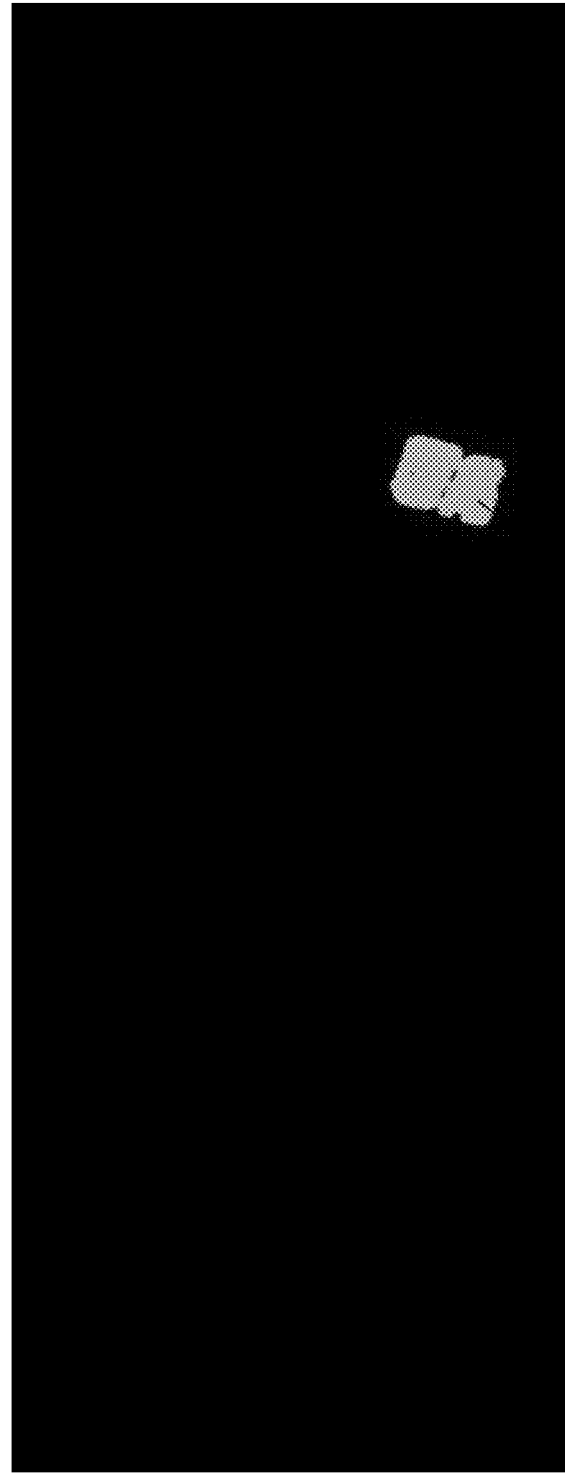
FIG. 30D illustrates contraband in an acquired and processed image.

Next, using a thresholding technique, pixel-difference values are then evaluated against an established threshold value. Only those values greater than the threshold value survive to define potential-difference objects. A classification technique is then applied to determine which potential-difference objects represent true anomalies. In the present example, the only potential-difference object to survive the classification step is shown in the image of FIG. 30D, where the contraband item 3010 is clearly visible in the image.

Figure 30E:
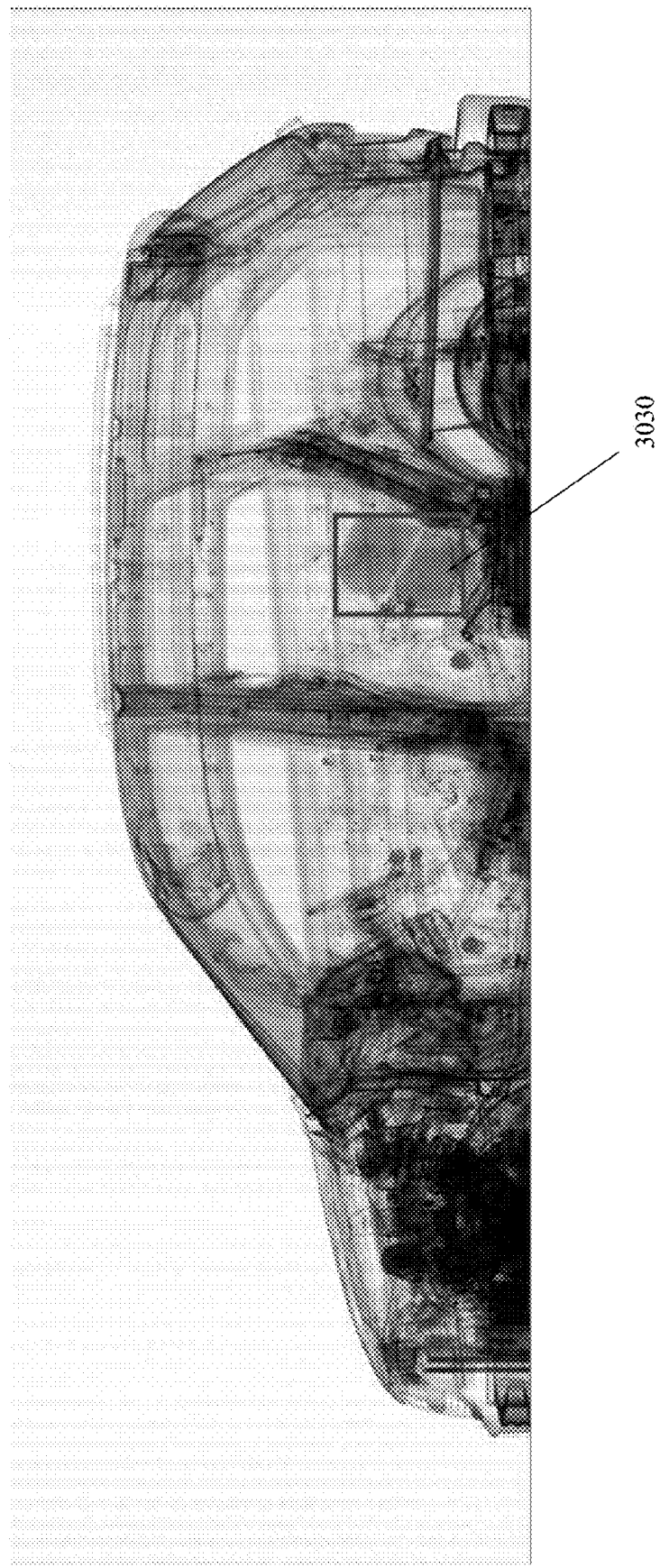
FIG. 30E illustrates an image with a contraband item marked for display.

The true anomaly is then transformed back to the space of the current image, and identified to the operator, as shown in FIG. 30E, where the contraband item 3030 is marked and presented on the display.

In one embodiment, an interface is provided for storing to, and recalling images from a database, based on vehicle identification number (VIN), license plate number, or other unique identifier. In one embodiment, the interface further comprises various operator assist tools, as described in the previous sections, to help in automatic identification of contraband and threat items. In one embodiment, the interface further comprises cargo manifest information management system and interface, as described above.

Figure 31:
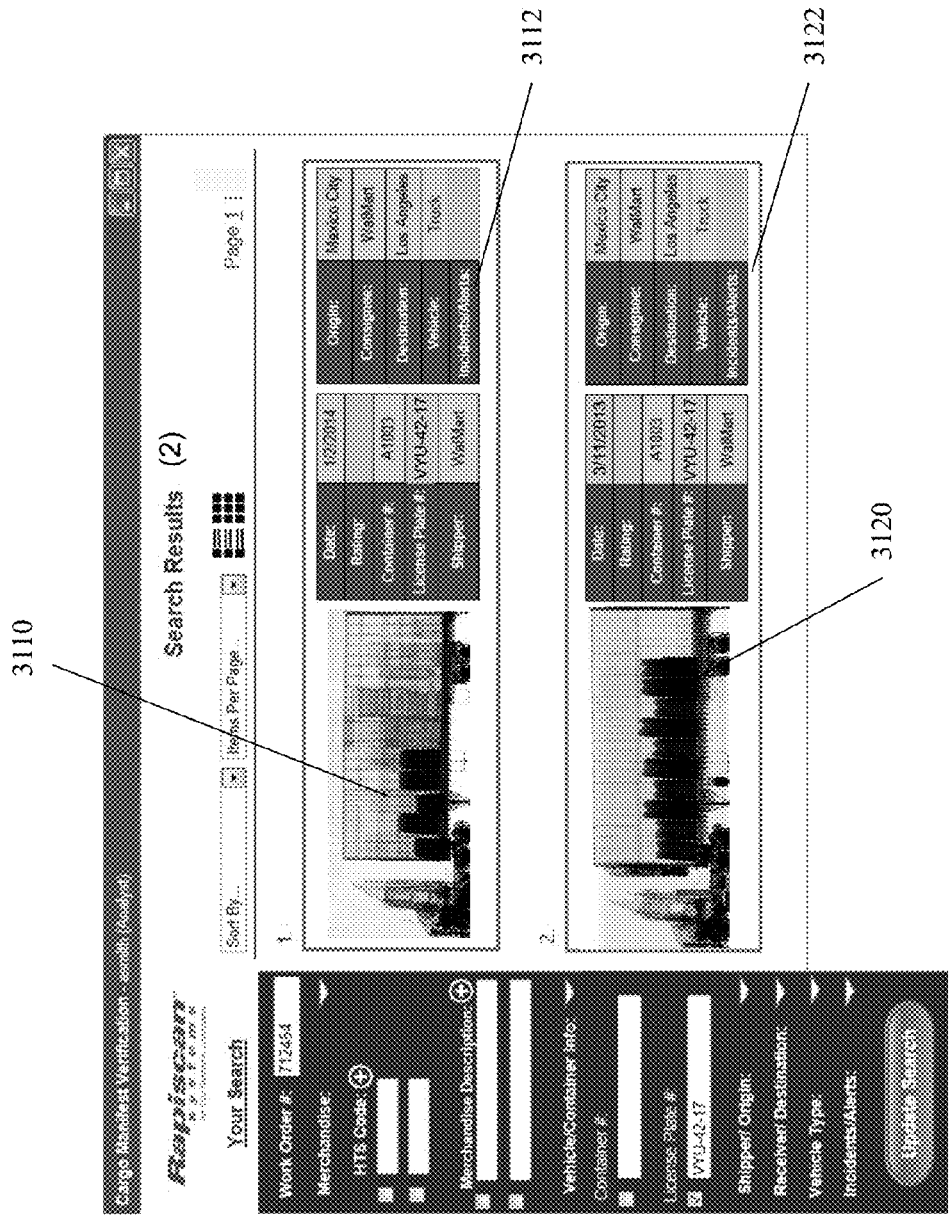
FIG. 31 illustrates an exemplary screen of an operator interface, according to one embodiment of the present specification.

FIG. 31 illustrates an exemplary screen of the operator interface of the present system for threat/contraband detection based on vehicle image comparison. Referring to FIG. 31, when a cargo vehicle, such as a truck, comes for inspection scan, two images 3110 and 3120 of the same truck, acquired on different dates, are found in the reference image database. Since the database is also linked to the vehicle/cargo manifest system, it provides information to the operator regarding origin and destination of the cargo, shipper and consignee, container identification number and the vehicle license plate number in tables 3112 and 3122 alongside the scan images.

Figure 32:
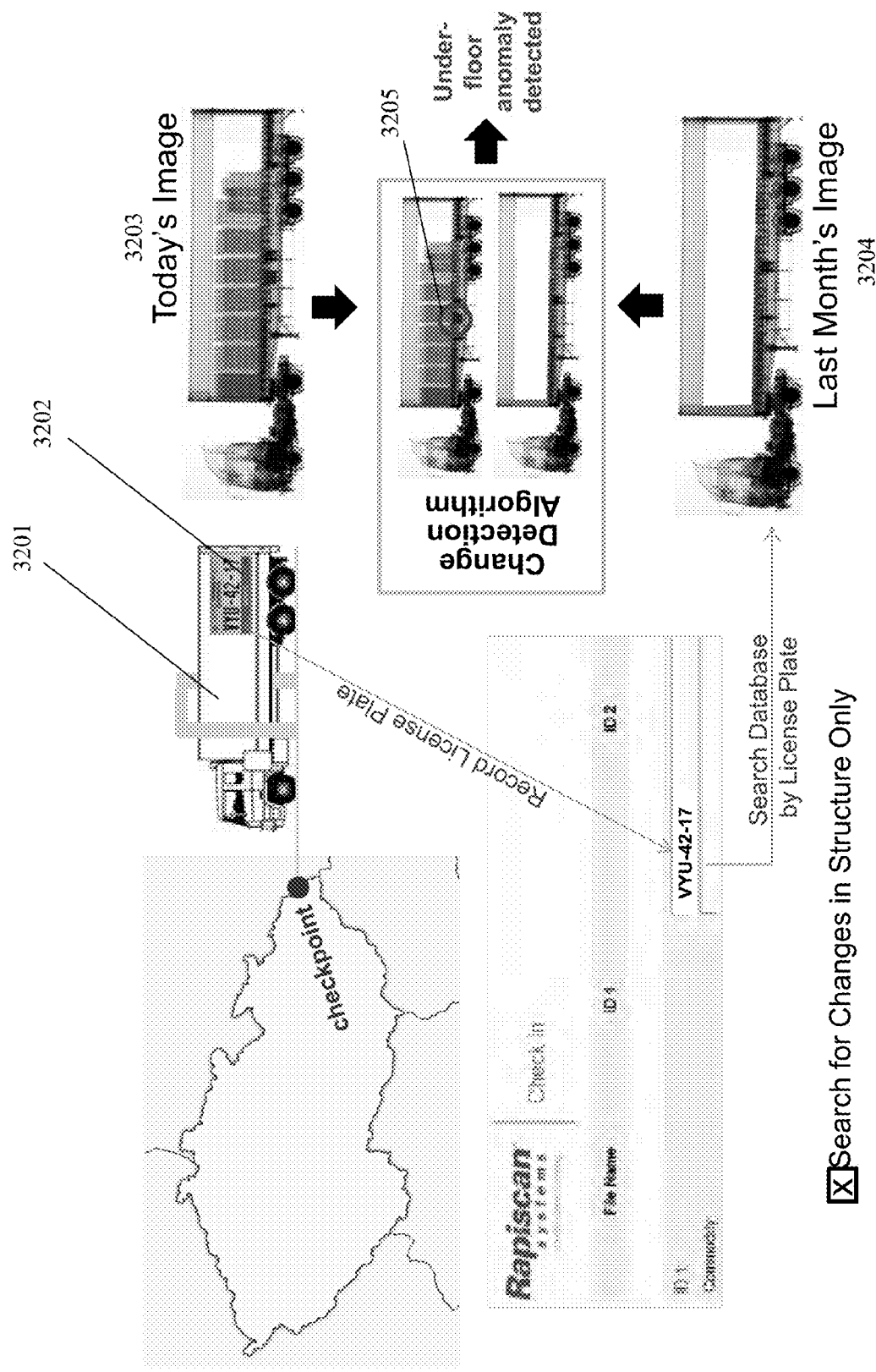
FIG. 32 illustrates how the current and historic vehicle images may be used for identifying changes in the vehicle structure over time.

FIG. 32 illustrates how the current and historic vehicle images may be used for identifying changes in the vehicle structure over time, in accordance with one embodiment. Referring to FIG. 32, when a vehicle 3201 is scanned, its license plate number 3202 is also recorded. The license plate number is used to retrieve the historical images and data for the same vehicle from the system database. Thereafter, the current image 3203 is compared against a historical image 3204. A change detection algorithm is applied to the two images, which identifies anomalies 3205. In the present example, the identified anomaly comprises an object hidden under the floor of the vehicle, which becomes apparent when the two images are compared using the change detection algorithm.

Figure 33:
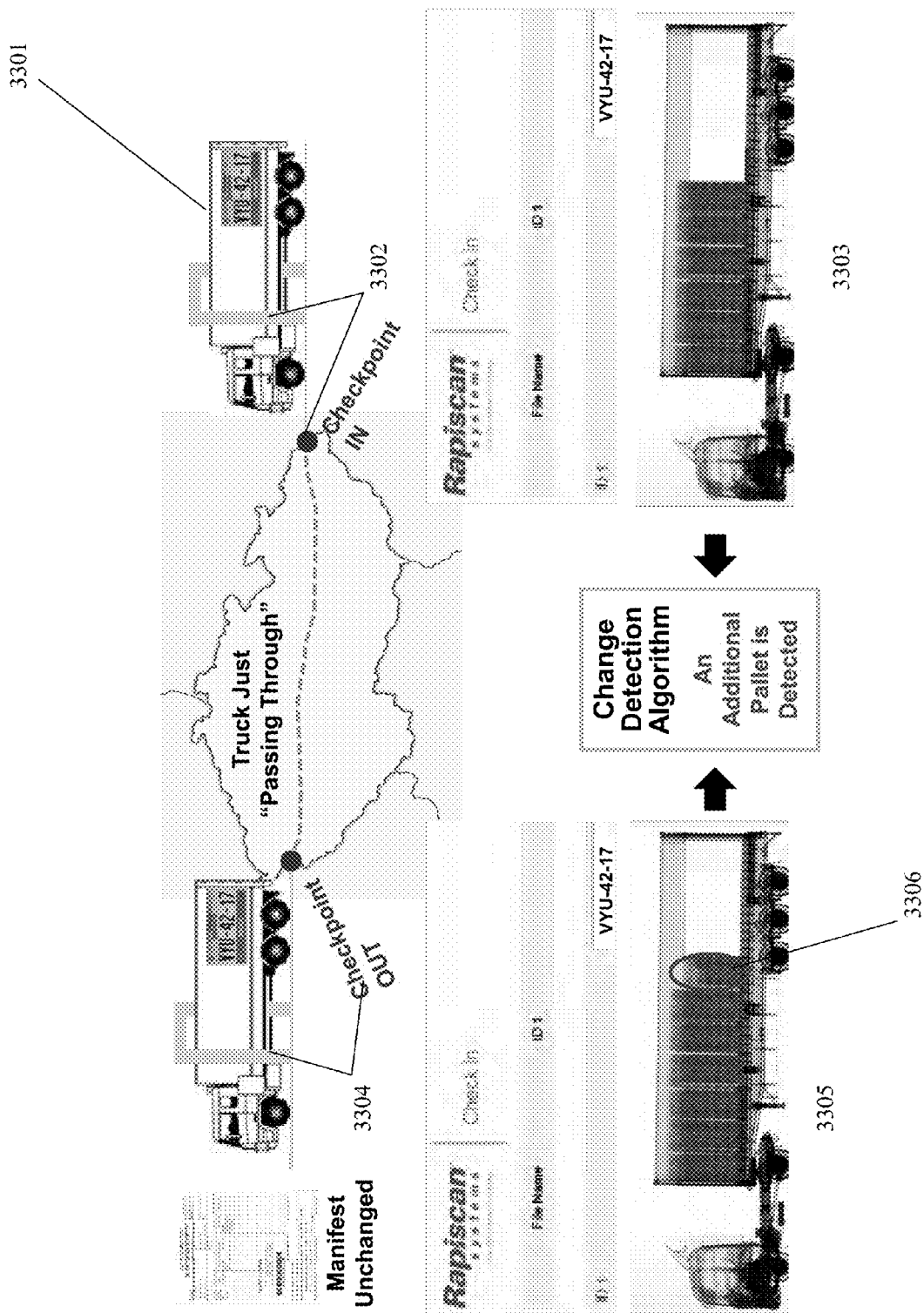
FIG. 33 illustrates the use of vehicle images for identifying changes in cargo contents over a traveled distance.

FIG. 33 illustrates how vehicle images may be used for identifying changes in the cargo contents over a travelled distance. Referring to FIG. 33, a cargo vehicle 3301 is scanned at a first checkpoint 3302 and its image 3303 is recorded. The cargo vehicle is again scanned at a second checkpoint 3304 and its image 3305 is recorded. The system then automatically compares the two images 3303 and 3305 and applies a change detection algorithm to them. As mentioned earlier, the two images are linked in the system database by means of common attributes of the vehicle, such as the license plate. After comparison, the change detection algorithm identifies the anomalies, if any. In the present example, an additional pallet 3306 is detected in the cargo, which is added in the distance between the first and second checkpoints. In this case, if the cargo manifest remains unchanged, as reported by the manifest information database, the operator may flag down the vehicle for further inspection.

Figure 34:
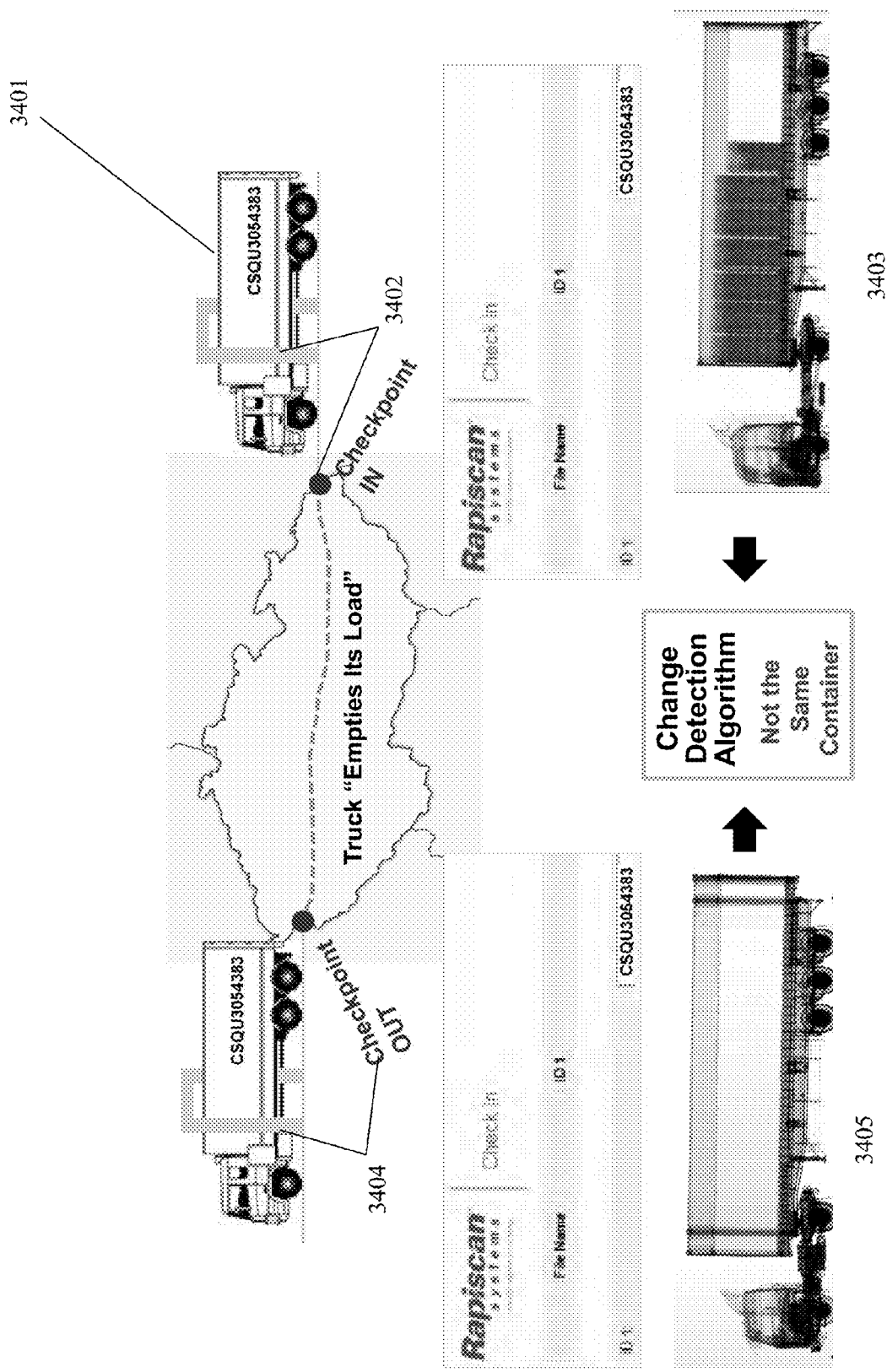
FIG. 34 illustrates another example of the use of vehicle images for identifying changes in cargo contents over a traveled distance.

FIG. 34 illustrates another example of how vehicle images may be used for identifying changes in the cargo contents over a travelled distance. Referring to FIG. 34, a cargo vehicle 3401 is scanned at a first checkpoint 3402 and its image 3403 is recorded. The cargo vehicle is again scanned at a second checkpoint 3404 and its image 3405 is recorded. The system then automatically compares the two images 3403 and 3405 and applies a change detection algorithm to them. As mentioned earlier, the two images are linked in the system database by means of common attributes of the vehicle, such as the license plate. After comparison, the change detection algorithm identifies the anomalies, if any. In the present example, it is detected that the vehicle has emptied its load in the distance between the first and second checkpoints, and in fact the container in the second image 3405 is not the same as the container in the first image 3403.

In another embodiment, the present specification discloses a method for characterizing cargo by providing estimates of cargo configuration, such as cargo weight as a function of position (length), pallet size and density.

In one embodiment, the method to obtain the weight of cargo comprises of combining the measured attenuation profile of the scanned cargo with the known geometry of the scanner. In one embodiment, for computing the pallets size and density, a priori assumptions about how the cargo is arranged in the container are used. Specifically, it is assumed that the cargo is arranged in one or two palletized rectangular blocks of uniform-density material that rest on the floor of the cargo container. This simplified model can be used to fit the measured attenuation profile to provide estimates of the dimensions including length, height and width of the cargo blocks, their front-to-back location in the container, and their effective steel density. For dual-energy scans, the atomic number information is used to improve the cargo characterization.

Figure 35:
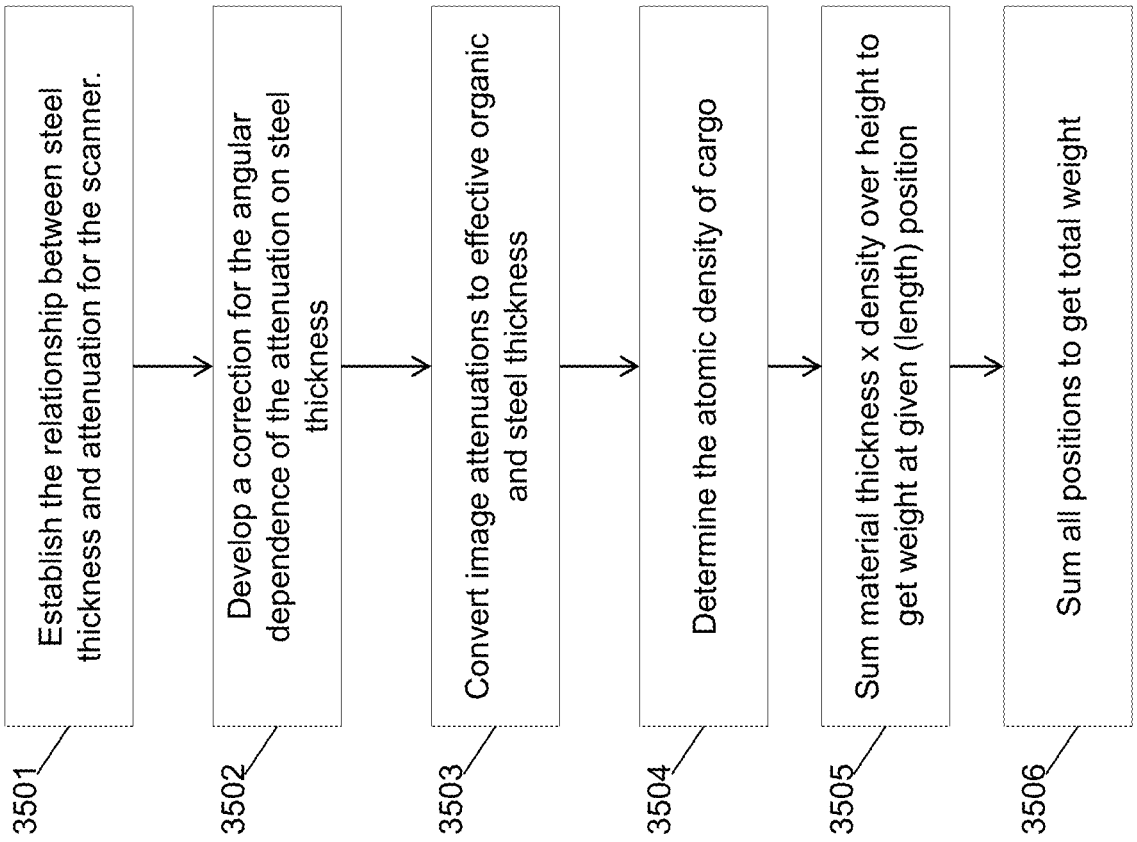
FIG. 35 is a flowchart illustrating an exemplary method of characterizing cargo by estimating cargo weight, according to one embodiment.

FIG. 35 is a flowchart illustrating an exemplary method of characterizing cargo by estimating cargo weight, according to one embodiment. Referring to FIG. 35, in the first step 3501, the relationship between steel thickness of the cargo blocks and attenuation for the scanner is established. Next, in 3502 a correction is developed for the angular dependence of the attenuation on steel thickness, using a model for the Linac spectrum and the known filtration on the radiation source. Thereafter in step 3503, image attenuations are converted to effective organic and steel thickness.

Next, in 3504 the atomic density of cargo is determined, if available. The sum of material thickness x density over height is then computed in step 3505, to get weight at given (length) position. Finally, all positions are summed to get total weight, in step 3506.

Figure 36:
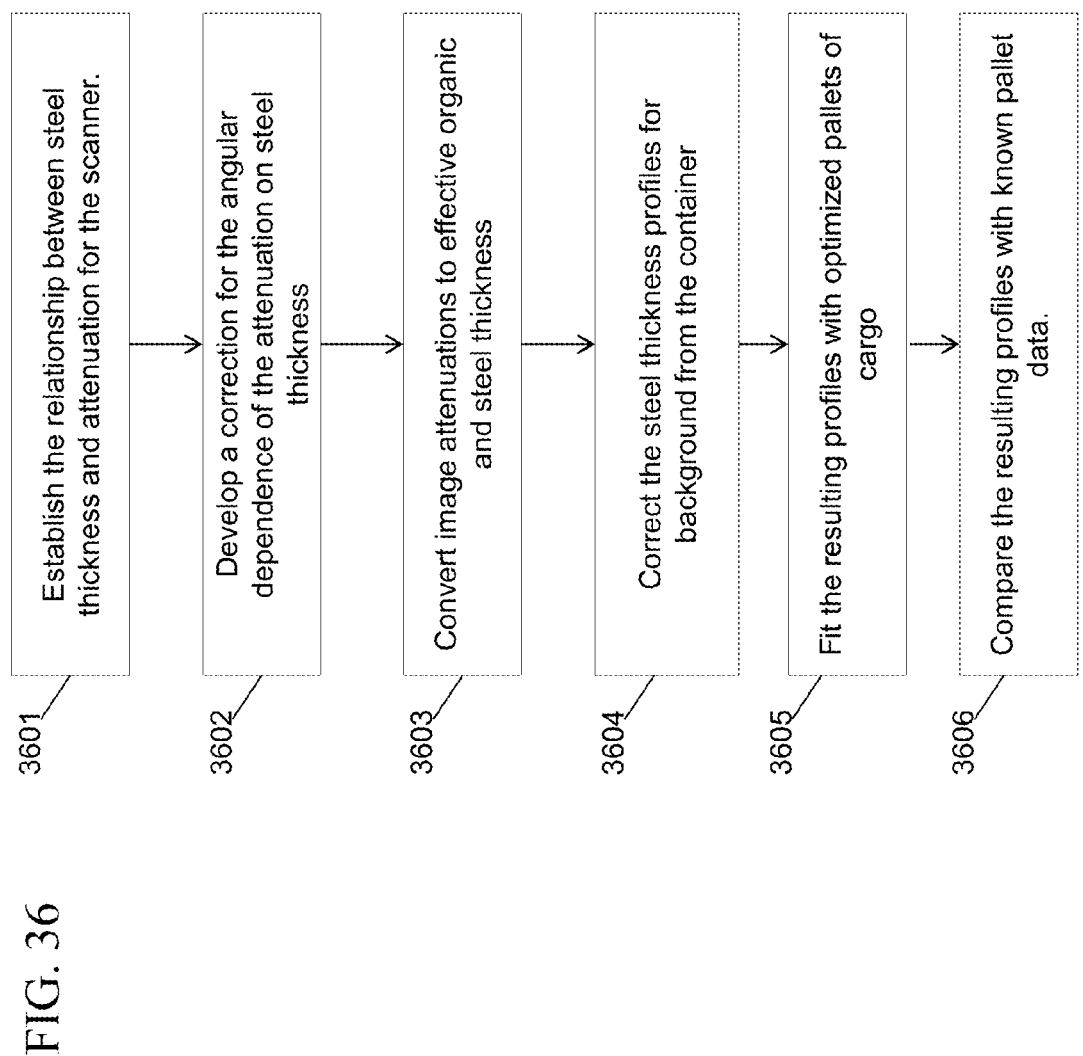
FIG. 36 is a flowchart illustrating an exemplary method of characterizing cargo by estimating pallets size and density, according to one embodiment.

FIG. 36 is a flowchart illustrating an exemplary method of characterizing cargo by estimating pallets size and density, according to one embodiment. Referring to FIG. 36, in the first step 3601, the relationship between steel thickness of the pallet blocks and attenuation for the scanner is established. Next, in 3602 a correction is developed for the angular dependence of the attenuation on steel thickness, using a model for the Linac spectrum and the known filtration on the radiation source. Thereafter in step 3603, image attenuations are converted to effective organic and steel thickness.

Next, in 3604 the steel thickness profiles are corrected for background from the container. The resulting profiles are then fit with optimized pallets of cargo, varying the height, depth, and effective steel density of the cargos, as shown in step 3605. The resulting profiles are then compared with the known pallet data in step 3606. Optionally, the analysis may be extended to more irregular cargos so that it can be determined whether the assumptions are reasonable.

The above steps of flowcharts of FIGS. 35 and 36 are explained in further detail below.

Effective Steel Thickness and Attenuation

Figure 37:
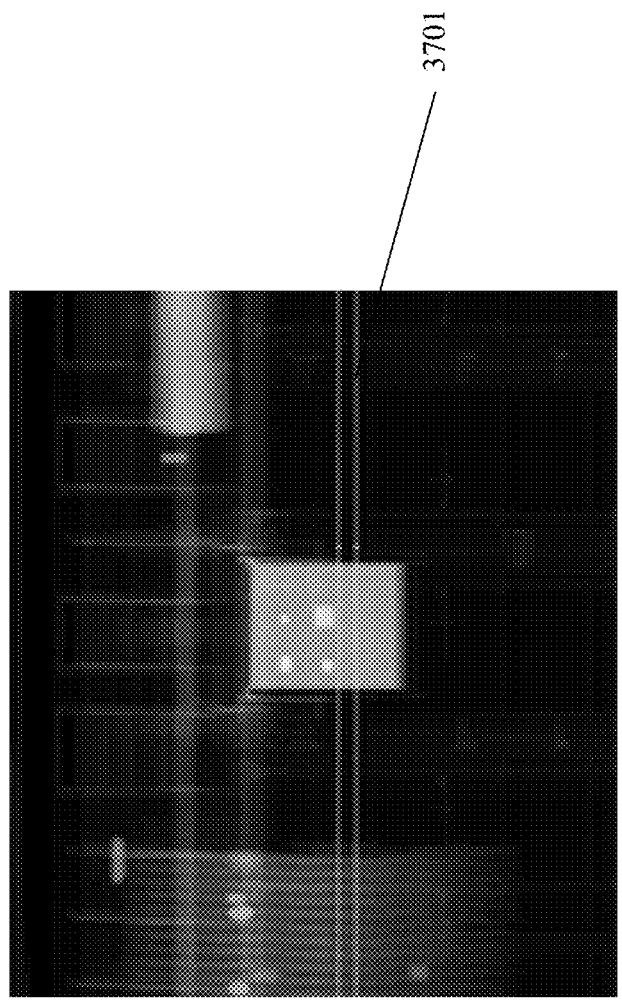
FIG. 37 illustrates a scan image of a cargo container, according to one embodiment.
Figure 38B:
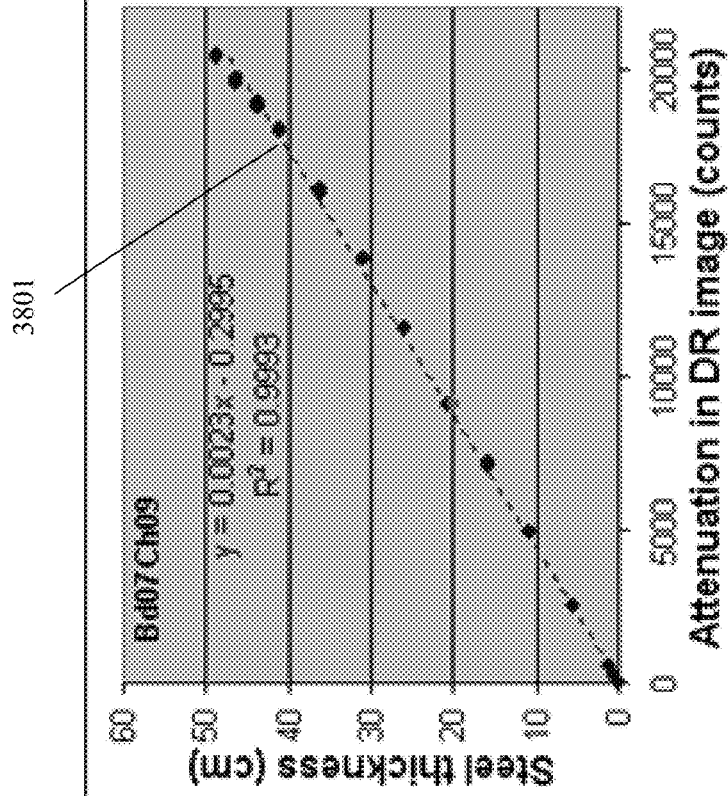
FIG. 38B is a graph illustrating the accuracy in predicting steel thickness as a function of attenuation counts.
Figure 38A:
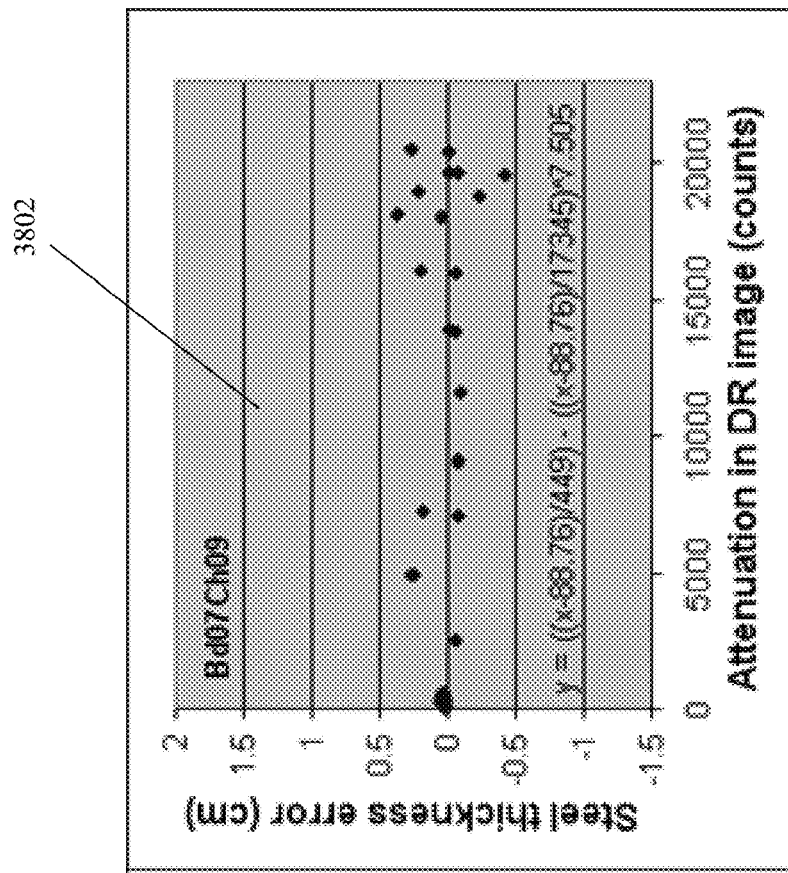
FIG. 38A is a graph illustrating a linear fit to steel thickness as a function of attenuation counts.

FIGS. 37, 38A and 38B illustrate how data collected using a radiation source, which is a 9MV Linac in this example, is used to determine the relation between measured attenuation and steel thickness along the beam centerline, in accordance with one embodiment of the present specification. Referring to FIG. 37, a scan image of a cargo container with the test fixture holding 14" (35.56 cm) of steel plate near the centerline of the Linac beam is shown. The attenuation profile is measured along the region-of-interest (ROI) 3701, yielding an average attenuation of about 16000 counts for the steel plate. The measurement is repeated for a number of scans as a function of the known steel thickness, which also contains a contribution from the container walls of 0.49 cm. The attenuations of the steel plates plus the container walls are then fit with a straight line, which is shown in FIG. 38A. Referring to FIG. 38A, graph 3801 illustrates a linear fit to steel thickness as a function of attenuation counts.

A 4-parameter fit to obtain the steel thickness from attenuation at this location in the detector array can be computed as:

$$y(\text{cm steel}) = (x - x_0)/mu - ((x - x_0)/c)^m \quad (1)$$

where:

$x_0 = 88.76$ counts, attenuation offset observed for air $mu = 449$ counts/cm, linear attenuation coefficient for steel $c = 17345$ counts, attenuation where the value of mu drops $m = 7.505$, exponent that indicates how fast mu changes.

The above computation is depicted by the graph 3802 of FIG. 38B, which shows that the fit predicts the steel thickness to an accuracy of better than 0.5 cm.

Correction for Angular Dependence

Figure 39B:
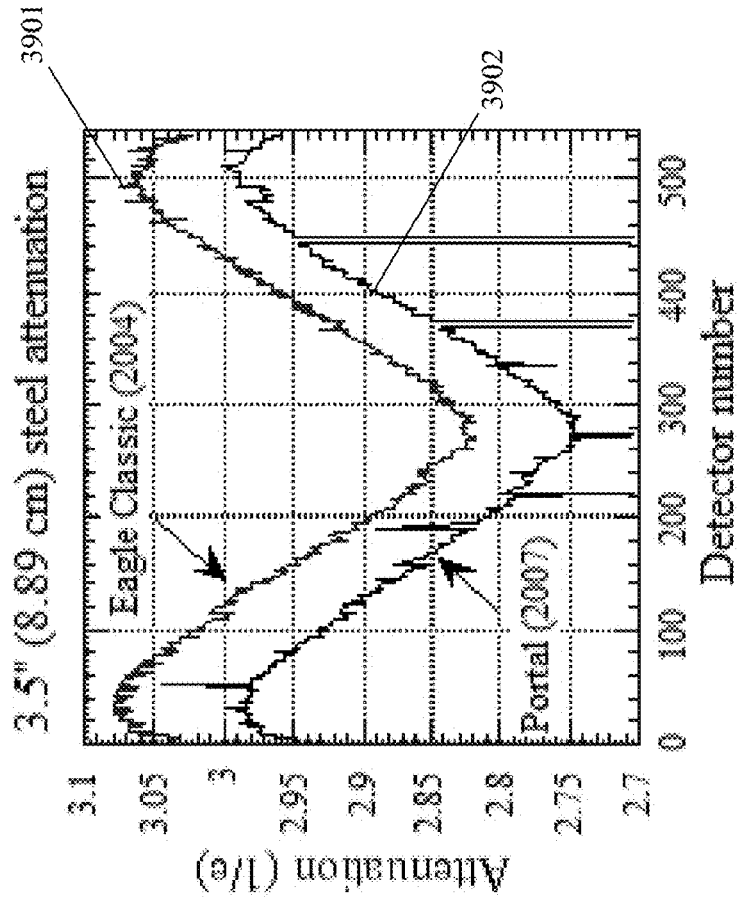
FIG. 39B illustrates an exemplary plot of the attenuations for 7" thick steel at different positions along the detector array.
Figure 39A:
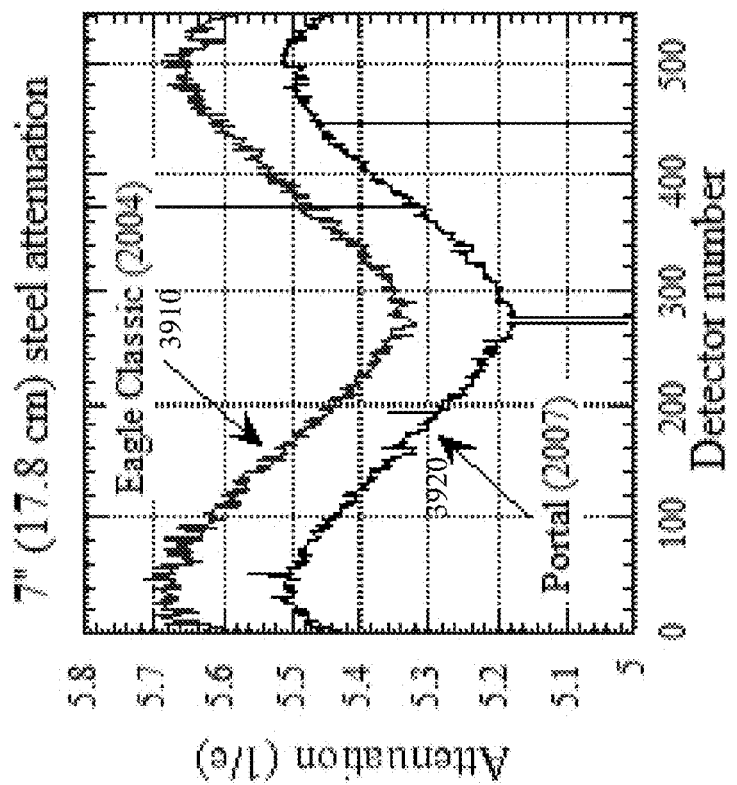
FIG. 39A illustrates an exemplary plot of the attenuations for 3.5" thick steel at different positions along the detector array.

Error! Reference source not found.illustrate exemplary plots of the attenuations for 3.5" and 7" thick steel respectively, at different positions along the detector array. Referring to FIG. 39A, plots 3901 and 3902 represent attenuations for 3.5" thick steel for two different 6MV cargo scanner systems. Similarly in FIG. 39B, plots 3910 and 3920 represent attenuations for 7" thick steel for two different 6MV cargo scanner systems. This example illustrates the angular dependence of steel attenuation that results from a decrease in the energy of the x-ray spectrum with increasing angle.

In another example, the attenuation for a 9MV-linac was measured and found to be around 3% lower than the 6MV-linac attenuation. This may be associated with differences in Linac target thickness and filtration, while the down-turn in attenuation at the ends of the array is likely associated with scatter from material beyond the ends of the detector array where the flux is not attenuated by steel.

Using the results from the simulations, Equation (1) can be modified to include the angular dependence for three of the filters:

$$y(\text{cm steel}) = (x-x_0)/mu(\theta) - ((x-x_0)/c(\theta)^{m(\theta)}) \qquad (2)$$

where the source-detector angle, $\theta$(deg), is measured relative to the central detector, 270, and the detectors are numbered from 0 to 543 starting from the top of the array.

Fit to Uniform Cargoes

Figure 40:
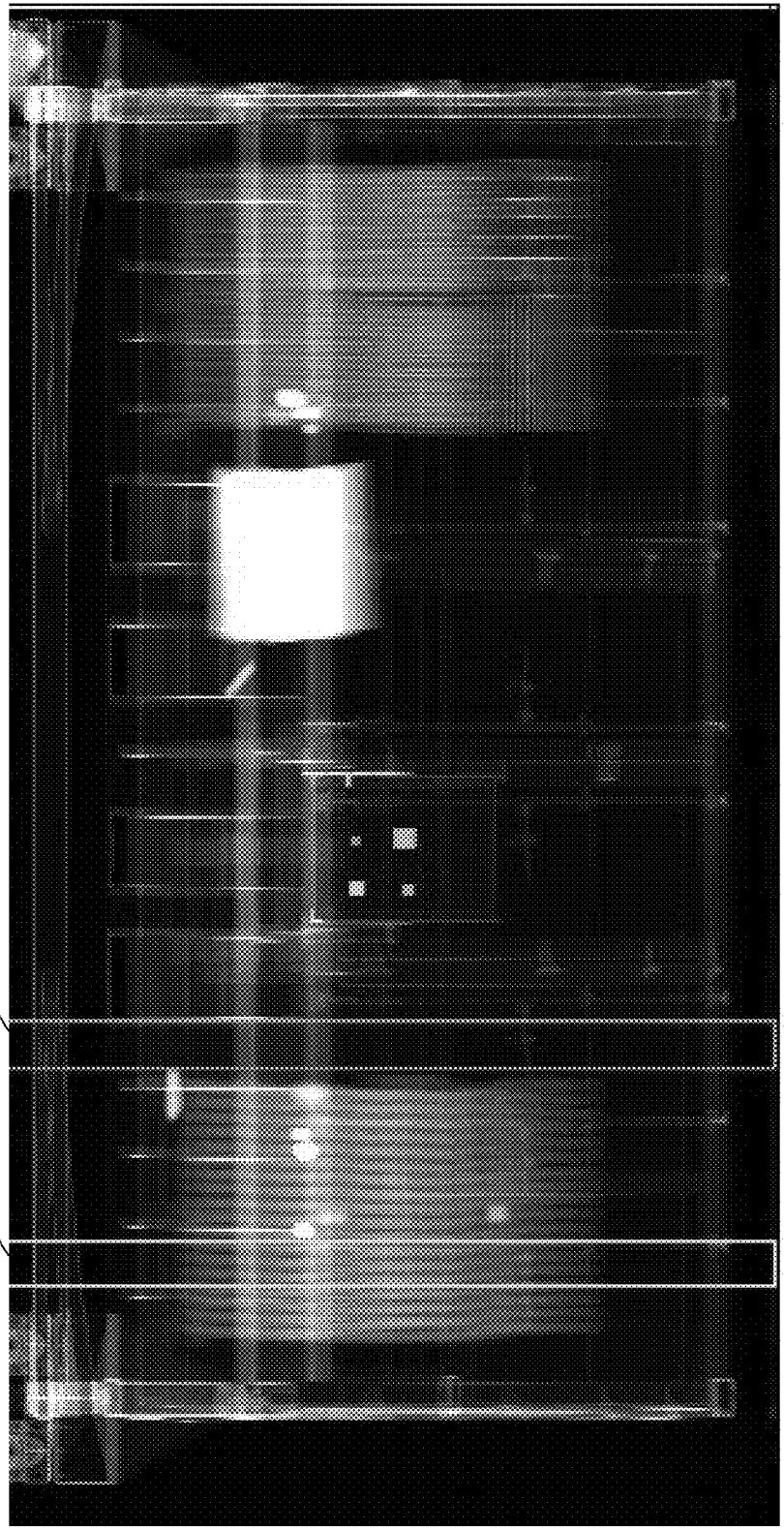
FIG. 40 shows a scan image for an exemplary uniform cargo.
Figure 41:
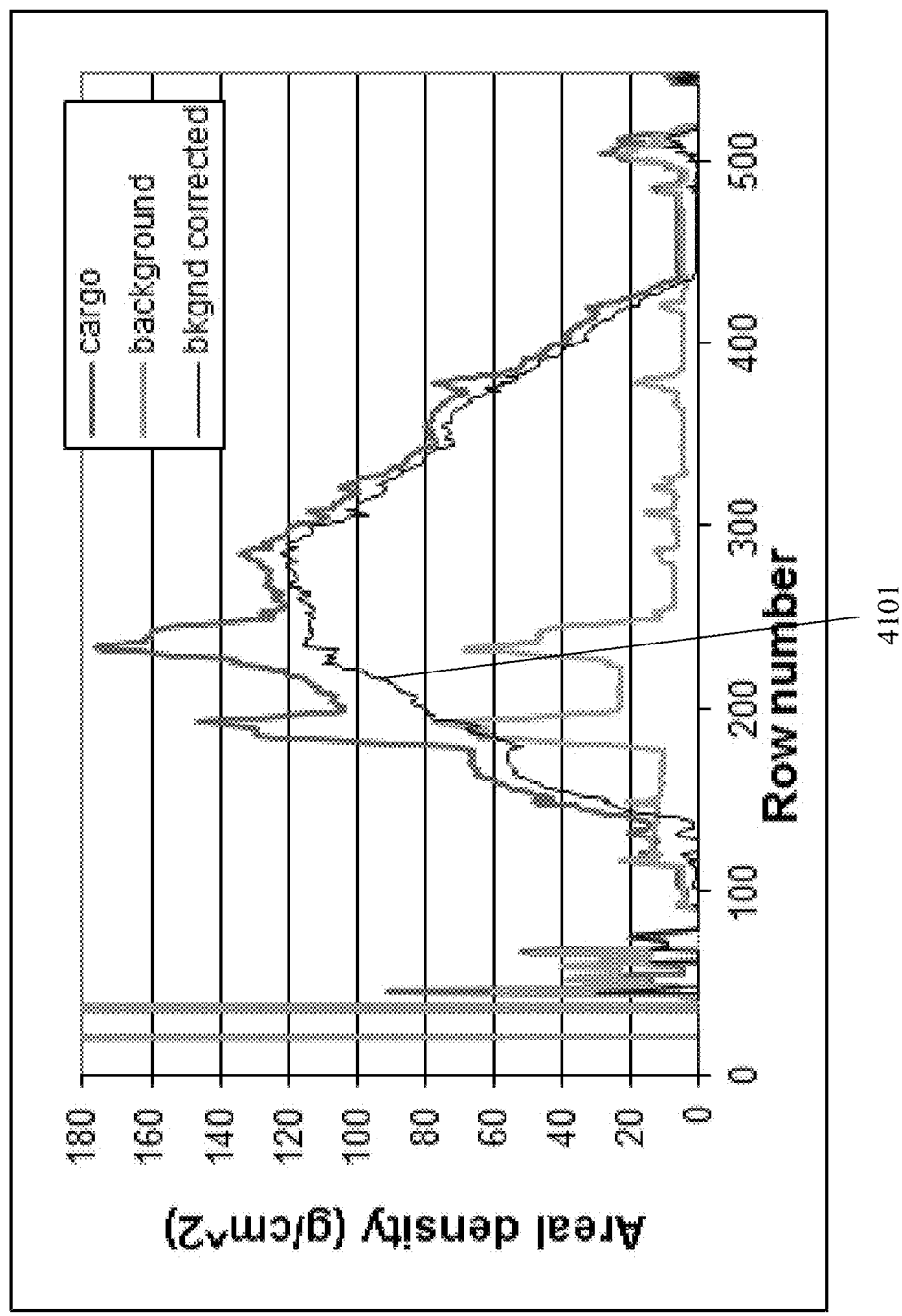
FIG. 41 illustrates a cargo attenuation (areal density) graph with background correction, in accordance with one embodiment.

Error! Reference source not found. shows a scan image for an exemplary uniform cargo comprising water bottles, used to develop the fitting procedure with respect to equations (1) and (2). Referring to FIG. 40, cargo is indicated by the rectangle 4001, while rectangle 4002 indicates a background region of interest (ROI). In one embodiment, equation (2) is multiplied by the nominal density of steel, 7.8 g/cm³, to yield the formula for converting image attenuation counts to areal density (g/cm²). Applying the background correction yields the cargo attenuation (areal density) shown as 4101 in Error! Reference source not found. Application of least-square fit to the background-corrected steel areal density then yields the fits shown in Error! Reference source not found. for one pallet of cargo 4201, and for two pallets of cargo 4202. The results of fits to attenuation profile of water bottles are summarized in a table in FIG. 43. Referring to FIG. 43, it can be seen that the cargo dimensions and characteristics obtained for single pallet 4301 and double pallet 4302 using the present method, are close to the measured dimensions and characteristics 4303.

Figure 44:
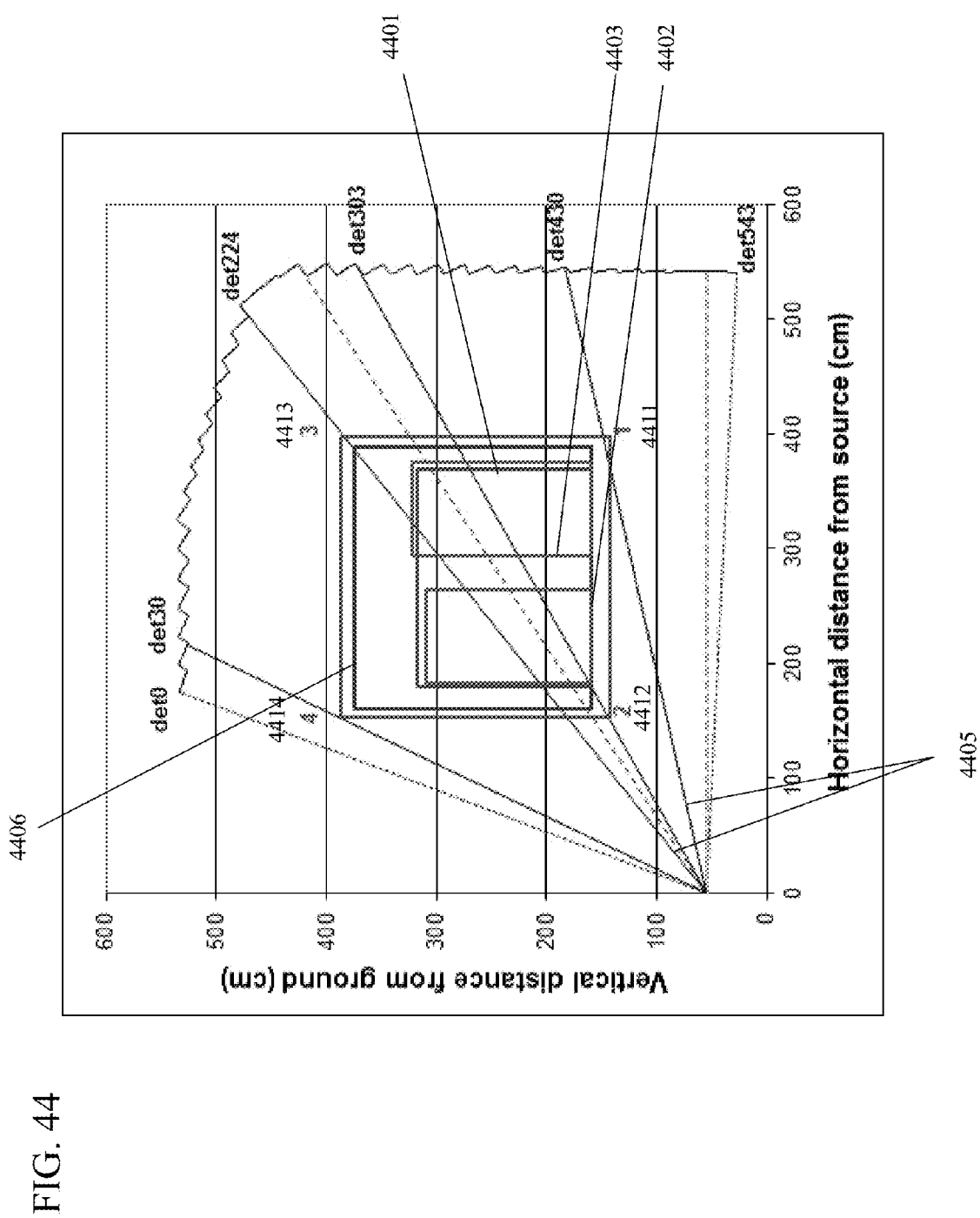
FIG. 44 illustrates how location and geometry of pallets can be inferred from the attenuation profiles obtained from various detectors in a detector array.

In one embodiment, the present method also takes into account the air gap between pallets while computing the attenuation values to determine cargo characteristics. FIG. 44 illustrates how location and geometry of pallets can be inferred from the attenuation profiles obtained from various detectors in the detector array. Referring to FIG. 44, the rectangle 4401 represents the single pallet fit, while the rectangles 4402 and 4403 represent the double pallet fit. The outside corners of the cargo container are represented by 4411, 4412, 4413 and 4414. Projected lines 4405 from source through the corners indicate the detector number where the corners appear in the image. Rectangle 4406 indicates the position, where the inside walls of the cargo container are estimated to be located.

Figure 42:
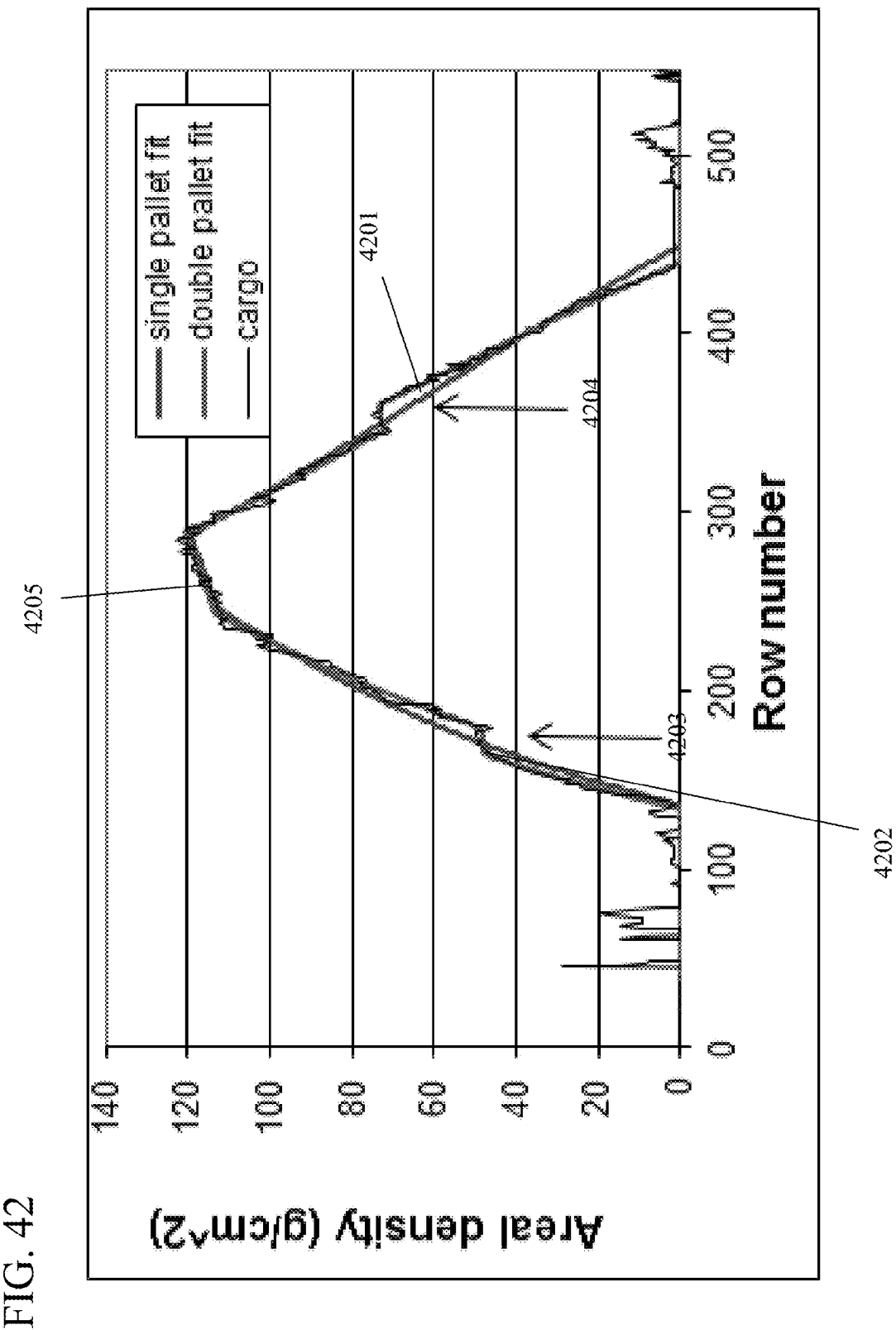
FIG. 42 is a graph illustrating fits to the attenuation profile using a single pallet and two pallets of cargo, in accordance with one embodiment.

Referring together to FIGS. 42 and 44, the primary features in the areal density plot of FIG. 42 can be understood as follows. Starting from the bottom of the detector package in FIG. 44, the corner of the pallet on the right 4403 is first encountered, which leads to an increasing areal density. At the gap between pallets, the curve levels off, indicated by arrow 4203 in FIG. 42. This is because in that region, the x-rays only penetrate the left and right sides of the second cargo pallet 4403 with a near constant path length. The rays then encounter the lower right hand corner of the left pallet 4402 and the attenuation increases up to the top plateau 4205. This plateau is where rays pass through the sides of both cargo pallets, so there is only a small change in attenuation with height on the detector array. The subsequent decrease in attenuation then follows a similar set of transitions as the x-rays cross the gap between cargos, indicated by second arrow 4204 in FIG. 42.

In one embodiment, several types of uniform cargos were tested and it was found that cargos that are periodic in attenuation along the scan direction yield reasonably stable fit densities with the present method, as long as the region of interest is several periods wide. Since any changes in background attenuation due to cargo container features will limit the accuracy of the derived densities, in one embodiment, the present method further includes a useful tool for operator-assisted analysis. The tool enables an operator to select adjustable ROIs to exclude areas from the main ROI that show obvious changes in background.

Scans of Non-Uniform Cargo

Figure 45:
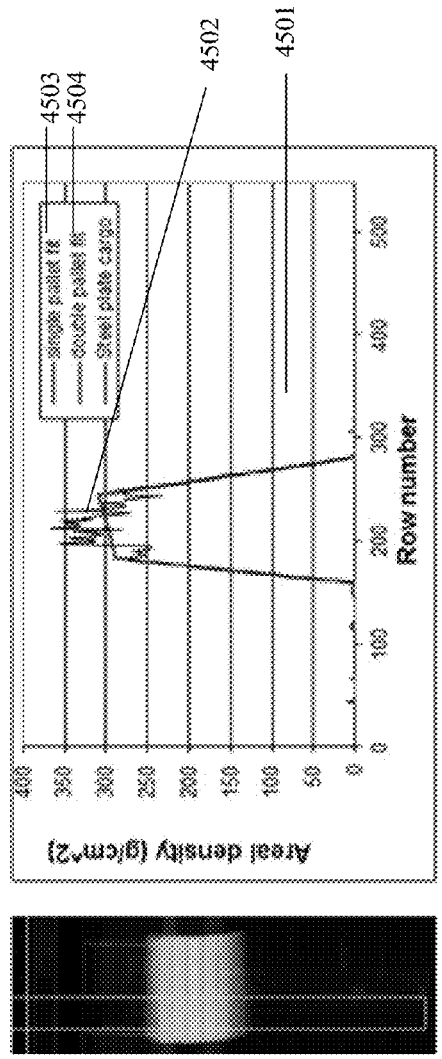
FIG. 45 illustrates another exemplary container scan image using the present method, according to one embodiment.

FIG. 45 illustrates another exemplary container scan using the present method. Referring to FIG. 45, a non-uniform cargo comprising a container of the steel plates is scanned. The resulting attenuation graph 4501 representing steel penetration shows a small but high-attenuation region 4502. In this case, the curves 4503 for single and 4504 for double pallet scans yield nearly identical results, because the gap in the double pallet fit goes to zero.

Figure 46:
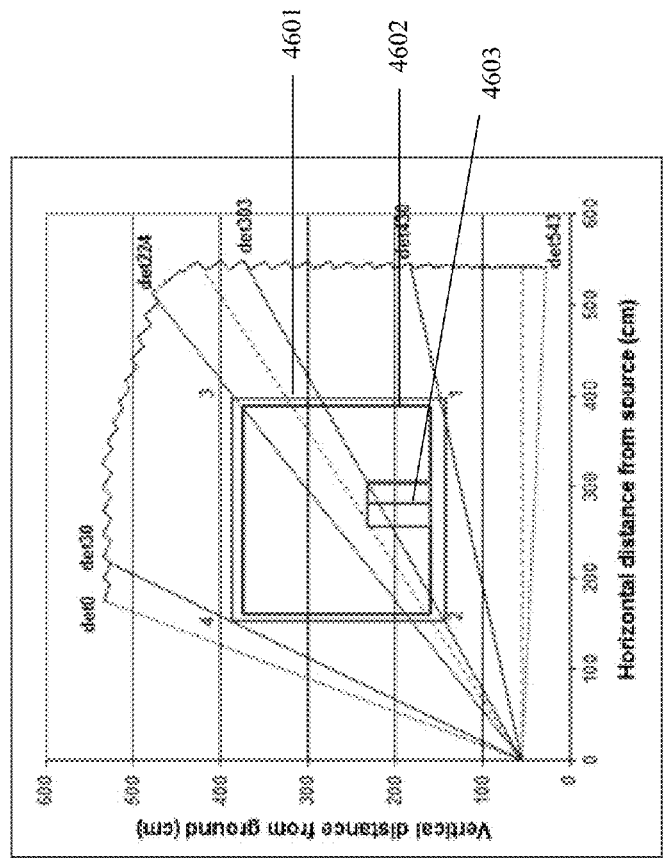
FIG. 46 illustrates the inferred location and orientation of steel plates in a cargo container, corresponding to the attenuation profile of FIG. 45, in accordance with one embodiment.

FIG. 46 illustrates the inferred location and orientation of steel plates in the cargo container, corresponding to the attenuation profile of FIG. 45. Referring to FIG. 46, the outer and inner sides of the container are represented by 4601 and 4602, respectively. The location and orientation of steel plates in the cargo container is represented 4603.

It may be noted that cargos that are grossly non-uniform and are not rectangular in shape may not yield accurate cargo distributions. For example, if the steel plates in a cargo are stacked in a tilted or haphazard manner, it violates the basic assumption of the fit model that assumes square corners (90 deg) for the steel cargo with the plates standing upright. In such cases, additional scan views may be required to constrain the model further to provide a more accurate fit.

In one embodiment, the extracted cargo parameters are used for different weight calculations, including determination of pallet-by-pallet weight and full cargo weight.

In one embodiment, cargo weight (W) is estimated using the following equation, which is applied pallet-by-pallet:

$$W = \sum \frac{\ln(I/I_0)}{-\mu_M} * pixelWidth * pixelHeight,$$

where the sum is taken over all pixels in the volume of interest, $\mu_M$ is the mass attenuation coefficient, and $I/I_0$ represents the normalized pixel intensity value;

pixelWidth=containerLength in cm/containerlength in pixels; and pixelHeight is obtained from the geometric information of the scanner.

To estimate the palletized-cargo weight, $\mu_M$, pixelWidth and pixelHeight must be determined.

To determine $\mu_M$: Based on high-energy data (HE) and low-energy data (LE), the material type is estimated by using $\mu_{ratio}$. From the material type, the corresponding $\mu_M$ is obtained using a look up table.

Figure 47:
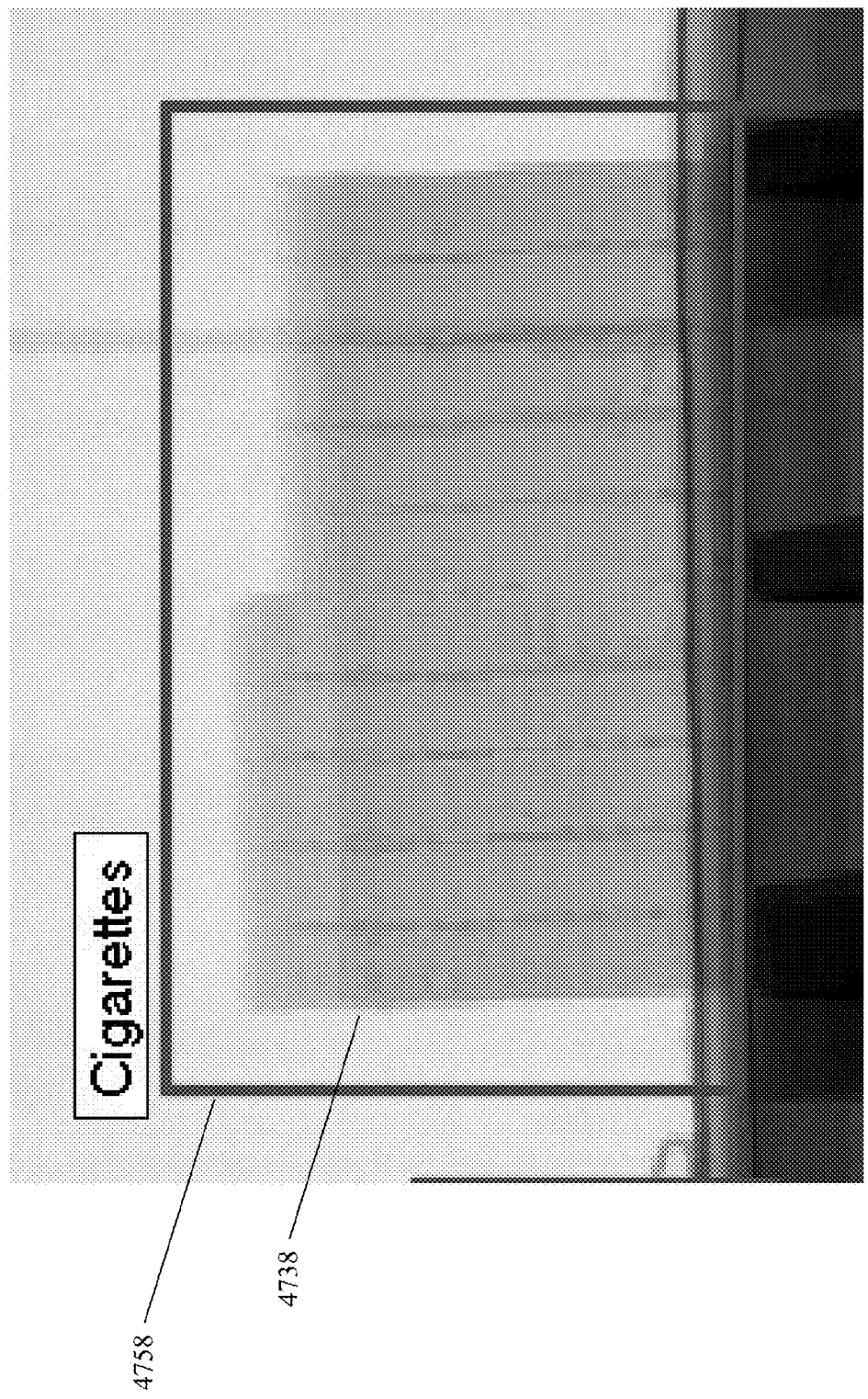
FIG. 47 illustrates an exemplary dual-energy scan image of cigarettes in a cargo container.

In one embodiment, the systems and methods of the present specification may be used for detection of specific contraband, such as cigarettes. FIG. 47 illustrates an exemplary dual-energy scan image of cigarettes 4738 in a cargo container 4758. The system of present specification takes into account the specific features and characteristics of cigarettes such us density, texture, spacing of the gaps, etc. to automatically detect the presence of cigarettes.

In one embodiment, the present method relies on various operator assist tools described earlier for detection of cigarettes, such as empty container verification, anomaly detection, pattern recognition, material discrimination, matching the cargo with manifest (verification) and pallet characteristics.

In one embodiment, the present system uses empty container verification tool to detect difficult cases of drugs concealed in containers, such as in door frames, door panels, container frame, corner blocks, in the floor or other cases where the image of container structure may mask contraband.

One of ordinary skill in the art would appreciate that dual-energy x-ray technology, even at high energy, cannot distinguish different types of organic materials. Therefore, anomalies in the x-ray images may require time-consuming, labor-intensive opening of containers potentially resulting in high false-alarm rate or in low detection due to the increased clearing to avoid opening containers.

Drugs are commonly found to be concealed in homogeneous organic cargo, such as that comprising fruits and vegetables or grains. Contraband can also be concealed in industrial equipment, and sometimes equipment must be damaged to determine whether there is contraband. If contraband is not found, the shipper must be compensated for the damage. There are other cases where intelligence indicates a high probability that contraband is hidden in a container or truck. In these and other cases, it would be useful to resolve the alarm without opening the container. Therefore in one embodiment, the system of present specification employs methods for determining the elemental composition of cargo for detection of contraband such as drugs and narcotics.

One of the methods to determine the elemental composition of cargo is employing neutrons. In this case, a pulsed neutron generator inspects an area of cargo suspected of containing contraband. A neighboring region could also be inspected for comparison. The results are an elemental map as a function of depth. The elemental composition is then employed to determine the probability that the cargo contains a specific type of contraband. The elemental composition of selected materials is shown in the table illustrated in FIG. 48. The last two columns 4801 and 4802 show some of features employed to identify the different materials. For example, a high a carbon-to-oxygen ratio (C/O) indicate the presence of cocaine, heroin and other drugs. Thus for example, a cargo of fruits and vegetables would result in a C/O of approximately 0.1. However, in the area where cocaine is present, the ratio would be about 3. If the ratio does not change significantly as a function of area, there is no need to open the container or destroy cargo, thereby saving considerable time and cost.

In one embodiment, the present system employs an additional concept of operation, by inspecting areas of the cargo for cargo-manifest verification. The elemental composition of the scanned areas is compared to the elemental composition of the claimed manifest to provide a probability that the manifest is correct. In one embodiment, the system further employs tools for detection of pallet anomalies for drug detection. Such tools determine, for example, if a pallet should be homogenous or not, based on the manifest and material data from the database. An alarm is raised in case an anomaly is found.

In various embodiments, a combination of operator assist tools are used and help identify cases where contraband is concealed in parts of the truck other than the container or trailer—for example, when drugs are concealed in the spare tire of a truck.

Figure 19:
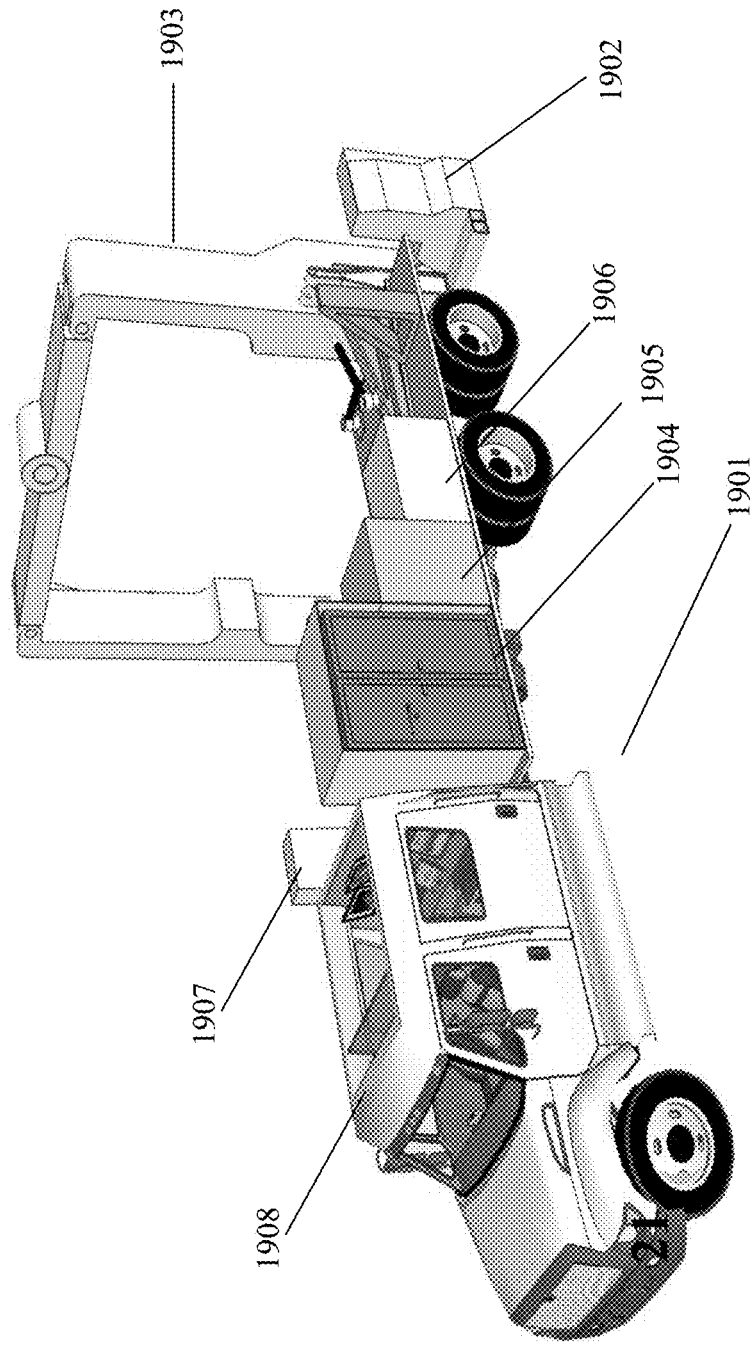
FIG. 19 illustrates an exemplary mobile inspection system, to which the methods of the present specification may be applied.

FIG. 19 is an illustration of an exemplary X-ray scanning system to which any of the methods of the present specification may be applied. It should be noted herein that one exemplary scanning and inspection system that may be employed with the systems and methods of the present specification includes, but is not limited to the Rapiscan Eagle Mobile inspection system. Other systems that are appropriate include inspection systems using a gantry, inspection systems having a portal configuration, and scanning systems designed specifically for rail cars. It may be noted that any suitable system for inspecting cargo, cargo containers, and their contents may be employed for the purpose of application of the methods of present specification. As such, U.S. patent application Ser. Nos. 12/780,910; 13/370,941; 13/548,873; 13/532,862; 13/168,440; 13/175,792; 13/433,270; 13/281,622; 13/108,039; 12/675,471; 12/993,831; 12/993,832; 12/993,834; 12/997,251; 12/919,482; 12/919,483; 12/919,484; 12/919,485; 12/919,486; 12/784,630; 12/784,465; 12/834,890; 13/009,765; 13/032,593; 13/368,178; and Ser. No. 13/368,202, all assigned to the assignee of the present invention represent various systems that may be employed with the present invention and are herein incorporated by reference in their entirety. In addition, U.S. Pat. Nos. 5,638,420; 6,542,580; 7,876,879; 7,949,101; 6,843,599; 7,483,510; 7,769,133; 7,991,113; 6,928,141; 7,517,149; 7,817,776; 7,322,745; 7,720,195; 7,995,705; 7,369,643; 7,519,148; 7,876,879; 7,876,880; 7,860,213; 7,526,064; 7,783,004; 7,963,695; 7,991,113; 8,059,781; 8,135,110, 8,170,177; 8,223,919; and 8,243,876 all assigned to the assignee of the present invention represent various screening systems that may be employed with the present invention are herein incorporated by reference in their entirety.

Referring to FIG. 19, in one embodiment, inspection system 1900 comprises a mobile inspection system that can be deployed at any checkpoint for inspecting vehicles and cargo containers. FIG. 19 illustrates a side view of the mobile inspection system in a deployed configuration. The system comprises a vehicle 1901, such as a truck, with a flat-bed surface and equipment mounted on it. The equipment comprises an X-ray source 1902, a boom 1903, a modulator 1904, chiller 1905 and hydraulics assembly 1906. A radiation detector 1907 is also mounted on the bed of the truck 1901.

The front part of the vehicle 1901 comprises the operator cab 1908. In one embodiment, the operator cab 1908 has two operator stations, each equipped with large high-resolution displays for scanning operations.

In one embodiment, the X-ray source 1902 and the boom 1903 are part of a single fixture that can be deployed or stowed.

In one embodiment, the mobile inspection system 1900 uses a dual energy mode of scanning. In this technique, an X-ray source emits alternating pulses of low and high energies. The difference or ratio of the transmissions for the two energies yields information about the atomic number (Z) of the cargo material traversed. Thus, in one embodiment X-ray source 1902 switches between two operating voltages in an interlaced fashion. In another embodiment, system 1900 comprises a first X-ray source 1902 and a second X-ray source (not shown) that deliver images from two views, horizontal and vertical, respectively. This allows the system to produce two separate simultaneous images from approximately perpendicular orientations, thereby providing more comprehensive imagery, reducing the need for repositioning and rescanning and enabling rapid and accurate threat detection. In one embodiment, both sources are of same type and have the same operating voltage, which is in the range of 200 kV. In one embodiment, the inspection system uses from three to five X-ray sources, each operating at a single voltage.

In one embodiment, the system provides dual view scanning, with the two views being generated by two X-ray sources or by a single source alternating operation between high and low energies. In one embodiment, each view is supported by an L-shaped array of dual-energy detectors that separate the x-rays received into a first energy bin and a second energy bin, wherein, in an embodiment, the first energy bin is low energy and the second energy bin is high energy. In one embodiment, each array contains two rows of detectors, with one set collecting the low-energy x-rays and the other set collecting the high-energy x-rays. This dual-energy data is the foundation for generating the atomic number (Z) information, thereby providing material discrimination essential for effective detection algorithms.

In one embodiment, the operating voltage of the X-ray source employed may range from 1 kV to 1 MeV, and can be varied depending upon the system in which the present invention is implemented. Further, it may be appreciated that an x-ray source that switches among two or more operating voltages may be used as well. Further, while the present example describes a dual-view system, it may be appreciated that a single-view or multi-view system may be used as well.

Figure 20:
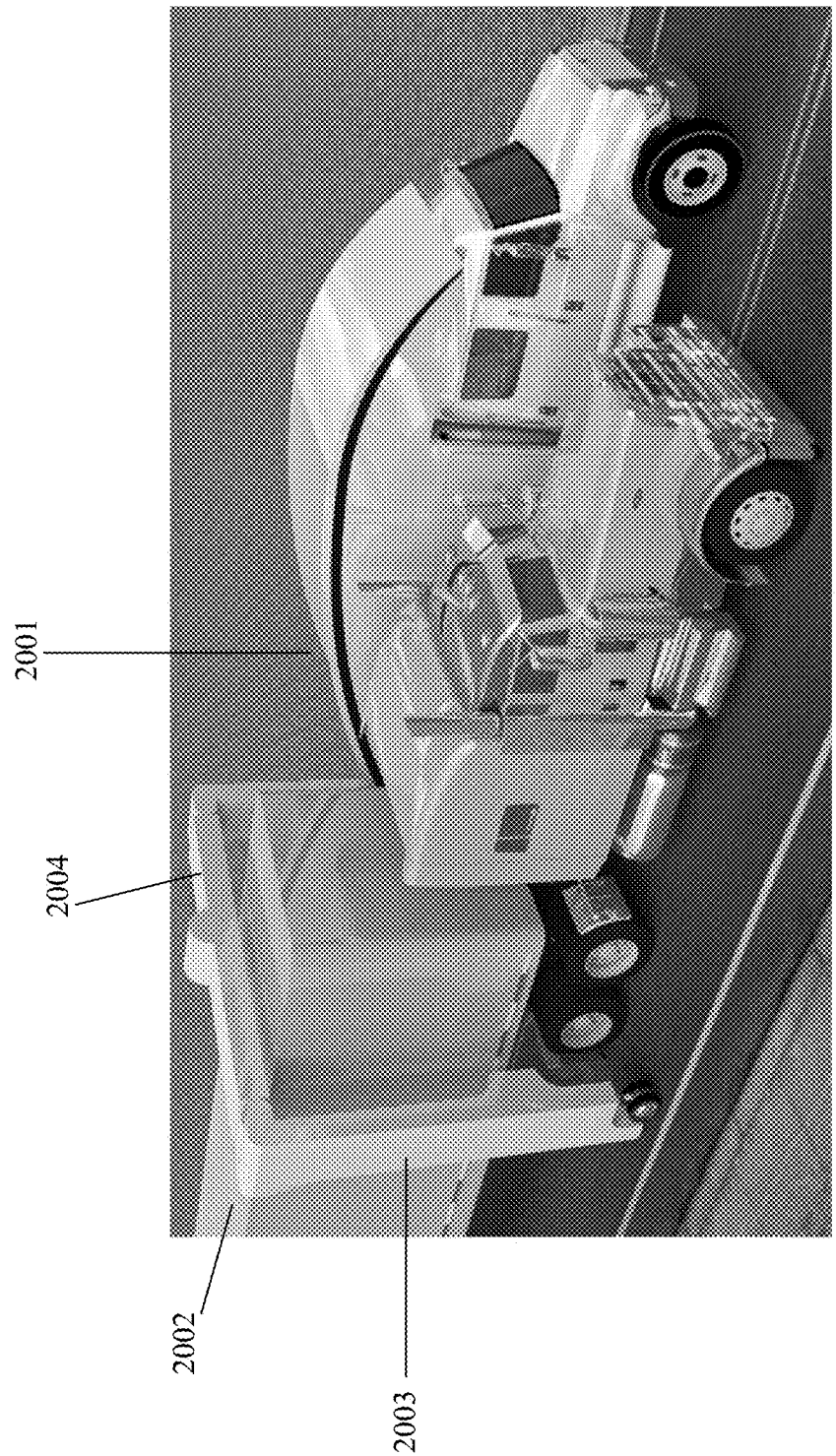
FIG. 20 illustrates an exemplary mobile inspection system in deployed mode, which may use the methods of present specification for automatic detection of threats and contraband.

FIG. 20 illustrates an exemplary mobile inspection system in deployed mode, which may employ any of the methods described in the present specification for processing scanned images and detecting threats and contraband. A person of ordinary skill in the art would appreciate that the system is well capable of scanning large trucks and containers, such as the one 2002 shown in the figure, as well as smaller vehicles. As a vehicle 2002 passes through the portal 2003 created by the boom, it is scanned using the radiation from X-ray source (not shown). X-rays transmitted through (and attenuated by) the vehicle are detected by suitable detectors (not shown). In one embodiment, the detectors are integrated within the portions of the boom 2004 that are opposite to the X-ray source and in the beam path. An image is generated from the detected radiation and it forms the basis of material discrimination. Further details of X-ray scanning systems are provided in U.S. patent application Ser. No. 13/577,170, which is herein incorporated by reference in its entirety. The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method for verifying contents of a tanker, the method comprising:
   at a first physical location, using an X-ray scanner to generate an X-ray image;
   from the first physical location, transmitting the X-ray image to a second physical location remote from the first physical location;
   at the second physical location, receiving the X-ray image;
   at the second physical location, processing the X ray image to detect a presence of contents within the tanker;
   at the second physical location, processing the X ray image to determine a capacity of the tanker;
   at the second physical location, determining a degree of fullness of the tanker based on said contents; and
   at the second physical location, processing the X-ray image to characterize the contents and generate an output indicative of the contents.

2. The method of claim 1, wherein processing the X-ray image to detect the presence of contents within the tanker comprises using a pixel attenuation value threshold.

3. The method of claim 2 wherein the pixel attenuation value threshold is 2,500 for a low-energy channel of a 16-bit normalized dual-energy scanned image.

4. The method of claim 1, wherein processing the X-ray image to determine the capacity of the tanker comprises determining a bottom edge and a top edge of the tanker.

5. The method of claim 4 further comprising processing the X-ray image to determine whether a lower edge of the contents in the tanker coincides with the bottom edge of the tanker.

6. The method of claim 4 further comprising using a pixel attenuation value threshold for determining the top edge of the tanker.

7. The method of claim 6 wherein the pixel attenuation value threshold is 10,000for a low-energy channel of a 16-bit normalized dual-energy scanned image.

8. The method of claim 1, wherein determining a degree of fullness of the tanker comprises calculating a quantity of the contents relative to the capacity of the tanker.

9. The method of claim 1 wherein processing the X-ray image to characterize the contents comprises using X-ray attenuation characteristics for analyzing the contents.

10. The method of claim 1, wherein processing the X-ray image to characterize the contents comprises determining whether the contents comprise at least one of water, regular gasoline, premium gasoline, or diesel.

11. A method of identifying firearms within a radiographic image of a conveyance carrying the firearms, the method comprising:
    at a first physical location, using an X-ray scanner to generate the radiographic image;
    from the first physical location, transmitting the radiographic image to a second physical location remote from the first physical location;
    at the second physical location, receiving the radiographic image;
    at the second physical location, obtaining from a database a template image of a firearm;
    at the second physical location, comparing a set of predefined features of the template image of the firearm with the radiographic image to obtain image regions on the radiographic image comprising features matching the predefined features;
    at the second physical location, filtering the obtained image regions of the radiographic image to obtain a final set of image regions;
    at the second physical location, classifying the final set of image regions to determine one or more regions indicating a presence of a firearm; and
    at the second physical location, marking the one or more regions on the radiographic image to communicate an alarm.

12. The method of claim 11 wherein the template image of the firearm is a radiographic image of a firearm with minimal background and no clutter.

13. The method of claim 11 wherein the template image of the firearm is based on the type of conveyance in which such firearm is transported.

14. The method of claim 11 wherein the conveyance is at least one of a cargo container, a vehicle, a trailer, a boat, a truck, a bus, or a truck driver cab.

* * * * *